US009371295B2

(12) United States Patent
Altamura et al.

(10) Patent No.: US 9,371,295 B2
(45) Date of Patent: Jun. 21, 2016

(54) COMPOUNDS FOR USE IN THE TREATMENT OF DISORDERS THAT ARE AMELIORATED BY INHIBITION OF HDAC

(71) Applicants: IRBM—Science Park S.p.A., Pomezia (RM) (IT); C.N.C.C.S. scarl Collezione Nazionale dei Composti Chimici e Centro Screening, Pomezia (RM) (IT)

(72) Inventors: Sergio Altamura, Pomezia (IT); Alberto Bresciani, Pomezia (IT); Giulia Breveglieri, Ferrara (IT); Danilo Fabbrini, Pomezia (IT); Roberto Gambari, Ferrara (IT); Steven Harper, Pomezia (IT); Ralph Laufer, Pomezia (IT); Edith Monteagudo, Pomezia (IT); Emanuela Nizi, Pomezia (IT); Paola Pace, Pomezia (IT); Vincenzo Summa, Pomezia (IT)

(73) Assignees: IRBM-SCIENCE PARK S.P.A., Pomezia (RM) (IT); C.N.C.C.S. SCARL COLLEZIONE NAZIONALE DEI COMPOSTI CHIMICI E CENTRO SCREENING, Pomezia (RM) (IT)

( * ) Notice: Subject to any disclaimer, the term of this patent is extended or adjusted under 35 U.S.C. 154(b) by 0 days.

(21) Appl. No.: 14/419,988

(22) PCT Filed: Aug. 7, 2013

(86) PCT No.: PCT/EP2013/066524
§ 371 (c)(1),
(2) Date: Feb. 6, 2015

(87) PCT Pub. No.: WO2014/023754
PCT Pub. Date: Feb. 13, 2014

(65) Prior Publication Data
US 2015/0218112 A1 Aug. 6, 2015

(30) Foreign Application Priority Data
Aug. 9, 2012 (IT) .............................. RM2012A0405

(51) Int. Cl.
C07D 263/32 (2006.01)
A61K 31/421 (2006.01)
C07D 413/14 (2006.01)
C07D 413/12 (2006.01)
C07D 417/12 (2006.01)
C07D 417/14 (2006.01)
A61K 31/422 (2006.01)
A61K 31/427 (2006.01)
A61K 31/4439 (2006.01)
A61K 31/454 (2006.01)
A61K 31/4709 (2006.01)
A61K 31/496 (2006.01)

(52) U.S. Cl.
CPC ............ *C07D 263/32* (2013.01); *A61K 31/421* (2013.01); *A61K 31/422* (2013.01); *A61K 31/427* (2013.01); *A61K 31/4439* (2013.01); *A61K 31/454* (2013.01); *A61K 31/4709* (2013.01); *A61K 31/496* (2013.01); *C07D 413/12* (2013.01); *C07D 413/14* (2013.01); *C07D 417/12* (2013.01); *C07D 417/14* (2013.01)

(58) Field of Classification Search
CPC .. C07D 263/32; C07D 413/12; C07D 413/14; C07D 417/12; C07D 417/14; A61K 31/421; A61K 31/422; A61K 31/427; A61K 31/4439; A61K 31/454; A61K 31/4709; A61K 31/496
See application file for complete search history.

(56) References Cited

U.S. PATENT DOCUMENTS 7,863,294 B2 * 1/2011 Attenni ................ C07D 231/10
514/312

FOREIGN PATENT DOCUMENTS

WO 2006/061638 A2 6/2006

OTHER PUBLICATIONS

Costa, Blood Cells, Molecules and Diseases, vol. 55, 95-100, 2015.*
Rotili, Current Topics in MEd Chem, vol. 9, 272-291, 2009.*
Witt O, et al: "Induction of fetal hemoglobin expression by the histone deacetylase inhibitor apicidin", Blood, American Society of Hematology, US, vol. 101, No. 5, Jan. 1, 2003, pp. 2001-2007, the whole document.
Philip Jones, et al: "A Novel Series of Potent and Selective Ketone Histone Deacetylase Inhibitors with Antitumor Activity in Vivo", Journal of Medicinal Chemistry, vol. 51, No. 8, Apr. 1, 2008, pp. 2350-2353, the whole document.
Olaf Kinzel et al: "Discovery of a Potent Class I Selective Ketone Histone Deacetylase Inhibitor with Antitumor Activity in Vivo and Optimized Pharmacokinetic Properties", Journal of Medicinal Chemi Stry, vol. 52, No. 11, Jun. 11, 2009, pp. 3453-3456, the whole document.

(Continued)

Primary Examiner — D M Seaman
(74) Attorney, Agent, or Firm — Lucas & Mercanti, LLP.

(57) ABSTRACT

The present invention relates to compounds of formula (I) and (IV), and pharmaceutically acceptable salts, tautomers, stereoisomers thereof, which are inhibitors of histone deacetylase (HDAC). The compounds of the present invention are for use in the treatment of disorders that are ameliorated by inhibition of HDAC such as cancer and hemoglobinopathies like β-thalassemia or sickle cell anemia.

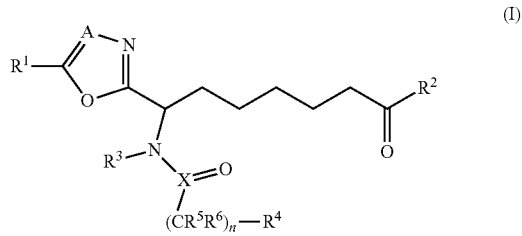

10 Claims, 2 Drawing Sheets

(56) References Cited

OTHER PUBLICATIONS

Pescatore, G., et al: "Optimization of a series of potent and selective ketone histone deacetylase inhibitors", Bioorganic & Medicinal Chemistry Letters, Pergamon, Elsevier Science, GB, vol. 18, No. 20, Oct. 15, 2008, pp. 5528-5532, [retrieved on Jun. 9, 2008], the whole document.

* cited by examiner

COMPOUNDS FOR USE IN THE TREATMENT OF DISORDERS THAT ARE AMELIORATED BY INHIBITION OF HDAC

CROSS-REFERENCE TO RELATED APPLICATIONS

This application is a 371 of PCT/EP2013/066524, filed Aug. 7, 2013, which claims the benefit of European Patent Application No. RM2012A000405, filed Aug. 9, 2012.

FIELD OF THE INVENTION

The present invention relates to heterocycle derivatives that are inhibitors of histone deacetylase (HDAC). Compounds of the present invention are useful for treating disorders that are ameliorated by inhibition of HDAC, in particular genetic disorders, including hemoglobinopathies. Hemoglobinopathies are genetic defects characterized by abnormal structure or underproduction of the normal globin proteins of the hemoglobin molecule (Hb). The major hemoglobinopathies include sickle cell diseases and several forms of thalassemias. Sickle cell anemia results from a missense mutation at the $6^{th}$ aminoacid of the beta-globin chain. The resulting sickle Hb (HbS) forms insoluble polymers within the cytosol upon deoxygenation, with subsequent deformation of the red blood cells and vaso-occlusion. Thalassemias may be traced to numerous genetic mutations that result in either loss or reduced expression of alpha or beta-globin, whereas beta-thalassemias are more common.

In particular, compounds of the invention are useful for treating β-thalassemia and sickle cell anemia.

BACKGROUND OF THE INVENTION

In eukaryotic cells the orderly packaging of DNA in the nucleus plays an important role in the regulation of gene transcription. Nuclear DNA is ordered in a compact complex called chromatin. The core of the complex is an octamer of highly conserved basic proteins called histones. Two each of histones H2A, H2B, H3 and H4 associate and DNA winds around the basic amino acids of the histones interacting with the negatively charged phosphate groups of the DNA. One molecule of histone H1 is associated with each wound core which accommodates approximately 146 bp of DNA. The cores are, in turn, packaged into a compact regular structure with about 200 bp of DNA between each core.

The amino terminal tails of the histones are subject to post-translational modification, in particular by acetylation of lysine. Histone deacetylases (HDACs) and histone acetyl transferases (HATs) determine the pattern of histone acetylation, which together with other dynamic sequential post-translational modifications might represent a 'code' that can be recognised by non-histone proteins forming complexes involved in the regulation of gene expression. This and the ability of histone deacetylases (HDACs) to also modify non-histonic substrates and participate in multi-protein complexes contributes to the regulation of gene transcription, cell cycle progression and differentiation, genome stability and stress responses. HDAC inhibitors cause the induction of differentiation, growth arrest and/or apoptosis in a broad spectrum of transformed cells in culture and tumours in animals, including both haematological cancers and solid tumours. These inhibitory effects are believed to be caused, in part, by accumulation of acetylated proteins, such as nucleosomal histones, which appear to play a major role in regulation of gene transcription. It has been recently discovered that these compounds might represent novel therapeutic agents for the treatment of genetic disorders such as β-thalassemia and sickle cell anemia.

Hemoglobin (Hb) is a tetramer of two α-like and two β-like globin polypeptide chains. In human, the genes for α-globins are clustered on chromosome 16, which contains one gene for ζ and two genes for α ($α_1$ and $α_2$, the proteins of which are identical). The genes for the β-like globins are clustered on chromosome 11, which contains genes for ε, β and δ, one gene for each, and two slightly different genes for γ. In addition, these clusters contain various sites that are responsible for the regulation of the expression of each gene (Steinberg, M H et al, Genetics, Pathophysiology and Clinical Management, Cambridge University Press, Cambridge, UK, 2001).

The expression of the globin genes is regulated during ontogeny. In humans, globin production is characterized by two major "switches" (Thein, S L Br. J. Haematol., 2004, 124, 264). Production of embryonic Hbs switches after the first two months into fetal Hb (HbF) ($α_2γ_2$), and then, again, before and immediately after birth, into adult Hb (HbA) ($α_2β_2$). Since both HbA and HbF contain a chains, the switch from the former to the latter represents a decrease in the expression of the γ-globin genes, associated with an increase of β-globin gene expression. The prevalence of HbF during embryonic life is explained by its high affinity to oxygen, a property that allows it to remove oxygen from HbA in the maternal red blood cells (RBCs) through the placenta.

Immediately after birth the newborn has 85-98% HbF, which gradually decreases to <5% at the age of one year. In adult life HbA is the major Hb, a small <5% is HbA2 ($α_2δ_2$) and the rest (<5%) is HbF which is concentrated in a few RBC.

β-Thalassemia and sickle cell anemia are two of the most common single gene disorders of humans. Both diseases result from different mutations of the β-globin gene that encodes two of the tetramaeric globin chains that make up the major hemoglobin present in adult red cells (adult haemoglobin, HbA).

In β-thalassemias, mutations affecting the β-globin gene or its regulatory regions cause absence ($β^0$) or reduced ($β^+$) synthesis of β-globin chains. This is associated with a corresponding excess of the complementary α-globin. The outcome of this unbalanced globin production is the destruction by apoptosis of erythroid precursors in the bone marrow and at the extramedullary sites (ineffective erythropoiesis) and short survival of RBCs in the peripheral blood (Bank, A. Blood, 2006, 107, 435; Stamatoyannopoulos, G. Exp. Hematol. 2005, 33, 259).

Sickle cell anemia results from a missense mutation (glutamine to valine substitution) at the $6^{th}$ aminoacid of the β-globin chain. The resulting sickle Hb (HbS) forms insoluble polymers within the cytosol upon deoxygenation, with subsequent deformation of the red blood cells and vaso occlusion.

Patients with β-thalassemia and sickle cell disease do not have clinical complications of their disease at birth when their red cells contain the fetal form of Hb (HbF).

The proportion of HbF in postnatal life is influenced by various physiological and genetic factors. Epidemiological findings have shown that increased HbF in β-thalassemia ameliorates the clinical symptoms (Olivieri, N F Semin. Hematol. 1996, 33, 24; Rochette, J et al Blood Rev. 1994, 8, 213). The most convincing finding was found in individuals with mutations associated with hereditary persistence of HbF (HPFH) in adult life (Bhardwaj, U et al Mol. Diagn. 2005, 9, 151). Coexistence of homozygous β-thalassemia with HPFH is asymptomatic. It seems that HbF can functionally compensate for the absence of β-globin chains (Witt, O Am. J. Hematol. 2000, 64, 319).

In sickle cell disease, the presence of HbF reduces the effective concentration of HbS, thus decreasing the propensity for intracellular polymerization. The fetal γ-globin chains also interfere with the ability of HbS to polymerize by heterohybrid formation.

These findings have generated considerable interest in identifying molecular and pharmacological ways to increase the production of HbF. Indeed, several groups of the compounds were found to reactivate the γ-globin genes in postnatal erythroid cells.

Several findings suggest that inhibition of the activity of histone deacetylases (HDACs) is associated with an increased expression of the γ-globin genes (Cao, H Hematology, 2004, 9, 223). Among HDAC inhibitors, trichostatin was found to possess high HbF-inducing activity in human and mouse erythroleukemia cells. Witt et al (Blood, 2003, 101, 2001) showed that, among several specific HDAC inhibitors tested, apicidin was by far the most efficient HbF-inducer (at nM to µM concentrations in K562 cells) and that its effect involved, in addition to HDAC inhibition, p38 mitogen-activated protein (MAP) kinase signaling. Further HDAC inhibitors were recently characterized for their effect on human γ-globin gene expression in transgenic mice. Among the hydroxamic acid derivatives of short chain fatty acids studied butyryl and propionyl hydroxamate were most effective, increasing the human γ/murine α-globin mRNA ratios by 33.9% and 71%, respectively. This was associated with an increase in reticulocytes hematocrit, and the in vivo levels of BFU-E (Cao, H Exp. Hematol. 2005, 33, 1443).

WO 2006/061638 discloses inhibitors of histone deacetylase structurally related to the compounds of the present invention. Such compounds are useful for treating cellular proliferative diseases, including cancer, neurodegenerative disease, schizophrenia and stroke. None of the compounds disclosed in WO 2006/061638 are within the instant invention.

WO 2011/072086 discloses methods and low dose regimens for increasing fetal haemoglobin levels in patients with red blood cell disorders, by administering 2,2-dimethylbutyrate (DMB) alone or in combination with hydroxyurea, decitabine or an HDAC inhibitor.

WO 2009/141658 relates to depsipeptides which act as inhibitors of histone deacetylase (HDAC) and therefore have therapeutic utility in the treatment of conditions mediated by HDAC, including haemoglobinopathy, thalassemia and sickle cell disease.

WO 2003/087057 relates to benzamide derivatives having HDAC inhibitory activity and accordingly having potential value in the treatment of disease states associated with cancer, cystic fibrosis, Huntingtons chorea and sickle cell anemia.

However, many of these drugs have low efficacy and specificity, while some are potentially toxic or carcinogenic. There is therefore an urgent need for new agents that can induce HbF production at doses that are well tolerated by patients, thus with greater efficacy and lower toxicity with respect to known HDAC inhibitors.

The compounds of the present invention are small molecules endowed with potent HDAC inhibitory activity, capable of inducing erythroid differentiation and human γ-globin gene expression. Further, compounds of the invention are characterized by good pharmacokinetic properties in preclinical species, which are predictive of an improved therapeutic window in humans.

SUMMARY OF THE INVENTION

The compounds of this invention are HDAC inhibitors capable of inducing the expression of γ-globin. In particular, provided herein are compounds capable of increasing the percentage of fetal haemoglobin in the blood of a subject.

It is therefore an object of the present invention a compound of formula (I):

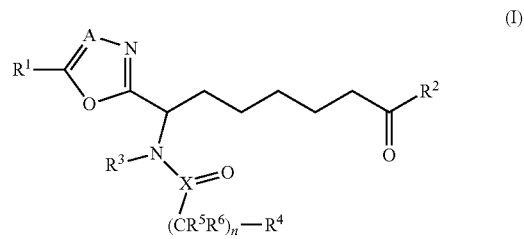

wherein:
X is C or S═O;
A represents CH;
n is 0, 1, 2 or 3;
$R^1$ is phenyl, 5 or 6 membered saturated or unsaturated heterocycle, 8-10 membered unsaturated or partially saturated heterocycle containing heteroatoms independently selected from O, N and S; any of which rings being optionally substituted by one or more groups independently chosen from cyano, halogen, nitro, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$ aryl, $C_{6-10}$aryloxy, $C_{6-10}$arylcarbonyl, $N(R^a)_2$, $SO_2N(R^a)_2$, $N(R^a)SO_2R^a$, 5 or 6 membered saturated or unsaturated heterocycle optionally substituted by one or more groups independently chosen from halogen, $C_{1-6}$alkyl, halo$C_{1-6}$alkyl, $C_{1-6}$alkoxy;
$R^2$ represents $C_{1-6}$alkyl, $C_{3-10}$cycloalkyl;
$R^3$ represents hydrogen or $C_{1-6}$alkyl;
$R^4$ is hydrogen, halogen, hydroxy, cyano, sulphonylamino, $C_{1-6}$alkyl, halo$C_{1-6}$alkyl, hydroxy$C_{1-6}$alkyl, $SO_2C_{1-6}$alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, $N(R^a)_2$, $C_{6-10}$aryl, $C_{6-10}$aryl$C_{1-6}$alkyl, $C_{6-10}$aryl$C_{1-6}$alkoxy; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, 0 or S; any of which rings being optionally substituted by one or more groups independently chosen by one or more groups independently chosen from halogen, hydroxy, amino, $C_{1-6}$alkyl, halo$C_{1-6}$alkyl, $C_{1-6}$alkoxy and halo$C_{1-6}$alkoxy;
$R^5$ and $R^6$ are independently hydrogen, $C_{1-6}$alkyl, or $CR^5R^6$ represents a carbonyl or $CR^5R^6$ represents a cyclopropyl;
each $R^a$ is independently selected from hydrogen, $C_{1-6}$alkyl, $C_{6-10}$aryl, $C_{1-6}$alkylcarbonyl and $C_{6-10}$arylcarbonyl; and pharmaceutically acceptable salts, tautomers, stereoisomers thereof.

In a preferred embodiment, the compound has the general formula (II):

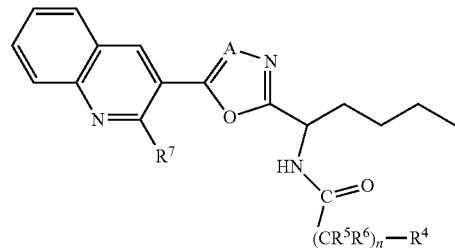

(II)

wherein A, $R^2$ are as defined above;
n is 0 or 1:
$R^7$ is selected from halogen, $C_{1-6}$alkyl, $C_{1-6}$alkoxy, halo$C_{1-6}$alkyl and halo$C_{1-6}$alkoxy; $R^5$ and $R^6$ are independently hydrogen, $C_{1-6}$alkyl, $CR^5R^6$ represents a carbonyl or $CR^5R^6$ represents a cyclopropyl;
$R^4$ is $C_{3-10}$cycloalkyl, halo$C_{3-10}$cycloalkyl, $N(R^a)_2$; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 heteroatoms independently selected from N, O and S, but not more than one of which is O or S; 7-13 membered saturated, partially saturated or unsaturated heterocycle containing heteroatoms independently selected from N, O or S; any of which rings being optionally substituted by one or more groups independently chosen from halogen, hydroxy, amino, $C_{1-6}$alkyl, halo$C_{1-6}$alkyl, $C_{1-6}$alkoxy and halo$C_{1-6}$alkoxy; $R^a$ is $C_{1-6}$alkyl; and pharmaceutically acceptable salts, tautomers, stereoisomers thereof.

In a further preferred embodiment, the compound has the general formula (III):

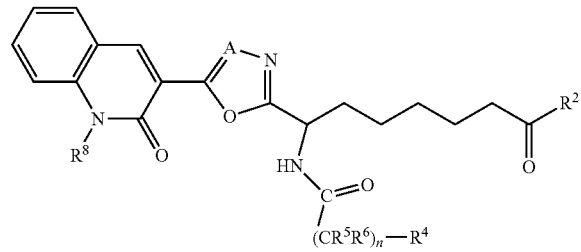

(III)

wherein A, $R^2$ are as defined above and n is 0 or 1;
$R^8$ is $C_{1-6}$alkyl; $R^5$ and $R^6$ are independently hydrogen, $C_{1-6}$alkyl, $CR^5R^6$ represents a carbonyl or $CR^5R^6$ represents a cyclopropyl;
$R^4$ is $C_{3-10}$cycloalkyl, halo$C_{3-10}$cycloalkyl, $N(R^a)_2$; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 heteroatoms independently selected from N, O and S, but not more than one of which is O or S; 7-13 membered saturated, partially saturated or unsaturated heterocycle containing heteroatoms independently selected from N, O or S; any of which rings being optionally substituted by one or more groups independently chosen from halogen, hydroxy, amino, $C_{1-6}$alkyl, halo$C_{1-6}$alkyl, $C_1$-6alkoxy and halo$C_{1-6}$alkoxy; $R^a$ is $C_{1-6}$alkyl; and pharmaceutically acceptable salts, tautomers, stereoisomers thereof.

Preferred compounds are selected from the following list:
(S)-2-(5-methoxy-2-methyl-1H-indol-3-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-1-methylazetidine-3-carboxamide;
(S)-1-methyl-N-(7-oxo-1-(5-phenyloxazol-2-yl)nonyl)piperidine-4-carboxamide;
(S)-2-(5-methoxy-2-methyl-1H-indol-3-yl)-N-(7-oxo-1-(5-phenyloxazol-2-yl)nonyl)acetamide;
((S)-N-(1-(5-(2,3-dihydrobenzo[b][1,4]dioxin-5-yl)oxazol-2-yl)-7-oxononyl)-1-methylpiperidine-4-carboxamide;
(S)-N-(7-oxo-1-(5-phenyloxazol-2-yl)nonyl)thiazole-5-carboxamide;
(S)-3-(dimethylamino)-N-(7-oxo-1-(5-phenyloxazol-2-yl)nonyl)propanamide;
1-methyl-N-((S)-7-oxo-1-(5-phenyloxazol-2-yl)nonyl)pyrrolidine-3-carboxamide;
(S)-2-(dimethylamino)-2-methyl-N-(7-oxo-1-(5-phenyloxazol-2-yl)nonyl)propanamide;
(S)-N-(7-oxo-1-(5-phenyloxazol-2-yl)nonyl)cyclopropane-1,1-dicarboxamide;
(S)-2-(methylsulfonyl)-N-(7-oxo-1-(5-phenyloxazol-2-yl)nonyl)acetamide;
((S)-2-cyclohexyl-N-(7-oxo-1-(5-phenyloxazol-2-yl)nonyl)acetamide;
(R)-2-oxo-N-((S)-7-oxo-1-(5-phenyloxazol-2-yl)nonyl)thiazolidine-4-carboxamide;
(S)-2-chloro-N-(7-oxo-1-(5-phenyloxazol-2-yl)nonyl)isonicotinamide;
(S)-2-(4-methylpiperazin-1-yl)-N-(7-oxo-1-(5-phenyloxazol-2-yl)nonyl)acetamide;
(S)-N-(7-oxo-1-(5-phenyloxazol-2-yl)nonyl)quinoxaline-6-carboxamide;
1-methyl-N-((S)-7-oxo-1-(5-phenyloxazol-2-yl)nonyl)piperidine-3-carboxamide;
(S)-2-(2-methyl-1H-benzo[d]imidazol-1-yl)-N-(7-oxo-1-(5-phenyloxazol-2-yl)nonyl)acetamide;
(S)-6-chloro-N-(7-oxo-1-(5-phenyloxazol-2-yl)nonyl)imidazo[1,2-b]pyridazine-2-carboxamide;
(S)-N-(7-oxo-1-(5-phenyloxazol-2-yl)nonyl)-1H-indole-6-carboxamide;
1-methyl-N-((S)-7-oxo-1-(5-phenyloxazol-2-yl)nonyl)azepane-2-carboxamide;
(S)-N-(7-oxo-1-(5-phenyloxazol-2-yl)nonyl)-4-sulfamoylbutanamide;
2-methyl-N-((S)-7-oxo-1-(5-phenyloxazol-2-yl)nonyl)tetrahydrofuran-2-carboxamide;
(S)-3,3-difluoro-N-(7-oxo-1-(5-phenyloxazol-2-yl)nonyl)cyclobutanecarboxamide;
3-(1-methylpiperidin-3-yl)-N-((S)-7-oxo-1-(5-phenyloxazol-2-yl)nonyl)propanamide;
(S)-3-(2-ethyl-1H-benzo[d]imidazol-1-yl)-N-(7-oxo-1-(5-phenyloxazol-2-yl)nonyl)propanamide;
(S)-$N^1$,$N^1$-dimethyl-$N^2$-(7-oxo-1-(5-phenyloxazol-2-yl)nonyl)oxalamide;
(S)-2-(4-methylpiperazin-1-yl)-2-oxo-N-(7-oxo-1-(5-phenyloxazol-2-yl)nonyl)acetamide;
(S)-3-(2-ethyl-1H-benzo[d]imidazol-1-yl)-N-(1-(5-(2-methoxyquinolin-3-yl)oxazol-2-yl)-7-oxononyl)propanamide;
(S)-4-methyl-N-(7-oxo-1-(5-phenyloxazol-2-yl)nonyl)-3,4-dihydro-2H-benzo[b][1,4]oxazine-7-carboxamide;

(S)-2-(imidazo[2,1-b]thiazol-3-yl)-N-(7-oxo-1-(5-phenyloxazol-2-yl)nonyl)acetamide;
(S)-1-methyl-N-(7-oxo-1-(5-phenyloxazol-2-yl)nonyl)azetidine-3-carboxamide;
(S)-2-(2-aminothiazol-4-yl)-N-(7-oxo-1-(5-phenyloxazol-2-yl)nonyl)acetamide;
N-((S)-1-(5-(2-methoxyquinolin-3-yl)oxazol-2-yl)-7-oxononyl)-1-methylpyrrolidine-3-carboxamide;
(S)-2-(dimethylamino)-N-(1-(5-(2-methoxyquinolin-3-yl)oxazol-2-yl)-7-oxononyl)-2-methylpropanamide;
(S)-N1-(1-(5-(2-methoxyquinolin-3-yl)oxazol-2-yl)-7-oxononyl)-N2,N2-dimethyloxalamide;
(S)-N-(1-(5-(2-methoxyquinolin-3-yl)oxazol-2-yl)-7-oxononyl)-2-(4-methylpiperazin-1-yl)-2-oxoacetamide;
(S)-3-(dimethylamino)-N-(1-(5-(2-methoxyquinolin-3-yl)oxazol-2-yl)-7-oxononyl)propanamide;
(S)-9-((2-(dimethylamino)ethyl)amino)-9-(5-(2-methoxyquinolin-3-yl)oxazol-2-yl)nonan-3-one;
(S)-N-(1-(5-(2-methoxyquinolin-3-yl)oxazol-2-yl)-7-oxononyl)thiazole-5-carboxamide;
(S)-N-(1-(5-(2-methoxyquinolin-3-yl)oxazol-2-yl)-7-oxononyl)quinuclidine-4-carboxamide;
(R)-N-(1-(5-(2-methoxyquinolin-3-yl)oxazol-2-yl)-7-oxononyl)-1-methylazetidine-3-carboxamide;
(S)-2-(5-methoxy-2-methyl-1H-indol-3-yl)-N-(1-(5-(2-methoxyquinolin-3-yl)oxazol-2-yl)-7-oxononyl)-N-methylacetamide;
(S)-1-methyl-N-(7-oxo-1-(5-(2-oxo-1,2-dihydroquinolin-3-yl)oxazol-2-yl)nonyl)azetidine-3-carboxamide;
(S)-N-(1-(5-(4-(1H-pyrazol-5-yl)phenyl)oxazol-2-yl)-7-oxononyl)-1-methylazetidine-3-carboxamide;
(S)-1-methyl-N-(1-(5-(4-(1-methyl-1H-pyrazol-5-yl)phenyl)oxazol-2-yl)-7-oxononyl)azetidine-3-carboxamide;
(S)-1-acetyl-N-(1-(5-(2-methoxyquinolin-3-yl)oxazol-2-yl)-7-oxononyl)azetidine-3-carboxamide;
(S)-1-benzyl-N-(1-(5-(2-methoxyquinolin-3-yl)oxazol-2-yl)-7-oxononyl)azetidine-3-carboxamide;
(S)-N-(1-(5-(2-methoxyquinolin-3-yl)oxazol-2-yl)-7-oxononyl)azetidine-3-carboxamide;
(S)-4,4-difluoro-N-((S)-1-(5-(2-methoxyquinolin-3-yl)oxazol-2-yl)-7-oxononyl)-1-methylpyrrolidine-2-carboxamide;
(S)-N-(1-(5-(2-methoxyquinolin-3-yl)oxazol-2-yl)-7-oxononyl)-2-(1H-1,2,3-triazol-1-yl)acetamide;
(S)-4,4-difluoro-N-((S)-1-(5-(2-methoxyquinolin-3-yl)oxazol-2-yl)-7-oxononyl)pyrrolidine-2-carboxamide;
(S)-N-(1-(5-(4-(1H-pyrazol-1-yl)phenyl)oxazol-2-yl)-7-oxononyl)-1-methylazetidine-3-carboxamide;
(S)-N-(1-(5-(4-(1H-pyrazol-1-yl)phenyl)oxazol-2-yl)-7-oxononyl)-1-acetylazetidine-3-carboxamide;
(S)-2-(dimethylamino)-4,4,4-trifluoro-N-((S)-1-(5-(2-methoxyquinolin-3-yl)oxazol-2-yl)-7-oxononyl)butanamide;
(R)-2-(dimethylamino)-4,4,4-trifluoro-N-((S)-1-(5-(2-methoxyquinolin-3-yl)oxazol-2-yl)-7-oxononyl)butanamide;
(S)-N-(1-(5-(4-(6-methoxypyridin-3-yl)phenyl)oxazol-2-yl)-7-oxononyl)-1-methylazetidine-3-carboxamide;
(2S,4S)-4-fluoro-N-((S)-1-(5-(2-methoxyquinolin-3-yl)oxazol-2-yl)-7-oxononyl)-1-methylpyrrolidine-2-carboxamide;
(S)-3-fluoro-N-(1-(5-(2-methoxyquinolin-3-yl)oxazol-2-yl)-7-oxononyl)-1-methylazetidine-3-carboxamide;
(S)-4-fluoro-N-(1-(5-(2-methoxyquinolin-3-yl)oxazol-2-yl)-7-oxononyl)-1-methylpiperidine-4-carboxamide;
(S)-N-(1-(5-(2-methoxyquinolin-3-yl)oxazol-2-yl)-7-oxononyl)-2-morpholino-2-oxoacetamide;
(S)-1-methyl-N-(7-oxo-1-(5-(quinolin-8-yl)oxazol-2-yl)nonyl)azetidine-3-carboxamide;
N-((S)-1-(5-(2-methoxyquinolin-3-yl)oxazol-2-yl)-7-oxononyl)-5-oxopyrrolidine-3-carboxamide;
(S)-2-(1H-imidazol-4-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-2-(pyridin-3-yl)acetamide;
(S)-3-(1H-imidazol-1-yl)-N-(1-(5-(2-methoxyquinolin-3-yl)oxazol-2-yl)-7-oxononyl)propanamide;
(S)-N-(1-(5-(2-methoxyquinolin-3-yl)oxazol-2-yl)-7-oxononyl)-2-(thiazol-2-yl)acetamide;
(S)-N-(1-(5-(2-methoxyquinolin-3-yl)oxazol-2-yl)-7-oxononyl)-2-(4-methyl-1,2,5-oxadiazol-3-yl)acetamide;
(S)-N-(1-(5-(2-methoxyquinolin-3-yl)oxazol-2-yl)-7-oxononyl)-2-(3-methyl-1H-pyrazol-1-yl)acetamide;
(S)-N-(1-(5-(2-methoxyquinolin-3-yl)oxazol-2-yl)-7-oxononyl)-2-(pyrimidin-2-yl)acetamide;
(S)-2-(3,5-dimethyl-1H-1,2,4-triazol-1-yl)-N-(1-(5-(2-methoxyquinolin-3-yl)oxazol-2-yl)-7-oxononyl)acetamide;
(S)-2-(3,5-dimethyl-1H-pyrazol-1-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-2-(pyrrolidin-1-ylmethyl)thiazole-5-carboxamide;
(S)-N-(1-(5-(2-methoxyquinolin-3-yl)oxazol-2-yl)-7-oxononyl)-2,4-dimethylthiazole-5-carboxamide;
(S)-N-(1-(5-(2-methoxyquinolin-3-yl)oxazol-2-yl)-7-oxononyl)-1,3-dimethylazetidine-3-carboxamide;
N-((S)-1-(5-(2-methoxyquinolin-3-yl)oxazol-2-yl)-7-oxononyl)-1-methylazetidine-2-carboxamide;
(S)-N-(1-(5-(2-methoxyquinolin-3-yl)oxazol-2-yl)-7-oxononyl)-2-(1H-1,2,4-triazol-1-yl)acetamide;
(S)-N-(1-(5-(2-methoxyquinolin-3-yl)oxazol-2-yl)-7-oxononyl)-1-methyl-1H-pyrazole-5-carboxamide;
(S)-2-(2H-indazol-2-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-2-(pyrazolo[1,5-a]pyrimidin-2-yl)acetamide;
(S)-N-(1-(5-(2-methoxyquinolin-3-yl)oxazol-2-yl)-7-oxononyl)-5-methyl-1,3,4-oxadiazole-2-carboxamide;
(S)-N-(1-(5-(2-methoxyquinolin-3-yl)oxazol-2-yl)-7-oxononyl)nicotinamide;
(S)-1-methyl-N-(1-(5-(1-methyl-2-oxo-1,2-dihydroquinolin-3-yl)oxazol-2-yl)-7-oxononyl)azetidine-3-carboxamide;
(S)-N-(1-(5-(2-methoxyquinolin-3-yl)oxazol-2-yl)-7-oxononyl)-3-(1-methyl-1H-pyrazol-4-yl)propanamide;
(S)-N-(1-(5-(2-methoxyquinolin-3-yl)oxazol-2-yl)-7-oxononyl)-3-(piperidin-1-ylmethyl)isothiazole-5-carboxamide;
2-(3,5-dimethyl-1H-pyrazol-1-yl)-N-((S)-1-(5-(2-methoxyquinolin-3-yl)oxazol-2-yl)-7-oxononyl)propanamide;
(S)-N-(1-(5-(2-methoxyquinolin-3-yl)oxazol-2-yl)-7-oxononyl)-1,3-dimethyl-1H-pyrazole-5-carboxamide;
(S)-2-(1H-benzo[d]imidazol-1-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-1-methyl-1H-pyrazole-3-carboxamide;
(S)-N-(1-(5-(2-methoxyquinolin-3-yl)oxazol-2-yl)-7-oxononyl)-1,2,3-thiadiazole-4-carboxamide;
(S)-N-(1-(5-(2-methoxyquinolin-3-yl)oxazol-2-yl)-7-oxononyl)isothiazole-5-carboxamide;
(S)-N-(1-(5-(2-methoxyquinolin-3-yl)oxazol-2-yl)-7-oxononyl)-4-methyl-1,2,3-thiadiazole-5-carboxamide;
N-((S)-1-(5-(2-methoxyquinolin-3-yl)oxazol-2-yl)-7-oxononyl)-2-(1H-pyrazol-1-yl)propanamide;

(S)-2-((dimethylamino)methyl)-N-(1-(5-(2-methoxyquino-lin-3-yl)oxazol-2-yl)-7-oxononyl)thiazole-4-carboxamide;

N-((S)-1-(5-(2-methoxyquinolin-3-yl)oxazol-2-yl)-7-oxononyl)-1-methylpiperidine-3-carboxamide;

(S)-1-(dimethylamino)-N-(1-(5-(2-methoxyquinolin-3-yl)oxazol-2-yl)-7-oxononyl)cyclopentanecarboxamide;

(S)-3-(dimethylamino)-N-(1-(5-(1-methyl-2-oxo-1,2-dihydroquinolin-3-yl)oxazol-2-yl)-7-oxononyl)propanamide;

(S)-2-(dimethylamino)-2-methyl-N-(1-(5-(1-methyl-2-oxo-1,2-dihydroquinolin-3-yl)oxazol-2-yl)-7-oxononyl)propanamide;

(S)-N-(1-(5-(2-methoxyquinolin-3-yl)oxazol-2-yl)-7-oxononyl)-2-(1-methylazetidin-3-yl)acetamide;

(S)-1-methyl-N-(1-(5-(1-methyl-2-oxo-1,2-dihydroquinolin-3-yl)oxazol-2-yl)-7-oxononyl)piperidine-4-carboxamide;

(S)-N-(1-(5-(1-methyl-2-oxo-1,2-dihydroquinolin-3-yl)oxazol-2-yl)-7-oxononyl)thiazole-5-carboxamide;

(S)-1-(dimethylamino)-N-(1-(5-(1-methyl-2-oxo-1,2-dihydroquinolin-3-yl)oxazol-2-yl)-7-oxononyl)cyclopentanecarboxamide; and pharmaceutically acceptable salts, tautomers, stereoisomers thereof.

Even more preferably, the compound is (S)-N-(1-(5-(2-methoxyquinolin-3-yl)oxazol-2-yl)-7-oxononyl)-1-methylazetidine-3-carboxamide.

It is a further object of the invention the compound as defined above for medical use, preferably for use in the treatment of disorders that are ameliorated by inhibition of HDAC and/or for the treatment of hemoglobinopathies and cancer.

In a preferred embodiment the hemoglobinopathies are β-thalassemia or sickle cell anemia.

It is an object of the invention a compound of general formula (IV):

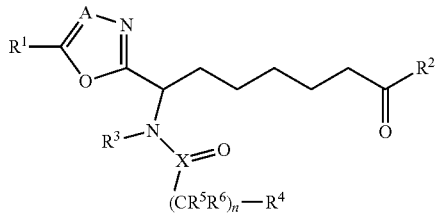

(IV)

wherein:
X is C or S=O;
A represents N;
n is 0, 1, 2 or 3;
$R^1$ is phenyl, 5 or 6 membered saturated or unsaturated heterocycle, 8-10 membered unsaturated or partially saturated heterocycle containing heteroatoms independently selected from O, N and S; any of which rings being optionally substituted by one or more groups independently chosen from cyano, halogen, nitro, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$aryl, $C_{6-10}$aryloxy, $C_{6-10}$arylcarbonyl, $N(R^a)_2$, $SO_2N(R^a)_2$, $N(R^a)SO_2R^a$, 5 or 6 membered saturated or unsaturated heterocycle optionally substituted by one or more groups independently chosen from halogen, $C_{1-6}$alkyl, halo$C_{1-6}$alkyl, $C_{1-6}$alkoxy;
$R^2$ represents $C_{1-6}$alkyl, $C_{3-10}$cycloalkyl;
$R^3$ represents hydrogen or $C_{1-6}$alkyl;
$R^4$ is hydrogen, halogen, hydroxy, cyano, sulphonylamino, $C_{1-6}$ alkyl, halo$C_{1-6}$alkyl, hydroxy$C_{1-6}$alkyl, $SO_2C_{1-6}$ alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, $N(R^a)_2$, $C_{6-10}$aryl, $C_{6-10}$aryl$C_{1-6}$alkyl, $C_{6-10}$aryl$C_{1-6}$alkoxy; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, O or S; any of which rings being optionally substituted by one or more groups independently chosen by one or more groups independently chosen from halogen, hydroxy, amino, $C_{1-6}$alkyl, halo$C_{1-6}$alkyl, $C_{1-6}$ alkoxy and halo$C_{1-6}$ alkoxy;
$R^5$ and $R^6$ are independently hydrogen, $C_{1-6}$alkyl, or $CR^5R^6$ represents a carbonyl or $CR^5R^6$ represents a cyclopropyl;
each $R^a$ is independently selected from hydrogen, $C_{1-6}$alkyl, $C_{6-10}$aryl, $C_{1-6}$alkylcarbonyl and $C_{6-10}$arylcarbonyl; and pharmaceutically acceptable salts, tautomers, stereoisomers thereof, for use in the treatment of hemoglobinopathies.

Preferred compounds of general formula (IV) are selected from the following list:

(S)-N1-(1-(5-(2-methoxyquinolin-3-yl)-1,3,4-oxadiazol-2-yl)-7-oxononyl)-N2,N2-dimethyloxalamide;

(S)-N-(1-(5-(2-methoxyquinolin-3-yl)-1,3,4-oxadiazol-2-yl)-7-oxononyl)-2-(4-methylpiperazin-1-yl)-2-oxoacetamide;

(S)-N-(1-(5-(2-methoxyquinolin-3-yl)-1,3,4-oxadiazol-2-yl)-7-oxononyl)-1-methylpiperidine-4-carboxamide;

(S)-2-(5-methoxy-2-methyl-1H-indol-3-yl)-N-(1-(5-(2-methoxyquinolin-3-yl)-1,3,4-oxadiazol-2-yl)-7-oxononyl)acetamide;

(S)-N-(1-(5-(2-methoxyquinolin-3-yl)-1,3,4-oxadiazol-2-yl)-7-oxononyl)thiazole-5-carboxamide;

(S)-3-(2-ethyl-1H-benzo[d]imidazol-1-yl)-N-(1-(5-(2-methoxyquinolin-3-yl)-1,3,4-oxadiazol-2-yl)-7-oxononyl)propanamide;

(S)-3-(dimethylamino)-N-(1-(5-(2-methoxyquinolin-3-yl)-1,3,4-oxadiazol-2-yl)-7-oxononyl)propanamide;

(S)-N-(1-(5-(2-methoxyquinolin-3-yl)-1,3,4-oxadiazol-2-yl)-7-oxononyl)-1-methylazetidine-3-carboxamide;

(S)-1-methyl-N-(1-(5-(1-methyl-2-oxo-1,2-dihydroquinolin-3-yl)-1,3,4-oxadiazol-2-yl)-7-oxononyl)azetidine-3-carboxamide;

and pharmaceutically acceptable salts, tautomers, stereoisomers thereof, for use in the treatment of hemoglobinopathies.

Preferably, compounds of formula (IV) are for the treatment of β-thalassemia or sickle cell anemia It is a further object of the invention a pharmaceutical composition comprising an effective amount of one or more compounds as defined above or a pharmaceutically acceptable prodrug thereof, alone or in combination with other active compounds, and at least one pharmaceutically acceptable excipient.

Preferably the further active principle is 2,2-dimethylbutyrate, hydroxyurea, decitabine, erythropoietin, trichostatin, valproic acid, or a combination thereof.

The present invention includes within its scope prodrugs of the compounds of formulas (I) to (IV) above. In general, such prodrugs will be functional derivatives of the compounds of the invention which are readily convertible in vivo into the required compound of formulas (I) to (IV). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formulas (I) to (IV) and salts thereof, for example, hydrates.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

The compounds may exist in different isomeric forms, all of which are encompassed by the present invention.

When any variable (e.g. $R^5$ and $R^6$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched and straight-chain saturated aliphatic hydrocarbon groups having the specified number of carbon atoms. For example, "$C_1$-$C_6$ alkyl" is defined to include groups having 1, 2, 3, 4, 5 or 6 carbons in a linear or branched arrangement. For example, "$C_1$-$C_6$ alkyl" specifically includes methyl, ethyl, n-propyl, i-propyl, n-butyl, t-butyl, i-butyl, pentyl, hexyl, and so on. The term "cycloalkyl" means a monocyclic, bicyclic or polycyclic saturated aliphatic hydrocarbon group having the specified number of carbon atoms. For example, "$C_{7-10}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl. "Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy and t-butoxy. The preferred alkoxy group is methoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

The term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. The straight or branched portion of the alkenyl group may contain double bonds and may be substituted if a substituted alkenyl group is indicated. Preferred alkenyl groups include ethenyl and propenyl.

The term "$C_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. The straight or branched portion of the alkynyl group may contain triple bonds and may be substituted if a substituted alkynyl group is indicated. Preferred alkynyl groups include ethynyl and propynyl.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furanyl, furazanyl, imidazolyl, indolinyl, indolyl, indolizinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolidinyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydroisochromenyl, dihydroimidazolonyl, dihydrotriazolonyl, dihydrobenzodioxinyl, dihydrothiazolopyrimidinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, quinazolinyl, pteridinyl and N-oxides thereof. Further particular heterocycles include dihydroquinazolinyl, dihydrophthalazinyl, dihydroisoindolyl, tetrahydronaphthyridinyl, tetrahydrobetacarbolinyl and N-oxides thereof. Attachment of a heterocyclyl substituent can occur via a carbon atom or via a heteroatom.

A preferred 4 membered saturated heterocycle is azetidinyl.

Preferred 5 or 6 membered saturated or partially saturated hetereocycles are pyrrolidinyl, piperidyl, piperazinyl, morpholinyl, azoniabicyclo[2.2.1]heptanyl, azoniabicyclo[2.2.2]octanyl, thiomorpholinyl and thiazolidinyl.

Preferred 5 membered unsaturated heterocycles are thienyl, thiazolyl, pyrazolyl, isoxazolyl, imidazolyl, thiadiazolyl, oxazolyl, triazolyl, tetrazolyl, furyl and oxadiazolyl.

A preferred 6 membered unsaturated heterocycle is pyridinyl.

Preferred 8-10 membered saturated, partially saturated or unsaturated heterocycles are benzothienyl, isoquinolyl, indolyl, benzothiadiazolyl, benzoxadiazolyl, thiazolotriazolyl, dihydrobenzodioxinyl, dihydrothiazolopyrimidinyl, dihydrobenzoxazinyl, dihydrobenzofuranyl, benzothiazolyl, quinolinyl, isoquinolinyl, benzimidazolyl, benzofuranyl, dihydrobenzoxazolyl, dihydroindolyl, dihydroquinazolinyl, dihydrophthalazinyl, indazolyl, benzisoxazolyl, benzotriazolyl, dihydroisoindolyl, tetrahydronaphthyridinyl, triazolopyrimidinyl and tetrahydroquino ling.

A preferred 13 membered partially saturated heterocycle is tetrahydrobetacarbolinyl.

As used herein, the term 'halogen' refers to fluorine, chlorine, bromine and iodine, of which fluorine, chlorine and bromine are preferred.

As used herein, the term 'tautomers' refers to isomers of organic compounds that readily interconvert by a chemical reaction called tautomerization. This reaction commonly results in the formal migration of a hydrogen atom or proton, accompanied by a switch of a single bond and adjacent double bond. Examples of tautomerizations are for instance the interconversion between hydroxypyridine and pyridone or between hydroxyquinoline and quinolone.

Included in the instant invention is the free base of the compounds of formulas (I) to (IV), as well as the pharmaceutically acceptable salts and stereoisomers thereof. Some of the specific compounds exemplified herein are the protonated salts of amine compounds. Compounds of formulas (I) to (IV) containing one or more N atoms may be protonated on any one, some or all of the N atoms. The term "free base" refers to the amine compounds in non-salt form. The encompassed pharmaceutically acceptable salts not only include the salts exemplified for the specific compounds described herein, but also all the typical pharmaceutically acceptable salts of the free form of the compounds of formulas (I) to (IV). The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Preferably, a pharmaceutically acceptable salt of this invention contains one equivalent of a compound of formulas (I) to (IV) and 1, 2 or 3 equivalent of an inorganic or organic acid. More particularly, pharmaceutically acceptable salts of this invention are the tartrate, trifluoroacetate or the chloride salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylamino ethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," J. Pharm. Sci., 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention find use in a variety of applications for human and animal health. The compounds of the invention are histone deacetylase (HDAC) inhibitors useful in the treatment of cancer among other diseases. HDACs catalyse the removal of acetyl groups from lysine residues on proteins, including histones and HDAC inhibitors show diverse biological functions including affecting gene expression, cell differentiation, cell cycle progression, growth arrest, and/or apoptosis. See J. Med. Chem. 2003, 46:5097 and Curr. Med. Chem. 2003, 10:2343.

The compounds, compositions and methods provided herein are particularly deemed useful for the treatment of hemoglopathies, including thalassemias and sickle cell disease.

Thalassemias and sickle cell disease can be characterized as red blood cell disorders and are caused by abnormalities in the globin genes.

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulstion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formulas (I) to (IV) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of formulas (I) to (IV) are employed. (For purposes of this application, topical application shall include mouth washes and gargles).

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of the compound is administered to a mammal undergoing treatment β-thalassemia or sickle cell disease. Administration generally occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents for simultaneous, separate or sequential administration.

In an embodiment, the compounds of the present invention may be used in combination with other inducers of fetal hemoglobin, including hypomethylating agents, hydroxyurea, HDAC inhibitors, DNA binding drugs, oligonucleotides and peptide nucleic acids, Rapamycin, Erythropoietin.

Examples of hypomethylating agents include 5-azacytidine and 5-aza-2'-deoxycytidine. Some examples of HDAC inhibitors are trichostatin, scriptaid, butyryl and propionyl hydroxamate. DNA binding drugs include mithramycin, angelicin, tallimustine and cisplatin.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In some embodiments, pulsed administration is more effetctive than continuous treatment because total pulsed doses are often lower than would be expected from continuous administration of the same composition. Each pulse dose can be reduced and the total amount of drug administered over the course of treatment is minimized. Individual pulses can be delivered to the patient continuously over a period of several hours, such as about 2, 4, 6, 8, 10, 12, 14 or 16 hours, or several days, such as 2, 3, 4, 5, 6 or 7 days.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Abbreviations used in the description of the chemistry and in the Examples that follow are: DMF: dimethylformamide; DMSO: dimethylsulfoxide; MeOH: methanol; EtOH: ethanol; EtOAc: ethyl acetate; DCM: dichloromethane; TFA: trifluoroacetic acid; (g): gas; min: minutes; h: hour(s); eq.: equivalent(s); M: molar; RT: room temperature; RP-HPLC: reversed phase high-pressure liquid chromatography; DIPEA: N,N-diisopropylethylamine; EDCI: 1-(3-dimethylaminopropyl)-3-ethylcarbodiimide hydrochloride; HOBt: 1-hydroxybenzotriazole; and HATU: O-(7-azabenzotriazol-1-yl)-N,N,N',N'-tetramethyluronium hexafluorophosphate.

BRIEF DESCRIPTION OF THE DRAWINGS

The present invention will be described by means of non limiting examples referring to the following figures.

DETAILED DESCRIPTION OF THE INVENTION

Materials and Methods

Chemistry a) General Procedures

Figure 1:
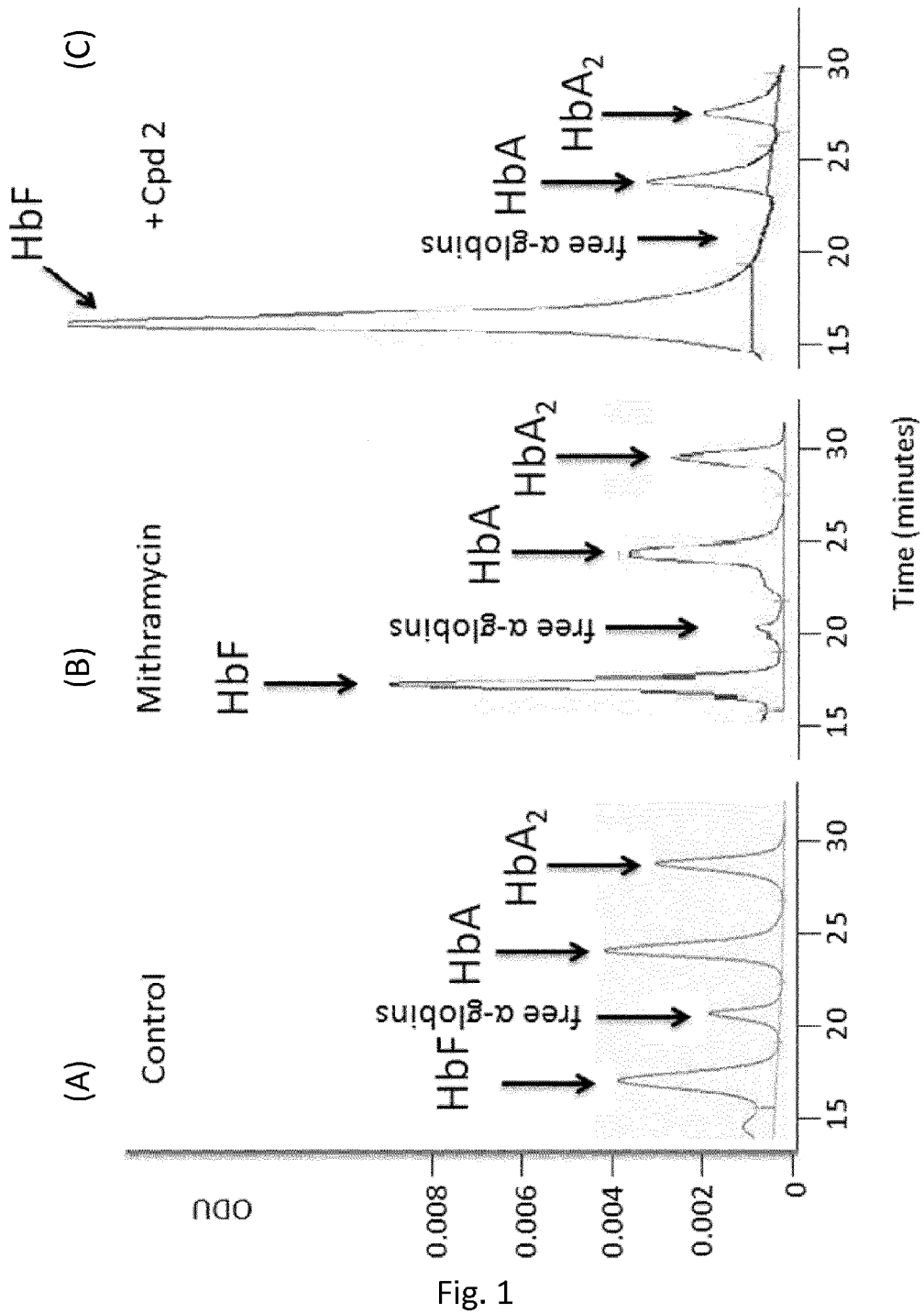
FIG. 1. HPLC chromatograms of hemoglobins produced by cultured erythroid precursor cells from β-thalassemic patients. Control (untreated, panel A), mithramycin treated (50 nM, panel B) and compound 2 treated (100 nM, panel C) cells were harvested, washed and lysed (see material and methods). The hemoglobins in lysate were separated on cation-exchange HPLC. The peaks are labeled with the corresponding hemoglobin type. Increase in the proportion of HbF is detectable in lysates from treated cells. ODU indicates optical density units.

Compounds of formulas (I) and (IV) may be prepared by reacting a compound of formula (IVb) with a compound of formula (V):

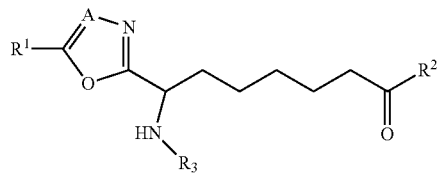
(IVb)

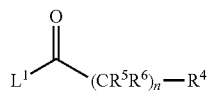
(V)

wherein A is CH or N and $R^1$, $R^2$, $R^3$, $R^4$, $R^5$, $R^6$, n are as defined for formulas (I) and (IV) and $L^1$ is leaving group such as chlorine or hydroxy. When $L^1$ is leaving group such as chlorine, the reaction is generally carried out in the presence of a base such as $Et_3N$ and a solvent such as DMF or DCM at about room temperature. When L' is leaving group such as hydroxyl, a coupling agent such as EDC.HCl and a base such as $Et_3N$ may also be added. Further additives such as HOBT and DIPEA may also be present.

Protecting groups such as dioxane at the carbonyl position of the compounds of formula (IVb) may be present during the reaction. The compounds can be subsequently deprotected using standard methods, such as adding TBAF in a solvent such as THF at reflux, or adding DCM and TFA or HCl(aq) in a solvent such as THF at about room temperature.

Compounds of formula (IVb) wherein A is CH, can be prepared by reacting a compound of formula (VI):

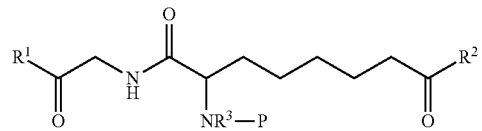
(VI)

wherein $R^1$, $R^2$, $R^3$ are as defined above and P is a protecting group such as BOC or Cbz, with cyclisation agents such as hexachloroethane ($C_2Cl_6$) and triphenylphosphine ($PPh_3$), generally in the presence of a base such as $Et_3N$ and in a solvent such as DCM at about room temperature. Compounds of formula (IVb) wherein A is N, can be prepared by reacting a compound of formula (VII):

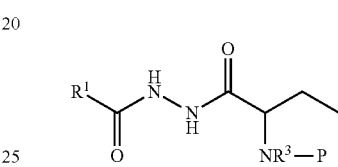
(VII)

wherein $R^1$, $R^2$, $R^3$ and P are as defined above, with cyclisation agents such as PS-BEMP and TsCl, generally in a solvent such as THF at about 65° C.

Compounds of formula (VI) can be prepared by reacting a compound of formula (VIII) with a compound of formula (IX):

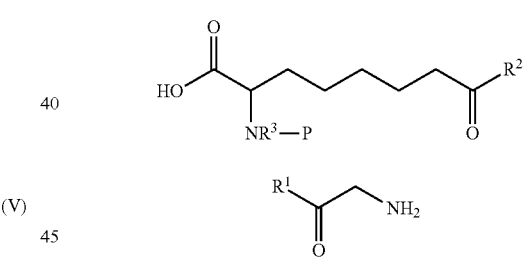
(VIII)

(IX)

wherein $R^1$, $R^2$, $R^3$ and P are as defined above. The reaction is generally carried out in the presence of coupling agents such as HOBt and EDC.HCl, in a base such as DIPEA and a solvent such as DMF.

Compounds of formula (IX) can be prepared by hydrogenation of the corresponding azide of formula (X):

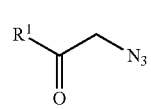
(X)

wherein $R^1$ is as defined above. The reaction is generally carried out in an acid such as HCl, in the presence of a catalyst such as Pd on carbon and in a solvent such as methanol at about room temperature.

Compounds of formula (X) can be prepared by reacting a compound of formula (XI):

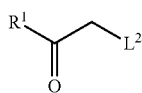

wherein $R^1$ is as defined above and $L^2$ is a leaving group such as halogen, with an azide source such as $NaN_3$, generally in a solvent such as acetone at about room temperature.

Compounds of formula (VII) can be prepared by reacting a compound of formula (VIII) with a compound of formula (XII):

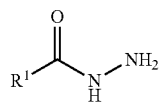

wherein $R^1$ is as defined above. The reaction is generally carried out in the presence of coupling agents such as EDC.HCl and HOBt, in a solvent such as DMF at room temperature.

Compounds of formula (XII) can be prepared by reacting a compound of formula (XIII) with hydrazine monohydrate:

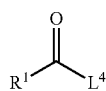

wherein $R^1$ is as defined above and $L^4$ is an appropriate leaving group such as methoxy. The reaction is generally carried out in a solvent such a i-PrOH at about 80° C. Alternatively, compounds of formula (XII) can be prepared by reacting a compound of formula (XIII) wherein $L^4$ is OH with Boc-hydrazine in the presence of coupling reagents, followed by BOC deprotection with acid such as TFA.

Where the synthesis of intermediates and starting materials is not described, these compounds are commercially available or can be made from commercially available compounds by standard methods or by extension of the Examples herein. Compounds of formulas (I) to (IV) may be converted to other compounds of formulas (I) to (IV) by known methods or by methods described in the Examples.

During any of the synthetic sequences described herein it may be necessary and/or desirable to protect sensitive or reactive groups on any of the molecules concerned. This may be achieved by means of conventional protecting groups, such as those described in Protecting Groups in Organic Synthesis, 3rd Edition, Greene, T. W. and Wuts, P. G. M.; Wiley Interscience, 1999 and Kocienski, P. J. Protecting Groups, Thieme, 1994. The protecting groups may be removed at a convenient subsequent stage using methods known from the art. For example, when the Boc protecting group is present, it may be removed by the addition of solvents such as TFA and DCM. The compound may also be hydrogenated using standard methods, such as treating with a catalyst such ad Pd/C, in a solvent such as methanol in a hydrogen atmosphere. As described previously the heterocyclic group may be protected by protecting groups such as SEM during the synthesis of the compounds of formulas (I) to (IV), which can subsequently be removed under standard conditions as described above.

Further examples of protecting groups on the heterocyclic ring include tert-butyl(dimethyl)silylmethyl and BOM. The BOM group may subsequently be removed using standard methods, for example by the addition of a reagent such as $BBr_3$ and a solvent such as toluene at about room temperature.

Compounds of this invention can be prepared as described in Scheme 1 from a suitably elaborated alkyl chain functionalised in the α-position with an amino derivative. These derivatives can be prepared by those skilled in the art and methods to synthesise such heterocycles are described in Alan Katritzky, Comprehensive Heterocyclic Chemistry. (Pergamon Press, New York, 1984) and Comprehensive Heterocylic Chemistry IL (Pergamon Press, New York, 1996) amongst other texts. The free amino group can be coupled with an acid derivative to form amides, methods for coupling carboxylic acids (and acid derivatives) with amines to form carboxamides are well known in the art. Suitable methods are described, for example, in Jerry March, Advanced Organic Chemistry, 3rd edition, John Wiley & Sons, 1985, pp. 370-376. Likewise reaction with a sulfonyl chloride in the presence of base gives the corresponding sulfonamide, see Jerry March, Advanced Organic Chemistry. 4th edition, John Wiley & Sons, 1992, pp. 496-499. In a similar manner, reaction of the amine with a sulfamoyl chloride gives the corresponding sulfamide.

Scheme 1

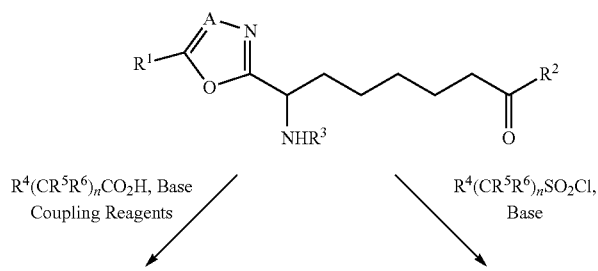

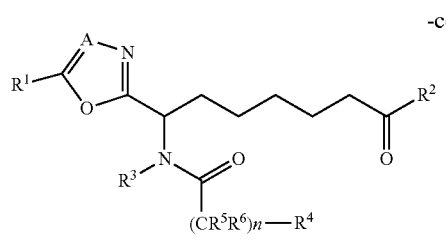
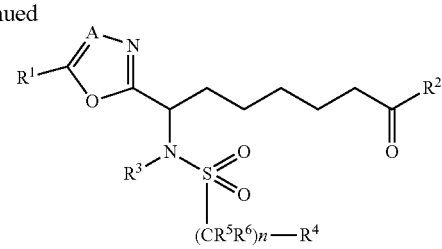

A synthetic route to the preparation of 1,3,4-oxadiazoles is shown in Scheme 2 where a hydrazide is readily coupled with a second carboxylic acids and then cyclised under dehydrative conditions to form the desired heterocyclic ring. Suitable conditions include the use of tosyl chloride and polymer supported BEMP as described by Brain et al. Synlett 2001, 3, 382-384. Subsequently, the protecting group can be removed from the nitrogen atom and the required inhibitors can be synthesised as previously described.

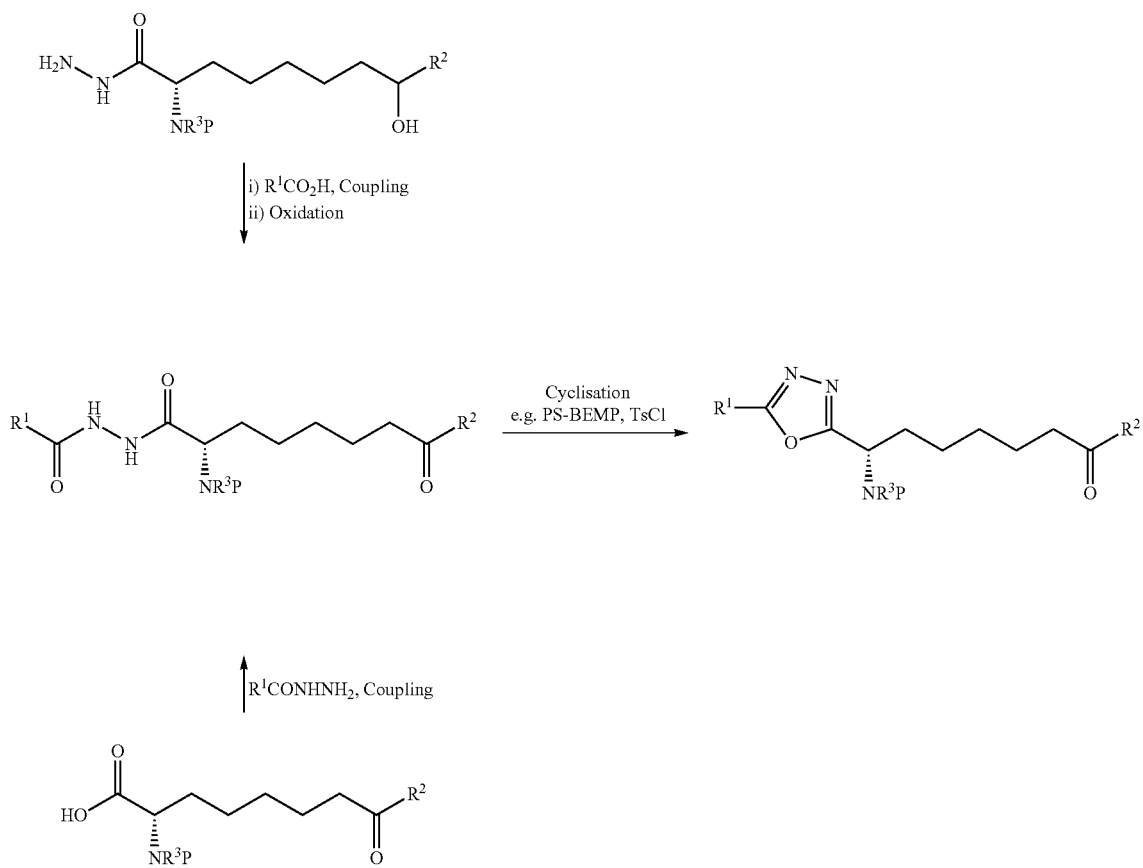

Scheme 2

An alternative procedure, in this case for the preparation of oxazoles, is shown in Scheme 3, where a α-aminoketone is coupled with a carboxylic acid, the resulting amide there formed can then be cyclised again under dehydrative conditions to yield the desired heterocycle. One method for performing the cyclisation is to use hexachloroethane and triphenylphosphine as described by Nicolaou et al. J. Am. Chem. Soc 2004, 126, 10162-10173.

Scheme 3

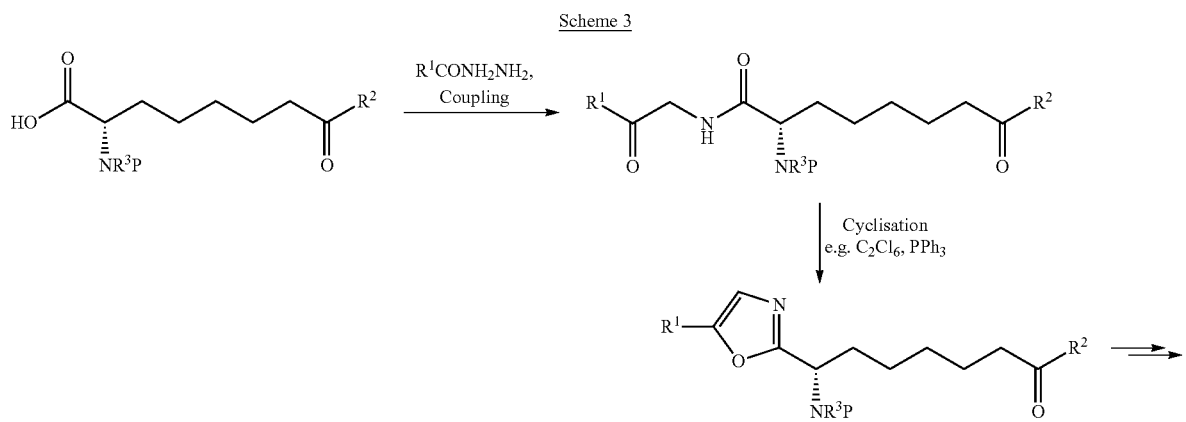

b) Examples

The following Examples illustrate the present invention.

Example 1

(S)-2-(5-methoxy-2-methyl-1H-indol-3-yl)-N-(1-(5-(2-methoxyquinolin-3-yl)oxazol-2-yl)-7-oxononyl) acetamide (Compound 1)

Step 1: tert-butyl(2-(2-methoxyquinolin-3-yl)-2-oxoethyl)carbamate

To a solution of mesyl bromide (17.23 mmol) in 10 mL of THF cooled to −78° C. was added a 1.7 M THF solution of tBuLi (34.5 mmol) dropwise. The mixture was left stirring at −78° C. for 1 h. The mixture was then allowed to reach 0° C. and a solution of 2-methoxyquinoline (12.9 mmol) in THF (40 mL) was added dropwise over 10 min. The resulting mixture was aged at 0° C. for 1 h, cooled to −78° C. and added dropwise with a solution of tert-butyl(2-(methoxy(methyl)amino)-2-oxoethyl)carbamate (4.31 mmol) in 20 mL of THF. The mixture was stirred at −78° C. for 30 min then left at room temperature over night. The mixture was diluted with DCM and washed with sat. aq. NaHCO$_3$, dried (Na$_2$SO$_4$), concentrated under reduced pressure and the crude product was purified by flash chromatography (SiO$_2$, Petroleum ether/EtOAc, from 5% to 40% EtOAc). Pooled fractions were concentrated under vacuum to title product (1.01 g). MS (ES) $C_{17}H_{20}N_2O_4$ requires: 316.35, found: 317.

Step 2: 2-amino-1-(2-methoxyquinolin-3-yl)ethanone

Compound from the previous step was solubilized in dioxane (30 mL) and treated with 16 mL of 4N HCl in dioxane at 0° C. The mixture was stirred for 1 h at room temperature, poured in sat. aq. NaHCO$_3$, and extracted with DCM. The organic phase was dried (Na$_2$SO$_4$), filtered and concentrated to crude product, used directly in the next step. MS (ES) $C_{12}H_{12}N_2O_2$ requires: 216.24, found: 217.

Step 3: (S)-tert-butyl(1-((2-(2-methoxyquinolin-3-yl)-2-oxoethyl)amino)-1,8-dioxodecan-2-yl)carbamate A solution of (S)-2-((tert-butoxycarbonyl)amino)-8-oxodecanoic acid (0.76 mmol, 1 eq), EDC.HCl (0.99 mmol, 1.3 eq), HOBT (0.99 mmol, 1.3 eq) in DMF (3 mL) was stirred at room temperature for 10 min. A solution of 2-amino-1-(2-methoxyquinolin-3-yl)ethanone (1 eq) in 3 mL of DMF and DIPEA (2 eq) was added and the mixture was stirred at room temperature for 2 h. Mixture was diluted with DCM and washed with brine. The organic phase was dried (Na$_2$SO$_4$), filtered and concentrated. Residue was purified by flash chromatography (SiO$_2$, Petroleum ether/EtOAc, from 10% EtOAc to 80% EtOAc), to isolate title compound in 20% yield. MS (ES) $C_{27}H_{37}N_3O_6$ requires: 499.60, found: 500.

Step 4: (S)-tert-butyl(1-(5-(2-methoxyquinolin-3-yl)oxazol-2-yl)-7-oxononyl)carbamate PPh$_3$ (1.08 mmol) and C$_2$Cl$_6$ (1.08 mmol) were dissolved in DCM (1.5 mL) at room temperature and Et$_3$N was added (2.16 mmol), followed after 5 min of stirring by dropwise addition of a solution of the amide from the previous step (0.54 mmol) in DCM (1.5 mL). The mixture was stirred for 1 h at room temperature and was then poured in water. The organic phase was separated, washed with brine, dried (Na$_2$SO$_4$), filtered and concentrated under reduced pressure. The product was purified by flash chromatography on silica using 30% EtOAc/Petroleum ether as eluent to afford the title product. MS (ES) $C_{27}H_{35}N_3O_5$ requires: 481.58, found: 482.

Step 5: (S)-9-amino-9-(5-(2-methoxyquinolin-3-yl)oxazol-2-yl)nonan-3-one

Compound from the previous step was dissolved in a mixture DCM: TFA (1:1, 2.2 mL) and stirred at 0° C. for 40 min then at room temperature for 10 min. The mixture was diluted with toluene (7 mL) and solvent evaporated. The resulting oil was diluted with DCM and washed with sat. aq. NaHCO$_3$ solution, dried (Na$_2$SO$_4$), filtered and concentrated under reduced pressure. The product was used directly in the following step. MS (ES) $C_{22}H_{27}N_3O_3$ requires: 381.47, found: 382.

Step 6: (S)-2-(5-methoxy-2-methyl-1H-indol-3-yl)-N-(1-(5-(2-methoxyquinolin-3-yl)oxazol-2-yl)-7-oxononyl)acetamide A solution of 5-methoxy-2-methyl-1H-indol-3-yl)acetic acid (1.3 eq), HOBT (1.3 eq), EDC.HCl (1.3 eq) in DMF (premixed for 3 min) was added to (S)-9-amino-9-(5-(2-methoxyquinolin-3-yl)oxazol-2-yl)nonan-3-one from the previous step (1 eq), followed by DIPEA (1.3 eq). The mixture was stirred at room temperature over night. The product was purified by preparative RP-HPLC, using water (+0.1% TFA) and MeCN (+0.1% TFA) as eluents ($C_{18}$ column). MS (ES) $C_{34}H_{38}N_4O_5$ requires: 582.69, found: 583.

Example 2

(S)-N-(1-(5-(2-methoxyquinolin-3-yl)oxazol-2-yl)-7-oxononyl)-1-methylazetidine-3-carboxamide (Compound 2)

Step 1: (S)-tert-butyl 3-((1-(5-(2-methoxyquinolin-3-yl)oxazol-2-yl)-7-oxononyl)carbamoyl) azetidine-1-carboxylate A solution of 1-(tert-butoxycarbonyl)azetidine-3-carboxylic acid (1.3 eq), HOBt (1.3 eq) and EDC.HCl (1.3 eq) in DMF (premixed for 10 min) was added to (S)-9-amino-9-(5-(2-methoxyquinolin-3-yl)oxazol-2-yl)nonan-3-one (1 eq), obtained as described above. The mixture was stirred o/n at room temperature. Reaction mixture was diluted with DCM, washed with sat. aq. $NaHCO_3$ solution, brine, dried ($Na_2SO_4$), filtered and concentrated. The mixture was purified by flash chromatography on silica, eluting with EtOAc/Petroleum ether (from 50% of EtOAc to 80% of EtOAc). MS (ES) $C_{31}H_{40}N_4O_6$ requires: 564.67, found: 565.

Step 2: (S)-N-(1-(5-(2-methoxyquinolin-3-yl)oxazol-2-yl)-7-oxononyl)azetidine-3-carboxamide Compound from the previous step (67 mg) was treated with 2.9 mL of DCM and 0.6 mL of TFA at 0° C. The mixture was stirred at 0° C. for 30 min, diluted with $Et_2O$ and evaporated under vacuum. The residue was dissolved with DCM and washed with sat. aq. $NaHCO_3$ solution, dried ($Na_2SO_4$), filtered and concentrated. The product was used directly in the next step. MS (ES) $C_{26}H_{32}N_4O_4$ requires: 464.56, found: 465.

Step 3: (S)-N-(1-(5-(2-methoxyquinolin-3-yl)oxazol-2-yl)-7-oxononyl)-1-methylazetidine-3-carboxamide The compound from the previous step (0.13 mmol, 1 eq) was dissolved in MeOH (1.5 mL) and formaldehyde (3.5 eq, 37% aq. Solution) was added and the mixture was stirred for 10 minutes at room temperature. NaOAc (3.0 eq) and $NaBH_3CN$ (3.0 eq) were added and the mixture was stirred for 1 h at room temperature. Solvent was removed under reduced pressure, dissolved in acetonitrile and purified by RP-HPLC (Acetonitrile/$H_2O$+0.01% TFA). The product was obtained as TFA salt. MS (ES) $C_{27}H_{34}N_4O_4$ requires: 478.58, found: 479. $^1$H-NMR (300 MHz, DMSO-$d_6$) δ: 8.67 (1 H, d, J=6.3 Hz), 8.53 (1 H, s), 8.02 (1 H, d, J=6.0 Hz), 7.82 (1 H, d, J=6.3 Hz), 7.71 (1 H, t, J=5.7 Hz), 7.65 (1 H, s), 7.50 (1 H, t, J=5.7 Hz), 5.11-5.05 (1 H, m), 4.38-4.30 (1 H, m), 4.25-4.09 (3 H, s+2 H, m), 3.99-3.89 (1 H, m), 3.6 (1 H, m, partially overlaps with water), 2.83 (3 H, s), 2.42-2.31 (m, 4 H), 2.00-1.80 (m, 2 H), 1.49-1.40 (2 H, m), 1.25 (4 H, bs), 0.97 (3 H, t, J=7.2 Hz).

Example 3

(S)-N-(1-(5-(2-methoxyquinolin-3-yl)-1,3,4-oxadiazol-2-yl)-7-oxononyl)-1-methylazetidine-3-carboxamide (Compound 52)

Step 1: tert-butyl 2-(2-methoxyquinoline-3-carbonyl)hydrazinecarboxylate

To a stirred suspension of 2-methoxyquinoline-3-carboxylic acid (0.92 g, 4.55 eq) in DCM (45 mL) under $N_2$, HOBT (6.83 mmol, 1.5 eq), EDC.HCl (6.83 mmol, 1.5 eq) triethylamine (5.0 mmol, 1.1 eq) and tert-butylhydrazine carboxylate (5.00 mmol, 1.1 eq) were added. The mixture was stirred at room temperature for 3 h, diluted with DCM and washed with sat. aq. $NaHCO_3$ and sat. aq. NaCl. The organic phase was dried ($Na_2SO_4$), concentrated under reduced pressure and the product was purified by flash chromatography ($SiO_2$, Petroleum ether/EtOAc 9:1 to 0:100) affording 1.23 g of product as a white solid (85% yield). MS (ES) $C_{16}H_{19}N_3O_4$ requires: 317.34, found: 318.

Step 2: 2-methoxyquinoline-3-carbohydrazide tert-Butyl 2-(2-methoxyquinoline-3-carbonyl)hydrazinecarboxylate (1.23 g, 3.87 mmol) was dissolved in DCM (10 mL) and cooled to 0° C. Trifluoroacetic acetic acid (10 mL) was added and the mixture was stirred at room temperature for 1 h. Solvents were evaporated and the residue was washed with water. The product was used without purification in the next step. MS (ES) $C_{11}H_{11}N_3O_2$ requires: 217.22, found: 218.

Step 3: (S)-tert-butyl(1-((2-(2-methoxyquinoline-3-carbonyl)hydrazinyl)oxy)-1,8-dioxodecan-2-yl)carbamate A solution of (S)-2-((tert-butoxycarbonyl)amino)-8-oxodecanoic acid (0.6 g, 1.99 mmol), EDC.HCl (1.5 eq) and HOBT (1.5 eq) in DMF (6 mL) was stirred for 10 min. To the mixture was added a solution of crude hydrazide (0.99 g, 2.99 mmol, 1 eq) and DIPEA (2.0 eq). The mixture was stirred at room temperature for 2 h. Reaction mixture was diluted with EtOAc, the organic phase was washed with sat. aq. $NaHCO_3$ and brine, dried ($Na_2SO_4$), and concentrated under reduced pressure. Residue was purified by flash chromatography ($SiO_2$, Petroleum ether/EtOAc 9:1 to 0:100) affording product in 48% yield. MS (ES) $C_{26}H_{36}N_4O_7$ requires: 516.59, found: 517.

Step 4: (S)-tert-butyl(1-(5-(2-methoxyquinolin-3-yl)-1,3,4-oxadiazol-2-yl)-7-oxononyl) carbamate A mixture of (S)-tert-butyl(1-((2-(2-methoxyquinoline-3-carbonyl)hydrazinyl)oxy)-1,8-dioxodecan-2-yl)carbamate (0.48 g, 1 eq), 2-tert-butylimino-2-diethylamino-1,3-dimethyl-perhydro-1,3,2-diazaphosphorine bound on polystyrene (5 eq) and tosyl chloride (1.2 eq) was suspended in anhydrous THF. The suspension was heated at 65° C. and stirred for 4 h. The mixture was filtered and the resin was washed with THF. The combined filtrates were concentrated under reduced pressure. The residue was purified by flash chromatography $SiO_2$, Petroleum ether/EtOAc 1:9 to 0:100) affording product affording product as a colorless oil (0.33 g, 72% yield). MS (ES) $C_{26}H_{34}N_4O_5$ requires: 482.57, found: 483.

Step 5: (S)-9-amino-9-(5-(2-methoxyquinolin-3-yl)-1,3,4-oxadiazol-2-yl)nonan-3-one To a solution of oxadiazole from the previous step (0.68 mmol) in DCM (6.1 mL) at 0° C., 0.7 mL of TFA was added. The cooling bath was removed and the mixture was stirred at room temperature for 30 min. The solvents were removed under reduced pressure and the residue was partitioned between DCM and sat. aq. $NaHCO_3$ solution. The organic phase was dried ($Na_2SO_4$) and concentrated under reduced pressure. The crude product was used directly in the next step. MS (ES) $C_{21}H_{26}N_4O_3$ requires: 382.46, found: 383.

Step 6: (S)-tert-butyl 3-((1-(5-(2-methoxyquinolin-3-yl)-1,3,4-oxadiazol-2-yl)-7-oxononyl) carbamoyl) azetidine-1-carboxylate To the crude amine from previous step (0.15 mmol, 1 eq) was added a solution of 1-(tert-butoxycarbonyl)azetidine-3-carboxylic acid (1.3 eq), HOBt (1.3 eq) and EDC.HCl (1.3 eq) in DMF (premixed fopr 10 min). The mixture was stirred o/n at room temperature. Reaction mixture was diluted with EtOAc, washed with sat. aq. NaHCO$_3$ solution, brine, dried (Na$_2$SO$_4$), filtered and concentrated. The product was used in the next step without further purification. MS (ES) $C_{30}H_{39}N_5O_6$ requires: 565.66, found: 567.

Step 7: (S)-N-(1-(5-(2-methoxyquinolin-3-yl)-1,3,4-oxadiazol-2-yl)-7-oxononyl)azetidine-3-carboxamide To a solution of the compound from the previous step (0.15 mmol) in DCM (1.35 mL) at 0° C., 0.15 mL of TFA was added. The mixture was stirred at room temperature for 3 h, diluted with DCM, washed with sat. aq. NaHCO$_3$ solution, brine, dried, filtered and concentrated to afford the title compound as yellow solid in quantitative yield. MS (ES) $C_{25}H_{31}N_5O_4$ requires: 465.54, found: 466.

Step 8: (S)-N-(1-(5-(2-methoxyquinolin-3-yl)-1,3,4-oxadiazol-2-yl)-7-oxononyl)-1-methylazetidine-3-carboxamide The compound from the previous step (0.14 mmol, 1 eq) was dissolved in MeOH (1.4 mL) and formaldehyde (3.5 eq, 37% aq. Solution) was added and the mixture was stirred for 4 minutes at room temperature. NaOAc (3.0 eq) and NaBH$_3$CN (3.0 eq) were added and the mixture was stirred for 1 h at room temperature. Solvent was removed under reduced pressure and dissolved in acetonitrile and purified by RP-HPLC (Acetonitrile/H$_2$O+0.01% TFA). The product was obtained as TFA salt in 50% yield. The product was partitioned between EtOAc and sat. aq. NaHCO$_3$ solution. Organic phase was dried and concentrated. The residue was dissolved in acetonitrile/H$_2$O 2/3 and treated with equimolar tartaric acid. The resulting solution was lyophilized to obtain the product as tartrate salt. $^1$H-NMR (300 MHz, DMSO-d$_6$) δ: 8.89 (1 H, s), 8.74 (1H, d, J=7.8 Hz), 8.09 (1H, d, J=7.8 Hz), 7.84 (2H, m), 7.57 (1H, m), 5.18 (1H, m), 4.10 (3H, s), 3.80 (2H, t, J=8.4 Hz), 3.58 (2H, m), 2.39 (4H, m), 1.50-1.27 (6H, m), 0.90 (3H, t, J=7.2 Hz).

Example 4

(S)-2-(5-methoxy-2-methyl-1H-indol-3-yl)-N-(1-(5-(2-methoxyquinolin-3-yl)-1,3,4-oxadiazol-2-yl)-7-oxononyl)acetamide (Compound 48)

(S)-9-amino-9-(5-(2-methoxyquinolin-3-yl)-1,3,4-oxadiazol-2-yl)nonan-3-one (0.05 mmol, 1 eq), prepared as described above, was treated with a solution of (5-methoxy-2-methyl-1H-indol-3-yl)acetic acid (1.3 eq), HOBT (1.3 eq) and EDC.HCl (1.3 eq) in DMF (premixed for 3 min), followed by DIPEA (1.3 eq). The mixture was stirred at room temperature for 2 h and the product was isolated by preparative RP-HPLC, using water (+0.01% TFA) and MeCN (+0.01% TFA) as eluents (column C18). The pooled product fractions were lyophilized and the product was obtained as a white solid. MS (ES) $C_{33}H_{37}N_5O_5$ requires: 583.68, found: 584.

Example 5

(S)-2-(5-methoxy-2-methyl-1H-indol-3-yl)-N-(1-(5-(2-methoxyquinolin-3-yl)oxazol-2-yl)-7-oxononyl)-N-methylacetamide (Compound 43)

Step 1: (S)-9-(benzyl(methyl)amino)-9-(5-(2-methoxyquinolin-3-yl)oxazol-2-yl)nonan-3-one (S)-9-amino-9-(5-(2-methoxyquinolin-3-yl)oxazol-2-yl)nonan-3-one (0.21 mmol, 1 eq), prepared as described above, was solubilized in dichloroethane (2.1 mL) and treated with benzaldehyde (0.17 mmol, 0.8 eq). The mixture was stirred 1 h at room temperature then treated with NaBH(AcO)$_3$ (0.21 mmol, 1 eq). After stirring 30 min at room temperatures, a 37% solution of HCHO in water (3 eq) and NaBH(AcO)$_3$ (0.21 mmol, 3 eq). After 10 minutes, the mixture was diluted with DCM and washed with water and brine. The organic phase was dried, filtered and concentrated. Residue was purified by flash chromatography using EtOAc/Petroleum Ether in a linear gradient from 4% to 40% of EtOAc. The product was obtained as a colorless oil in 53% yield. MS (ES) $C_{30}H_{35}N_3O_3$ requires: 485.62, found: 486. $^1$H-NMR (300 MHz, DMSO-d$_6$) δ: 8.58 (1 H, s), 8.05 (1 H, d, J=5.4 Hz), 7.81 (1 H, d, J=6.3 Hz), 7.71 (2 H, m). 7.49 (1 H, t, J=5.4 Hz), 7.34-7.30 (4 H, m), 7.27-7.22 (1 H, m), 4.17 (3 H, s), 3.95 (1 H, t, J=5.7 Hz), 3.72 (1 H, d, J=10.2 Hz), 3.49 (1 H, d, J=10.2 Hz), 2.41-2.34 (2 H, m), 2.18 (3 H, s), 1.99-1.93 (2 H, m), 1.50-1.41 (4 H, m), 1.27-1.23 (4 H, m), 0.89 (3 H, t, J=5.4 Hz).

Step 2: (S)-9-(5-(2-methoxyquinolin-3-yl)oxazol-2-yl)-9-(methylamino)nonan-3-one The product from the previous step was taken in EtOAc (7 mL) and treated with Pd/C (5 mg). The mixture was purged with N$_2$ and stirred under H$_2$ atmosphere at room temperature for 3 days. Reaction mixture was filtered through a pad of silica and filtrate was concentrated under vacuum. The product was used in the next step. MS (ES) $C_{23}H_{29}N_3O_3$ requires: 395.49, found: 396.

Step 3: (S)-2-(5-methoxy-2-methyl-1H-indol-3-yl)-N-(1-(5-(2-methoxyquinolin-3-yl)oxazol-2-yl)-7-oxononyl)-N-methylacetamide To a solution of 2-methyl-5-methoxyindolyl acetic acid (0.1 mmol, 1 eq) in DCM, oxalyl chloride (1.5 eq) was added at room temperature. The mixture was stirred 1 h, then evaporated and kept at high vacuum for 30 min. The acyl chloride was solubilized again in DCM and added to a solution of (S)-9-(5-(2-methoxyquinolin-3-yl)oxazol-2-yl)-9-(methylamino)nonan-3-one from the previous step, in DCM and DIPEA (3 eq). After 30 min stirring at room temperature, mixture was purified by RP-HPLC, using water (+0.01% TFA) and MeCN (+0.01% TFA) as eluents (column C18). The pooled product fractions were lyophilized and the product was obtained as a white solid. MS (ES) $C_{35}H_{40}N_4O_5$ requires: 596.72, found: 597. $^1$H-NMR (300 MHz, DMSO-d$_6$) δ: 10.69 (0.3 H, s). 10.62 (0.7 H, s), 8.38 (0.7 H, s), 8.29 (0.3 H, s), 7.99 (0.7H, d, J=5.7 Hz), 7.96 (0.3 H, d, J=4 Hz), 7.80 (1 H, d, J=6.3 Hz), 7.70 (1 H, t, J=5.6 Hz), 7.65-7.64 (1 H, m), 7.51-7.47 (1 H, m), 7.08 (1 H, d, 6.6 Hz), 6.99 (1 H, s), 6.58 (1 H, dd, J=6.3 Hz, J=1.5 Hz), 5.90-5.86 (0.7 H, m), 5.33-5.30 (0.3 H, m), 4.14 (3 H, s), 3.90-3.71 (m, 2 H), 3.67 (2.1 H), 3.66 (0.9 H), 2.90 (2.1 H, s), 2.73 (0.9 H, s), 2.40-2.27 (7 H, m), 1.87-1.75 (4 H, m), 1.34-1.76 (4 H, m), 0.90 (3 H, t, J=5.4 Hz).

Example 6

(S)-1-methyl-N-(7-oxo-1-(5-(2-oxo-1,2-dihydroquinolin-3-yl)oxazol-2-yl)nonyl)azetidine-3-carboxamide (Compound 44)

A solution of (S)-N-(1-(5-(2-methoxyquinolin-3-yl)oxazol-2-yl)-7-oxononyl)-1-methylazetidine-3-carboxamide (0.05 mmol, 1 eq), prepared as described above, in DCM (1 mL) was treated with 0.2 mL of HCl 4N in dioxane. The mixture was stirred 1 h at room temperatures, then concentrated and purified by RP-HPLC using water (+0.01% TFA) and MeCN (+0.01% TFA) as eluents (column C18). The pooled product fractions were lyophilized and the product was obtained as a white solid. MS (ES) $C_{26}H_{32}N_4O_4$ requires: 464.58, found: 465. $^1$H-NMR (400 MHz, DMSO-$d_6$) δ: 12.21 (1 H, s), 9.83 (1 H, bs), 8.89-8.82 (1 H, m), 8.26 (1 H, s), 7.83 (1 H, d, J=7.6 Hz), 7.78 (1 H, s), 7.55 (1 H, t, J=7.2 Hz), 7.38 (1 H, d, J=8.4 Hz), 7.25 (1 H, t, J=7.6 Hz), 5.09 (1 H, bs), 4.36 (1 H, bs), 4.22-4.20 (1 H, m), 4.11 (1 H, bs), 3.98-3.92 (1 H, m), 3.57-3.55 (1 H, m, partially overlaps with water), 2.82 (3 H, s), 2.42-2.37 (4 H, m), 1.96-1.92 (1 H, m), 1.83-1.80 (1 H, m), 1.48-1.44 (2 H, m), 1.35-1.33 (4 H, m), 0.89 (3 H, t, J=7.2 Hz).

Example 7

(S)-1-methyl-N-(1-(5-(1-methyl-2-oxo-1,2-dihydroquinolin-3-yl)oxazol-2-yl)-7-oxononyl)azetidine-3-carboxamide (Compound 92)

Step 1: tert-butyl(2-(1-methyl-2-oxo-1,2-dihydroquinolin-3-yl)-2-oxoethyl)carbamate To a 0.3 M solution of 3-bromo-1-methylquinolin-2(1 H)-one (1 equiv; prepared as described in Tetrahedron, 64 (26), 6030-6037; 2008) and tert-butyl(2-(methoxy(methyl)amino)-2-oxoethyl)carbamate (1.2 eq) in dry THF, isopropylmagnesium chloride (3 eq) was added dropwise at room temperature. The mixture was stirred for 30 min at room temperature, diluted with dichloromethane, washed with sat. aq. NH$_4$Cl dried (Na$_2$SO$_4$) and concentrated under reduced pressure. The residue was purified by flash chromatography (SiO$_2$, Pethroleum ether/EtOAc, from 7% to 60% EtOAc). The pooled fractions were concentraded under vacuum to the title compound. MS (ES) $C_{17}H_{20}N_2O_4$ requires: 316.35, found: 317. $^1$H-NMR (400 MHz, DMSO-$d_6$) δ: 8.53 (1 H, s), 7.99 (1 H, d, J=7.2 Hz), 7.78 (1 H, t, J=6.8 Hz), 7.61 (1 H, d, J=8.4 Hz), 7.35 (1 H, t, J=7.2 Hz), 6.97 (1 H, bt, J=5.6 Hz), 4.45 (1 H, d, J=5.6 Hz), 3.70 (3 H, s), 1.39 (9 H, s).

Step 2: 3-(2-aminoacetyl)-1-methylquinolin-2(1 H)-one

The compound from the previous step was solubilized in a 1:1 mixture of dichloromethane and trifluoroacetic acid at room temperature. The mixture was stirred 30 min, evaporated under vacuum and the product was used directly in the next step. MS (ES) $C_{12}H_{12}N_2O_2$ requires: 216.24, found: 217.

Step 3: (S)-tert-butyl(1-((2-(1-methyl-2-oxo-1,2-dihydroquinolin-3-yl)-2-oxoethyl)amino)-1,8-dioxodecan-2-yl)carbamate A solution of (S)-2-((tert-butoxycarbonyl)amino)-8-oxodecanoic acid (0.76 mmol, 1 eq; prepared as described in J. Med. Chem. 2008, 51(8), pp 2350-2353), EDC.HCl (1 eq), HOBT (1 eq) in DMF (0.2 M) was stirred at room temperature for 10 min. 3-(2-aminoacetyl)-1-methylquinolin-2(1 H)-one (1.1 eq) in DMF (3 eq) was subsequently added, followed by DIPEA (2.2 eq) and the mixture was stirred at room temperature for 2 h. The mixture was diluted with DCM and washed with brine. The organic phase was dried (Na$_2$SO$_4$), filtered and concentrated. The residue was purified by flash chromatography (SiO$_2$, Petroleum ether/EtOAc, from 10% EtOAc to 80% EtOAc), to give the title compound as an oil. MS (ES) $C_{27}H_{37}N_3O_6$ requires: 499.60, found: 500.

Step 4: (S)-tert-butyl(1-(5-(1-methyl-2-oxo-1,2-dihydroquinolin-3-yl)oxazol-2-yl)-7-oxononyl)carbamate PPh$_3$ (2 eq) and C$_2$Cl$_6$ (2 eq) were dissolved in DCM (0.2 M solution) at room temperature and Et$_3$N was added (4 eq), followed after 15 min of stirring by dropwise addition of a solution of the amide from the previous step (1 eq) in DCM. The mixture was stirred overnight at room temperature and was then diluted with AcOEt and washed with brine. The organic phase was separated, dried (Na$_2$SO$_4$), filtered and concentrated under reduced pressure. The crude product was purified by flash chromatography on SiO$_2$ (Petroleum ether/EtOAc, from 10% EtOAc to 100% EtOAc), to afford the title product. MS (ES) $C_{27}H_{35}N_3O_5$ requires: 481.58, found: 482.

Step 5: (S)-3-(2-(1-amino-7-oxononyl)oxazol-5-yl)-1-methylquinolin-2(1 H)-one

Compound from the previous step was dissolved in a mixture DCM: TFA (1:1) and stirred at 0° C. for 10 min then at room temperature for 1 h. The mixture was diluted with toluene (7 mL) and the solvent evaporated. The resulting oil was diluted with EtOAc and washed with sat. aq. NaHCO$_3$ solution, dried (Na$_2$SO$_4$), filtered and concentrated under reduced pressure. The crude product so obtained was used directly in the following step. MS (ES) $C_{22}H_{27}N_3O_3$ requires: 381.47, found: 382.

Step 6: (S)-tert-butyl 3-((1-(5-(1-methyl-2-oxo-1,2-dihydroquinolin-3-yl)oxazol-2-yl)-7-oxononyl)carbamoyl)azetidine-1-carboxylate A solution of 1-(tert-butoxycarbonyl)azetidine-3-carboxylic acid (1.3 eq), HOBt (1.3 eq) and EDC.HCl (1.3 eq) in DMF (premixed for 10 min) was added to S)-3-(2-(1-amino-7-oxononyl)oxazol-5-yl)-1-methylquinolin-2(1 H)-one (1 eq), obtained as described above. The mixture was stirred o/n at room temperature. The reaction mixture was diluted with DCM, washed with sat. aq. NaHCO$_3$ solution, brine, dried (Na$_2$SO$_4$), filtered and concentrated. The mixture was purified by flash chromatography on silica, eluting with EtOAc/petroleum ether (from 50% of EtOAc to 100% of EtOAc). MS (ES) $C_{31}H_{40}N_4O_6$ requires: 564.67, found: 565.

Step 7: (S)-N-(1-(5-(1-methyl-2-oxo-1,2-dihydroquinolin-3-yl)oxazol-2-yl)-7-oxononyl)azetidine-3-carboxamide The compound from the previous step was treated with DCM:TFA (7:3) at 0° C. The mixture was stirred at 0° C. for 30 min, diluted with Et₂O and evaporated under vacuum. The residue was dissolved with EtOAc and washed with sat. aq. NaHCO₃ solution, dried (Na₂SO₄), filtered and concentrated. Product was used directly in the next step. MS (ES) $C_{26}H_{32}N_4O_4$ requires: 464.56, found: 465.

Step 8: (S)-1-methyl-N-(1-(5-(1-methyl-2-oxo-1,2-dihydroquinolin-3-yl)oxazol-2-yl)-7-oxononyl)azetidine-3-carboxamide A 0.2 M methanolic solution of the compound from the previous step (1 eq) and formaldehyde (3.5 eq, 37% aq. solution) was stirred for 10 minutes at room temperature. NaOAc (3.0 eq) and NaBH₃CN (3.0 eq) were added and the resulting mixture was stirred for 1 h at room temperature. The solvent was removed under reduced pressure, dissolved in acetonitrile and purified by RP-HPLC (acetonitrile/H₂O+0.01% TFA). The product was isolated as a TFA salt. MS (ES) $C_{27}H_{34}N_4O_4$ requires: 478.58, found: 479. ¹H-NMR (400 MHz, DMSO-d₆) δ: 8.23 (1 H, s), 7.87 (1 H, s), 7.80 (1 H, d, J=7.6 Hz), 7.67 (1 H, t, J=7.6 Hz), 7.54 (1 H, d, J=8.4 Hz), 7.34 (1 H, t, J=7.6 Hz), 7.28 (1 H, bs), 5.19-5.13 (1 H, m), 4.49-4.30 (2 H, m), 4.15-4.12 (2 H, m), 3.78 (3H, s), 3.69-3.64 (1 H, m), 2.85 (3 H, s), 2.42-2.40 (4 H, m), 1.56-1.52 (2 H, m), 1.38-1.33 (6 H, m), 0.97 (3 H, t, J=7.2 Hz).

Example 8

(S)-N-(1-(5-(1-methyl-2-oxo-1,2-dihydroquinolin-3-yl)oxazol-2-yl)-7-oxononyl)thiazole-5-carboxamide (Compound 112)

(S)-3-(2-(1-amino-7-oxononyl)oxazol-5-yl)-1-methylquinolin-2(1H)-one (1 eq), prepared as described in steps 1 to 5 of Example 7, was treated with a solution of thiazole-5-carboxylic acid (1.3 eq), HOBT (1.3 eq) and EDC.HCl (1.3 eq) in DMF (premixed for 3 min), followed by DIPEA (1.3 eq). The mixture was stirred at room temperature for 2 h and the desired product was isolated by preparative RP-HPLC, using water (+0.01% TFA) and MeCN (+0.01% TFA) as eluents (column C18). The pooled product fractions were lyophilized and the product was obtained as a white solid. MS (ES) $C_{26}H_{28}N_4O_4S$ requires: 492.59, found: 493. ¹H-NMR (400 MHz, DMSO-d₆) δ: 9.28 (1 H, d, J=8 Hz), 9.26 (1 H, s), 8.62 (1 H, s), 8.29 (1 H, s), 7.91 (1 H, d, J=7.6 Hz), 7.84 (1 H, s), 7.68 (1 H, t, J=7.2 Hz), 7.61 (1 H, d, J=8.2 Hz), 7.34 (1 H, t, J=7.6 Hz), 5.27-5.22 (1 H, m), 3.75 (3 H, s), 2.39-2.36 (4 H, m), 2.09-2.06 (1 H, m), 2.00-1.96 (1H, m), 1.50-1.27 (6 H, m), 0.89 (3 H, t, J=7.2 Hz).

The following compounds (Table 1) were prepared according to the procedures described in Examples 1 to 8.

TABLE 1

| Cpd | Compound Name | Structure | Molecular Ion [M + H]⁺ | Procedure |
|---|---|---|---|---|
| 1 | (S)-2-(5-methoxy-2-methyl-1H-indol-3-yl)-N-(1-(5-(2-methoxyquinolin-3-yl)oxazol-2-yl)-7-oxononyl)acetamide | 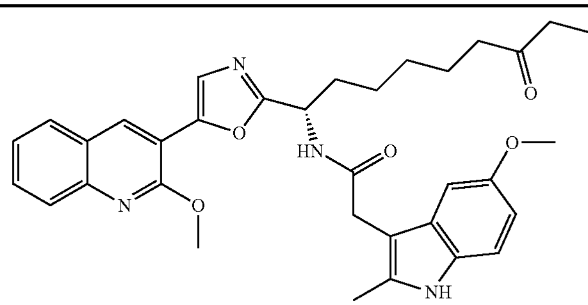 | 583 | Example 1 |
| 2 | (S)-N-(1-(5-(2-methoxyquinolin-3-yl)oxazol-2-yl)-7-oxononyl)-1-methylazetidine-3-carboxamide | 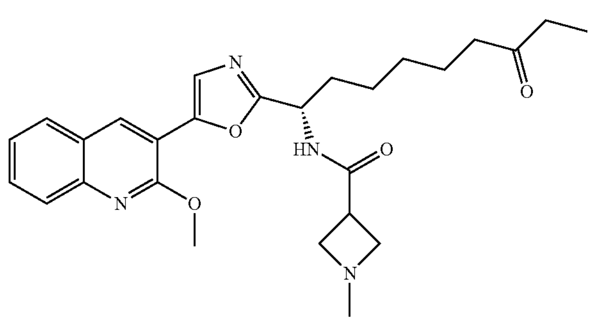 [SMILES: CCC(=O)CCCCC[C@H](NC(=O)C1CN(C)C1)c1ncc(-c2cc3ccccc3nc2OC)o1] | 479 | Example 2 |
| 3 | (S)-1-methyl-N-(7-oxo-1-(5-phenyloxazol-2-yl)nonyl)piperidine-4-carboxamide | 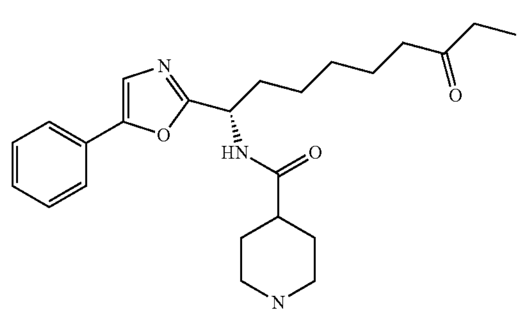 [SMILES: CCC(=O)CCCCC[C@H](NC(=O)C1CCNCC1)c1ncc(-c2ccccc2)o1] | 426 | Example 2 |

TABLE 1-continued

| Cpd | Compound Name | Structure | Molecular Ion [M + H]+ | Procedure |
|---|---|---|---|---|
| 4 | (S)-2-(5-methoxy-2-methyl-1H-indol-3-yl)-N-(7-oxo-1-(5-phenyloxazol-2-yl)nonyl)acetamide | 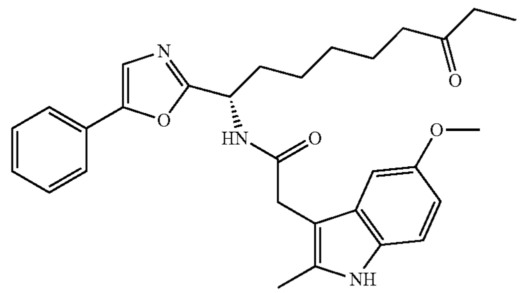 [SMILES: CCC(=O)CCCCC[C@H](NC(=O)Cc1c(C)[nH]c2ccc(OC)cc12)c1ncc(-c2ccccc2)o1] | 502 | Example 1 |
| 5 | ((S)-N-(1-(5-(2,3-dihydrobenzo[b][1,4]dioxin-5-yl)oxazol-2-yl)-7-oxononyl)-1-methylpiperidine-4-carboxamide | 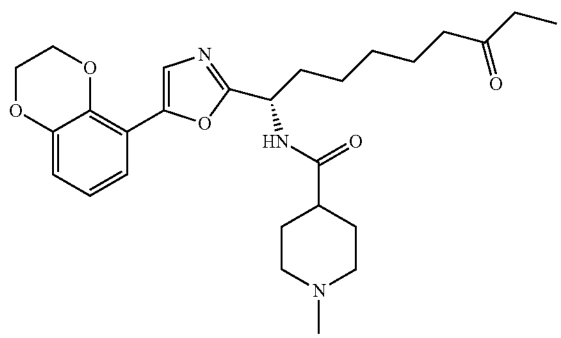 [SMILES: CCC(=O)CCCCC[C@H](NC(=O)C1CCN(C)CC1)c1ncc(-c2cccc3c2OCCO3)o1] | 484 | Example 1 |
| 6 | (S)-N-(7-oxo-1-(5-phenyloxazol-2-yl)nonyl)thiazole-5-carboxamide | 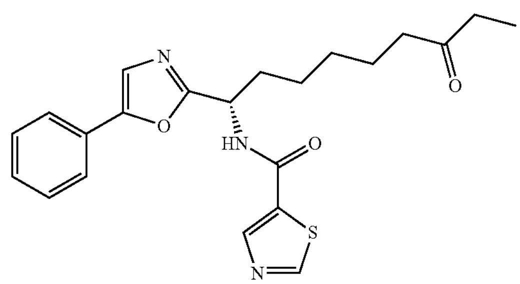 [SMILES: CCC(=O)CCCCC[C@H](NC(=O)c1cncs1)c1ncc(-c2ccccc2)o1] | 412 | Example 1 |
| 7 | (S)-3-(dimethylamino)-N-(7-oxo-1-(5-phenyloxazol-2-yl)nonyl)propanamide | 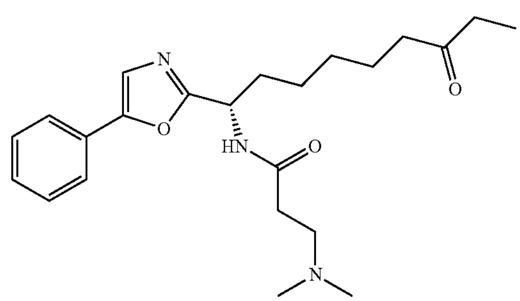 [SMILES: CCC(=O)CCCCC[C@H](NC(=O)CCN(C)C)c1ncc(-c2ccccc2)o1] | 400 | Example 1 |
| 8 | 1-methyl-N-((S)-7-oxo-1-(5-phenyloxazol-2-yl)nonyl)pyrrolidine-3-carboxamide | 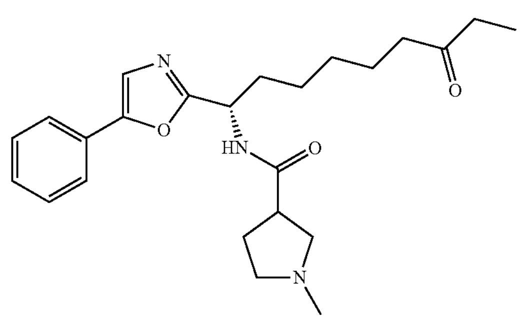 [SMILES: CCC(=O)CCCCC[C@H](NC(=O)C1CCN(C)C1)c1ncc(-c2ccccc2)o1] | 412 | Example 2 |

TABLE 1-continued

| Cpd | Compound Name | Structure | Molecular Ion [M + H]+ | Procedure |
|---|---|---|---|---|
| 9 | (S)-2-(dimethylamino)-2-methyl-N-(7-oxo-1-(5-phenyloxazol-2-yl)nonyl)propanamide | 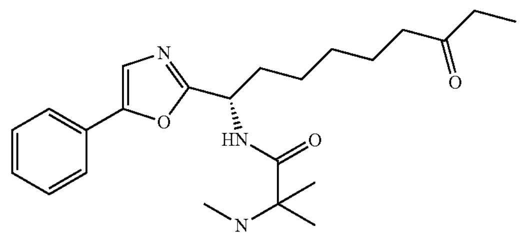 [SMILES: CCC(=O)CCCCC[C@H](NC(=O)C(C)(C)NC)c1ncc(-c2ccccc2)o1] | 414 | Example 1 |
| 10 | (S)-N-(7-oxo-1-(5-phenyloxazol-2-yl)nonyl)cyclopropane-1,1-dicarboxamide | 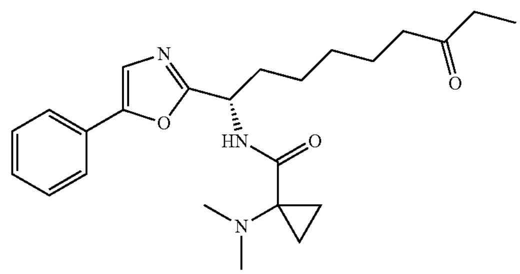 [SMILES: CCC(=O)CCCCC[C@H](NC(=O)C1(N(C)C)CC1)c1ncc(-c2ccccc2)o1] | 412 | Example 1 |
| 11 | (S)-2-(methylsulfonyl)-N-(7-oxo-1-(5-phenyloxazol-2-yl)nonyl)acetamide | 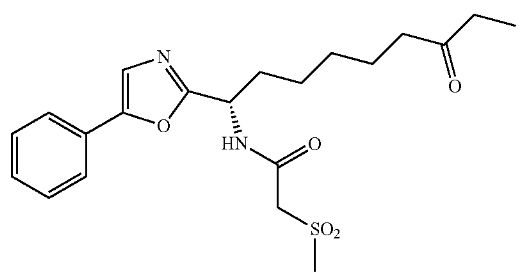 [SMILES: CCC(=O)CCCCC[C@H](NC(=O)CS(C)(=O)=O)c1ncc(-c2ccccc2)o1] | 421 | Example 1 |
| 12 | ((S)-2-cyclohexyl-N-(7-oxo-1-(5-phenyloxazol-2-yl)nonyl)acetamide | 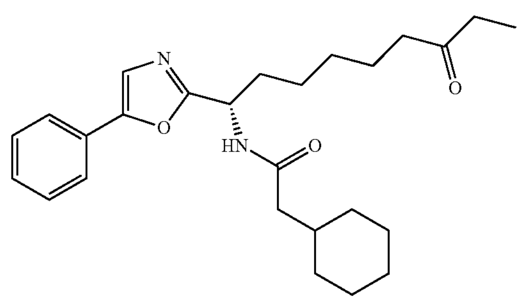 [SMILES: CCC(=O)CCCCC[C@H](NC(=O)CC1CCCCC1)c1ncc(-c2ccccc2)o1] | 425 | Example 1 |
| 13 | (R)-2-oxo-N-((S)-7-oxo-1-(5-phenyloxazol-2-yl)nonyl)thiazolidine-4-carboxamide | 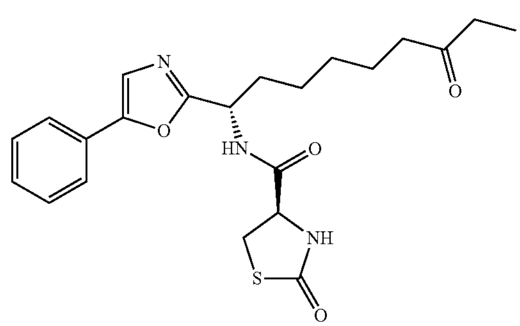 [SMILES: CCC(=O)CCCCC[C@H](NC(=O)[C@@H]1CSC(=O)N1)c1ncc(-c2ccccc2)o1] | 430 | Example 1 |

TABLE 1-continued

| Cpd | Compound Name | Structure | Molecular Ion [M + H]+ | Procedure |
|---|---|---|---|---|
| 14 | (S)-2-chloro-N-(7-oxo-1-(5-phenyloxazol-2-yl)nonyl)isonicotinamide | 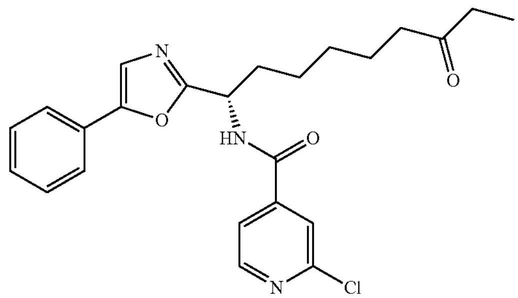 [SMILES: CCC(=O)CCCCC[C@H](NC(=O)c1ccnc(Cl)c1)c1ncc(-c2ccccc2)o1] | 440 | Example 1 |
| 15 | (S)-2-(4-methylpiperazin-1-yl)-N-(7-oxo-1-(5-phenyloxazol-2-yl)nonyl)acetamide | 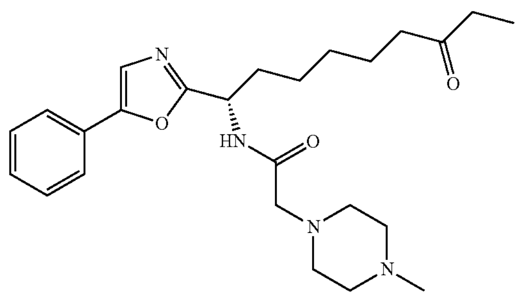 [SMILES: CCC(=O)CCCCC[C@H](NC(=O)CN1CCN(C)CC1)c1ncc(-c2ccccc2)o1] | 441 | Example 1 |
| 16 | (S)-N-(7-oxo-1-(5-phenyloxazol-2-yl)nonyl)quinoxaline-6-carboxamide | 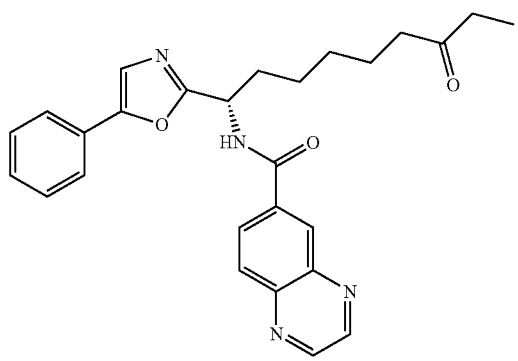 [SMILES: CCC(=O)CCCCC[C@H](NC(=O)c1ccc2nccnc2c1)c1ncc(-c2ccccc2)o1] | 457 | Example 1 |
| 17 | 1-methyl-N-((S)-7-oxo-1-(5-phenyloxazol-2-yl)nonyl)piperidine-3-carboxamide | 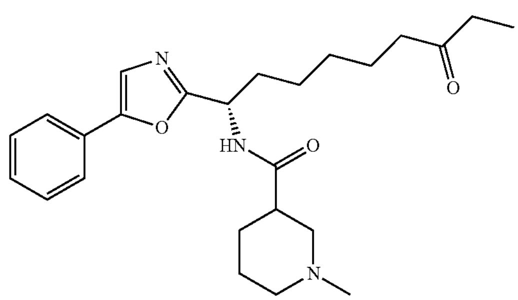 [SMILES: CCC(=O)CCCCC[C@H](NC(=O)C1CCCN(C)C1)c1ncc(-c2ccccc2)o1] | 426 | Example 2 |
| 18 | (S)-2-(2-methyl-1H-benzo[d]imidazol-1-yl)-N-(7-oxo-1-(5-phenyloxazol-2-yl)nonyl)acetamide | 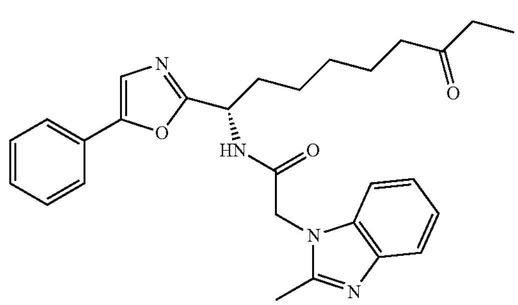 [SMILES: CCC(=O)CCCCC[C@H](NC(=O)Cn1c(C)nc2ccccc21)c1ncc(-c2ccccc2)o1] | 473 | Example 1 |

TABLE 1-continued

| Cpd | Compound Name | Structure | Molecular Ion [M + H]+ | Procedure |
|---|---|---|---|---|
| 19 | (S)-6-chloro-N-(7-oxo-1-(5-phenyloxazol-2-yl)nonyl)imidazo[1,2-b]pyridazine-2-carboxamide | 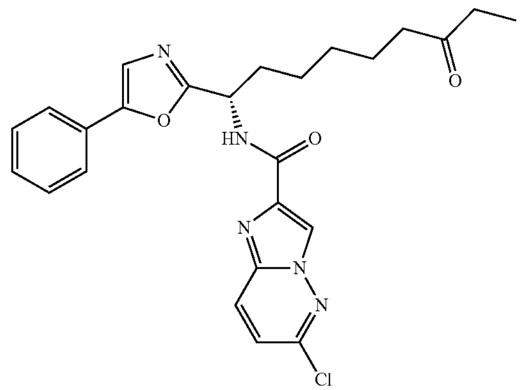 [SMILES: CCC(=O)CCCCC[C@H](NC(=O)c1cn2nc(Cl)ccc2n1)c1ncc(-c2ccccc2)o1] | 480 | Example 1 |
| 20 | (S)-N-(7-oxo-1-(5-phenyloxazol-2-yl)nonyl)-1H-indole-6-carboxamide | 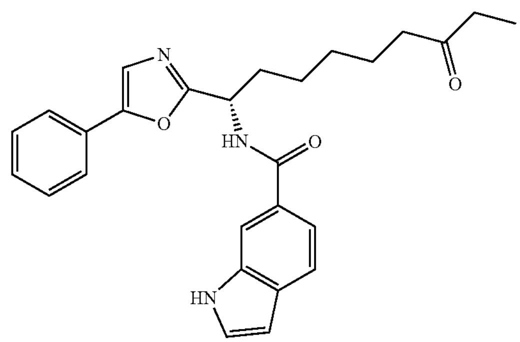 [SMILES: CCC(=O)CCCCC[C@H](NC(=O)c1ccc2cc[nH]c2c1)c1ncc(-c2ccccc2)o1] | 444 | Example 1 |
| 21 | 1-methyl-N-((S)-7-oxo-1-(5-phenyloxazol-2-yl)nonyl)azepane-2-carboxamide | 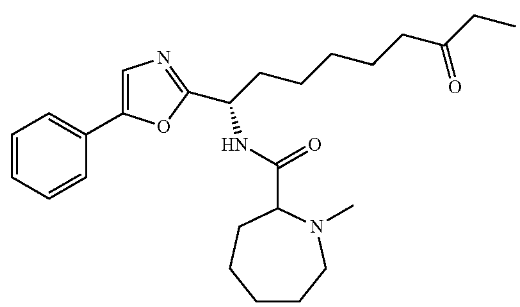 [SMILES: CCC(=O)CCCCC[C@H](NC(=O)C1CCCCCN1C)c1ncc(-c2ccccc2)o1] | 440 | Example 2 |
| 22 | (S)-N-(7-oxo-1-(5-phenyloxazol-2-yl)nonyl)-4-sulfamoylbutanamide | 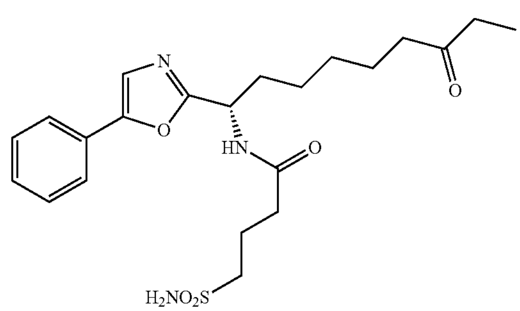 [SMILES: CCC(=O)CCCCC[C@H](NC(=O)CCCS(N)(=O)=O)c1ncc(-c2ccccc2)o1] | 450 | Example 1 |

TABLE 1-continued

| Cpd | Compound Name | Structure | Molecular Ion [M + H]+ | Procedure |
|---|---|---|---|---|
| 23 | 2-methyl-N-((S)-7-oxo-1-(5-phenyloxazol-2-yl)nonyl)tetrahydrofuran-2-carboxamide | 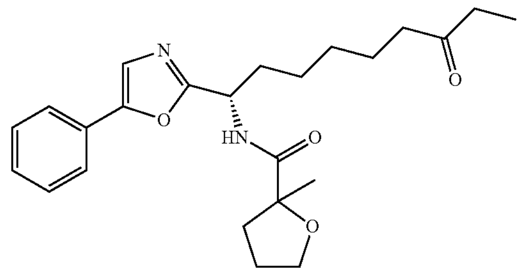 [SMILES: CCC(=O)CCCCC[C@H](NC(=O)C1(C)CCCO1)c1ncc(-c2ccccc2)o1] | 413 | Example 1 |
| 24 | (S)-3,3-difluoro-N-(7-oxo-1-(5-phenyloxazol-2-yl)nonyl)cyclobutanecarboxamide | 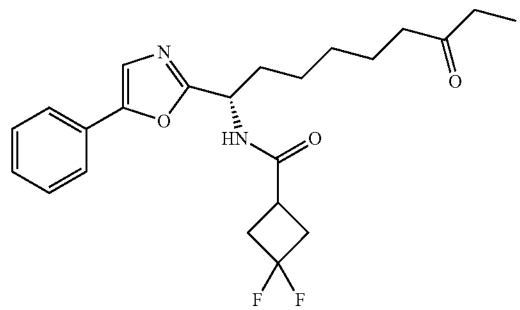 [SMILES: CCC(=O)CCCCC[C@H](NC(=O)C1CC(F)(F)C1)c1ncc(-c2ccccc2)o1] | 419 | Example 1 |
| 25 | 3-(1-methylpiperidin-3-yl)-N-((S)-7-oxo-1-(5-phenyloxazol-2-yl)nonyl)propanamide | 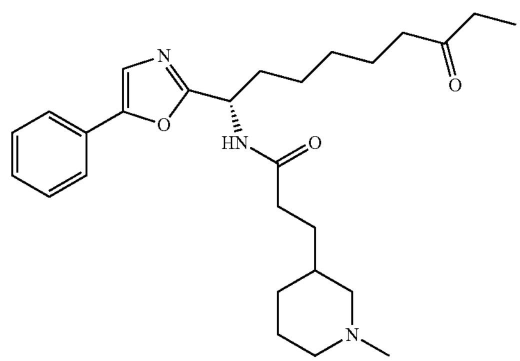 [SMILES: CCC(=O)CCCCC[C@H](NC(=O)CCC1CCCN(C)C1)c1ncc(-c2ccccc2)o1] | 454 | Example 1 |
| 26 | (S)-3-(2-ethyl-1H-benzo[d]imidazol-1-yl)-N-(7-oxo-1-(5-phenyloxazol-2-yl)nonyl)propanamide | 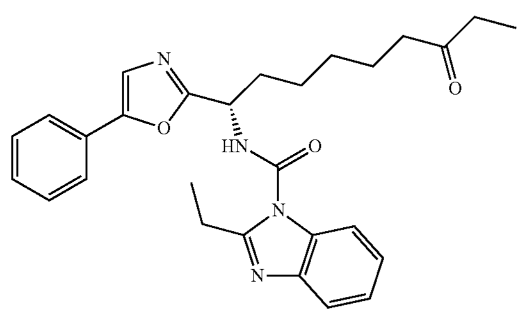 [SMILES: CCC(=O)CCCCC[C@H](NC(=O)n1c(CC)nc2ccccc21)c1ncc(-c2ccccc2)o1] | 501 | Example 1 |
| 27 | (S)-N1,N1-dimethyl-N2-(7-oxo-1-(5-phenyloxazol-2-yl)nonyl)oxalamide | 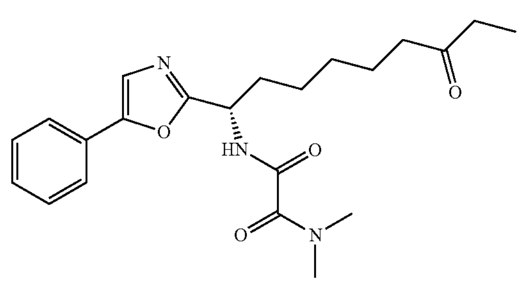 [SMILES: CCC(=O)CCCCC[C@H](NC(=O)C(=O)N(C)C)c1ncc(-c2ccccc2)o1] | 400 | Example 1 |

TABLE 1-continued

| Cpd | Compound Name | Structure | Molecular Ion [M + H]+ | Procedure |
|---|---|---|---|---|
| 28 | (S)-2-(4-methylpiperazin-1-yl)-2-oxo-N-(7-oxo-1-(5-phenyloxazol-2-yl)nonyl)acetamide | 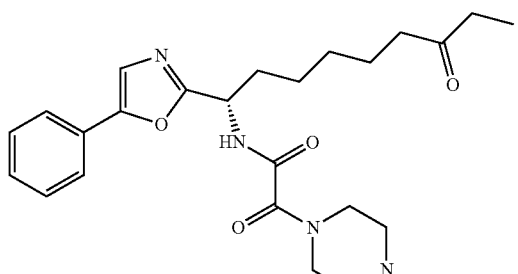 | 455 | Example 1 |
| 29 | (S)-3-(2-ethyl-1H-benzo[d]imidazol-1-yl)-N-(1-(5-(2-methoxyquinolin-3-yl)oxazol-2-yl)-7-oxononyl)propanamide | 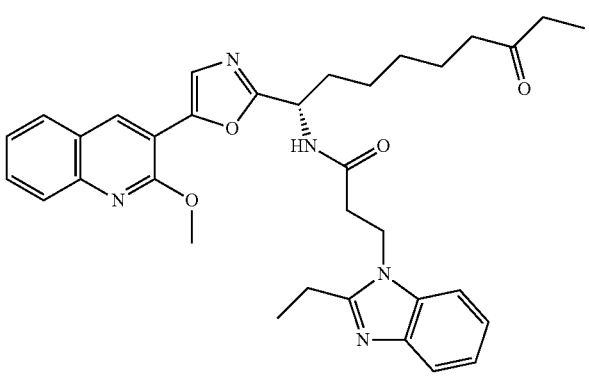 [SMILES: CCC(=O)CCCCC[C@H](NC(=O)CCn1c(CC)nc2ccccc21)c1ncc(-c2cc3ccccc3nc2OC)o1] | 582 | Example 1 |
| 30 | (S)-4-methyl-N-(7-oxo-1-(5-phenyloxazol-2-yl)nonyl)-3,4-dihydro-2H-benzo[b][1,4]oxazine-7-carboxamide | 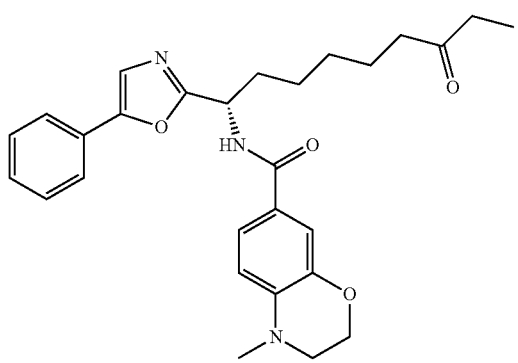 [SMILES: CCC(=O)CCCCC[C@H](NC(=O)c1ccc2c(c1)OCCN2C)c1ncc(-c2ccccc2)o1] | 476 | Example 1 |
| 31 | (S)-2-(imidazo[2,1-b]thiazol-3-yl)-N-(7-oxo-1-(5-phenyloxazol-2-yl)nonyl)acetamide | 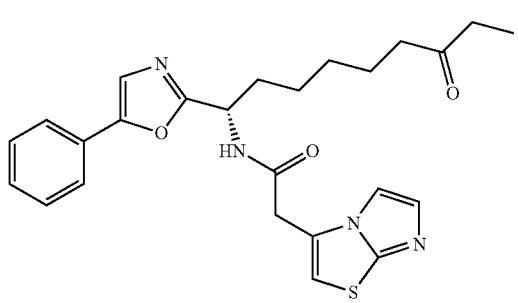 [SMILES: CCC(=O)CCCCC[C@H](NC(=O)Cc1csc2nccn12)c1ncc(-c2ccccc2)o1] | 465 | Example 1 |

TABLE 1-continued

| Cpd | Compound Name | Structure | Molecular Ion [M + H]+ | Procedure |
|---|---|---|---|---|
| 32 | (S)-1-methyl-N-(7-oxo-1-(5-phenyloxazol-2-yl)nonyl)azetidine-3-carboxamide | 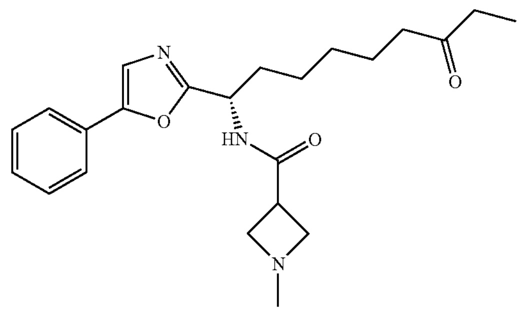 [SMILES: CCC(=O)CCCCC[C@H](NC(=O)C1CN(C)C1)c1ncc(-c2ccccc2)o1] | 398 | Example 2 |
| 33 | (S)-2-(2-aminothiazol-4-yl)-N-(7-oxo-1-(5-phenyloxazol-2-yl)nonyl)acetamide | 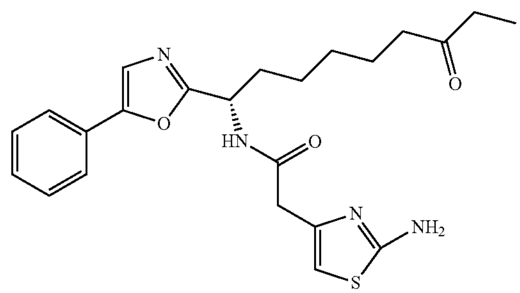 [SMILES: CCC(=O)CCCCC[C@H](NC(=O)Cc1csc(N)n1)c1ncc(-c2ccccc2)o1] | 441 | Example 1 |
| 34 | N-((S)-1-(5-(2-methoxyquinolin-3-yl)oxazol-2-yl)-7-oxononyl)-1-methypyrrolidine-3-carboxamide | 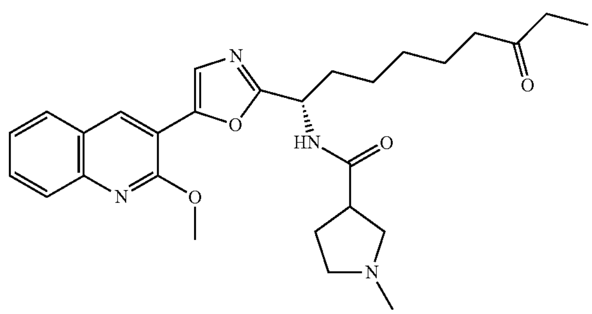 [SMILES: CCC(=O)CCCCC[C@H](NC(=O)C1CCN(C)C1)c1ncc(-c2cc3ccccc3nc2OC)o1] | 493 | Example 2 |
| 35 | (S)-2-(dimethylamino)-N-(1-(5-(2-methoxyquinolin-3-yl)oxazol-2-yl)-7-oxononyl)-2-methylpropanamide | 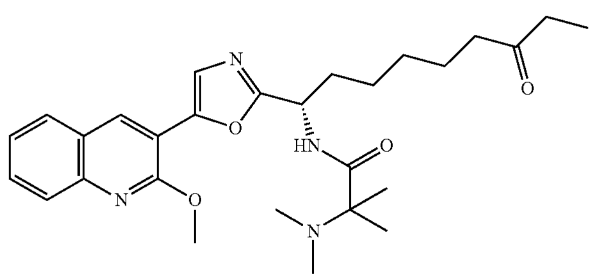 [SMILES: CCC(=O)CCCCC[C@H](NC(=O)C(C)(C)N(C)C)c1ncc(-c2cc3ccccc3nc2OC)o1] | 495 | Example 1 |
| 36 | (S)-N1-(1-(5-(2-methoxyquinolin-3-yl)oxazol-2-yl)-7-oxononyl)-N2,N2-dimethyloxalamide | 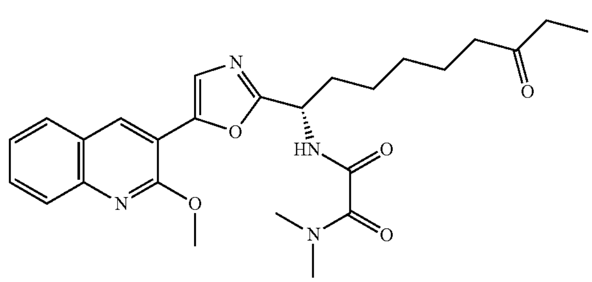 [SMILES: CCC(=O)CCCCC[C@H](NC(=O)C(=O)N(C)C)c1ncc(-c2cc3ccccc3nc2OC)o1] | 481 | Example 1 |

TABLE 1-continued

| Cpd | Compound Name | Structure | Molecular Ion [M + H]+ | Procedure |
|---|---|---|---|---|
| 37 | (S)-N-(1-(5-(2-methoxyquinolin-3-yl)oxazol-2-yl)-7-oxononyl)-2-(4-methylpiperazin-1-yl)-2-oxoacetamide | 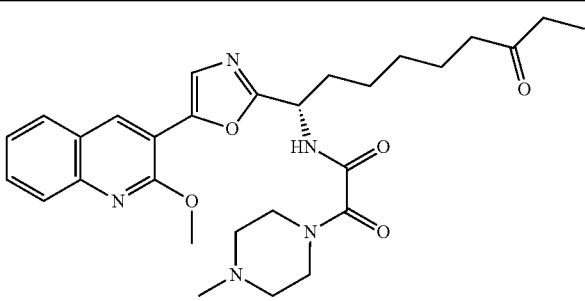 | 536 | Example 1 |
| 38 | (S)-3-(dimethylamino)-N-(1-(5-(2-methoxyquinolin-3-yl)oxazol-2-yl)-7-oxononyl)propanamide | 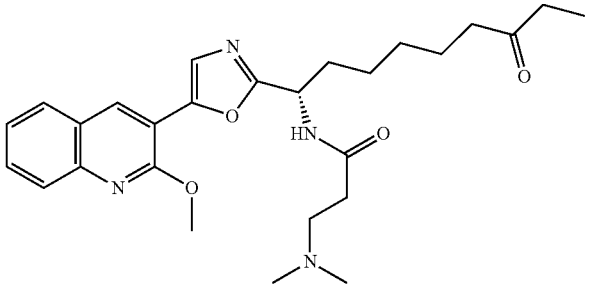 [SMILES: CCC(=O)CCCCC[C@H](NC(=O)CCN(C)C)c1ncc(-c2cc3ccccc3nc2OC)o1] | 481 | Example 1 |
| 39 | (S)-9-((2-(dimethylamino)ethyl)amino)-9-(5-(2-methoxyquinolin-3-yl)oxazol-2-yl)nonan-3-one | 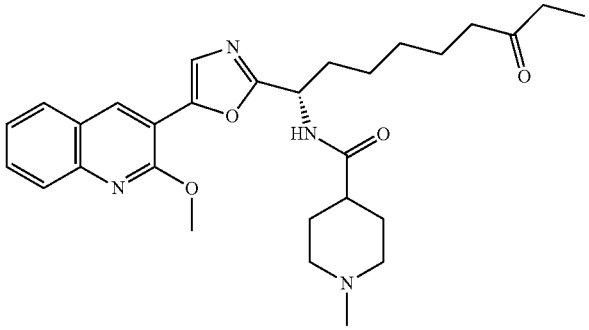 [SMILES: CCC(=O)CCCCC[C@H](NC(=O)C1CCN(C)CC1)c1ncc(-c2cc3ccccc3nc2OC)o1] | 507 | Example 2 |
| 40 | (S)-N-(1-(5-(2-methoxyquinolin-3-yl)oxazol-2-yl)-7-oxononyl)thiazole-5-carboxamide | 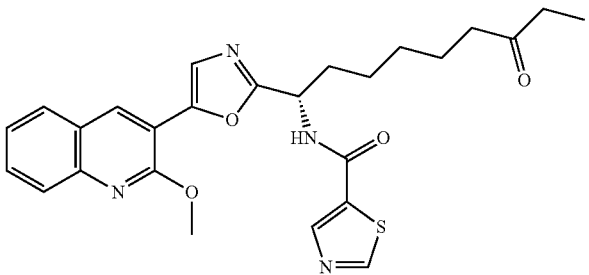 | 493 | Example 1 |
| 41 | (S)-N-(1-(5-(2-methoxyquinolin-3-yl)oxazol-2-yl)-7-oxononyl)quinuclidine-4-carboxamide | 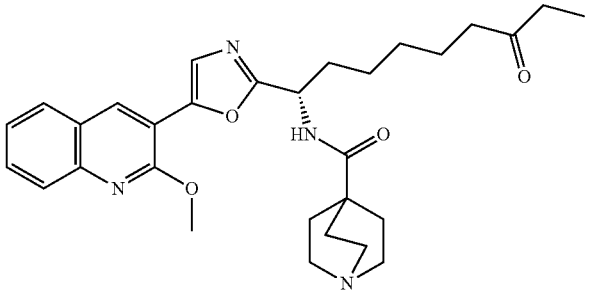 [SMILES: CCC(=O)CCCCC[C@H](NC(=O)C12CCN(CC1)CC2)c1ncc(-c2cc3ccccc3nc2OC)o1] | 519 | Example 1 |

TABLE 1-continued

| Cpd | Compound Name | Structure | Molecular Ion [M + H]+ | Procedure |
|---|---|---|---|---|
| 42 | (R)-N-(1-(5-(2-methoxyquinolin-3-yl)oxazol-2-yl)-7-oxononyl)-1-methylazetidine-3-carboxamide | 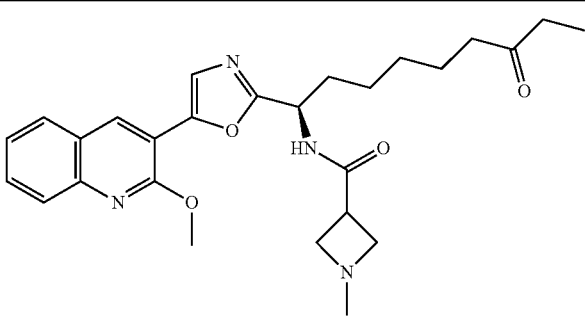 | 479 | Example 2 |
| 43 | (S)-2-(5-methoxy-2-methyl-1H-indol-3-yl)-N-(1-(5-(2-methoxyquinolin-3-yl)oxazol-2-yl)-7-oxononyl)-N-methylacetamide | 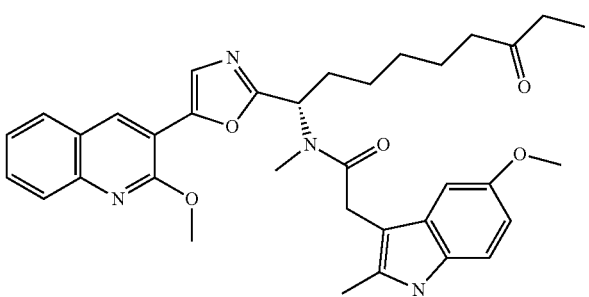 | 597 | Example 5 |
| 44 | (S)-1-methyl-N-(7-oxo-1-(5-(2-oxo-1,2-dihydroquinolin-3-yl)oxazol-2-yl)nonyl)azetidine-3-carboxamide | 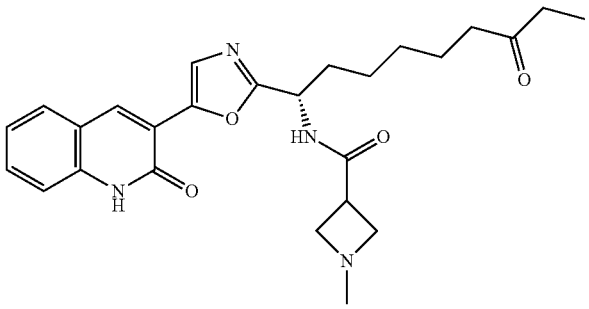 [SMILES: CCC(=O)CCCCC[C@H](NC(=O)C1CN(C)C1)c1ncc(-c2cc3ccccc3[nH]c2=O)o1] | 465 | Example 6 |
| 45 | (S)-N1-(1-(5-(2-methoxyquinolin-3-yl)-1,3,4-oxadiazol-2-yl)-7-oxononyl)-N2,N2-dimethyloxalamide | 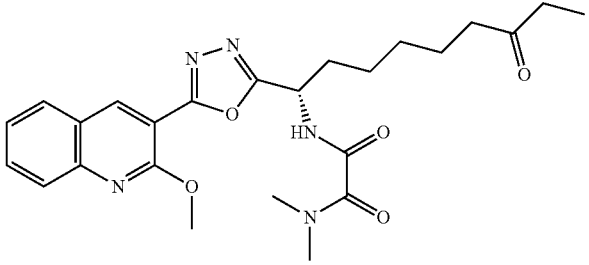 [SMILES: CCC(=O)CCCCC[C@H](NC(=O)C(=O)N(C)C)c1nnc(-c2cc3ccccc3nc2OC)o1] | 482 | Example 4 |
| 46 | (S)-N-(1-(5-(2-methoxyquinolin-3-yl)-1,3,4-oxadiazol-2-yl)-7-oxononyl)-2-(4-methylpiperazin-1-yl)-2-oxoacetamide | 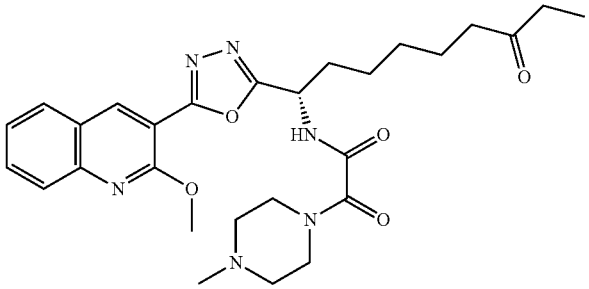 [SMILES: CCC(=O)CCCCC[C@H](NC(=O)C(=O)N1CCN(C)CC1)c1nnc(-c2cc3ccccc3nc2OC)o1] | 537 | Example 4 |

TABLE 1-continued

| Cpd | Compound Name | Structure | Molecular Ion [M + H]+ | Procedure |
|---|---|---|---|---|
| 47 | (S)-N-(1-(5-(2-methoxyquinolin-3-yl)-1,3,4-oxadiazol-2-yl)-7-oxononyl)-1-methylpiperidine-4-carboxamide | 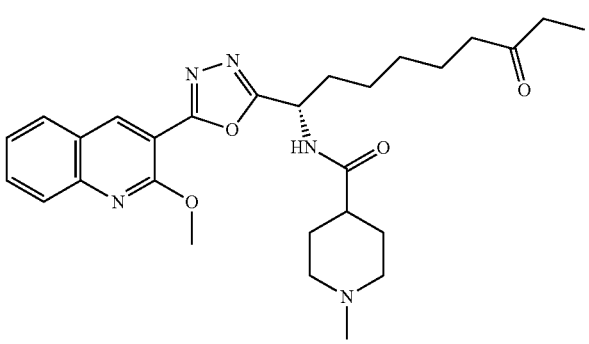 [SMILES: CCC(=O)CCCCC[C@H](NC(=O)C1CCN(C)CC1)c1nnc(-c2cc3ccccc3nc2OC)o1] | 508 | Example 3 |
| 48 | (S)-2-(5-methoxy-2-methyl-1H-indol-3-yl)-N-(1-(5-(2-methoxyquinolin-3-yl)-1,3,4-oxadiazol-2-yl)-7-oxononyl)acetamide | 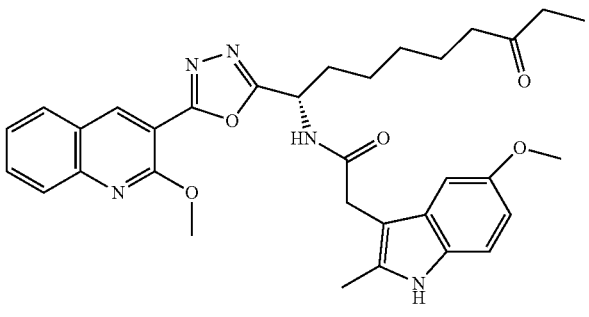 | 584 | Example 4 |
| 49 | (S)-N-(1-(5-(2-methoxyquinolin-3-yl)-1,3,4-oxadiazol-2-yl)-7-oxononyl)thiazole-5-carboxamide | 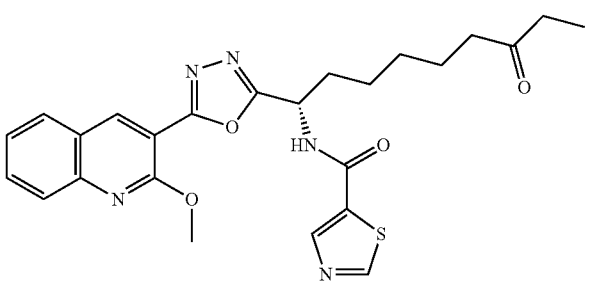 [SMILES: CCC(=O)CCCCC[C@H](NC(=O)c1cncs1)c1nnc(-c2cc3ccccc3nc2OC)o1] | 494 | Example 4 |
| 50 | (S)-3-(2-ethyl-1H-benzo[d]imidazol-1-yl)-N-(1-(5-(2-methoxyquinolin-3-yl)-1,3,4-oxadiazol-2-yl)-7-oxononyl)propanamide | 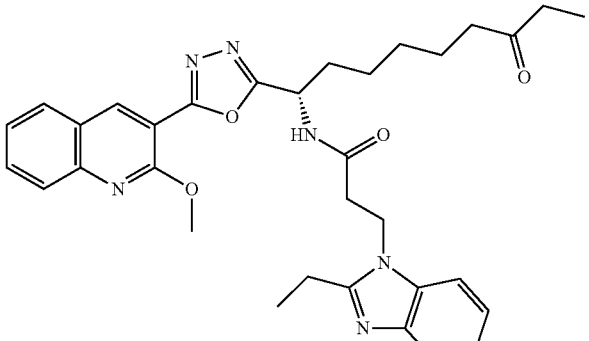 | 583 | Example 4 |

TABLE 1-continued

| Cpd | Compound Name | Structure | Molecular Ion [M + H]+ | Procedure |
|---|---|---|---|---|
| 51 | (S)-3-(dimethylamino)-N-(1-(5-(2-methoxyquinolin-3-yl)-1,3,4-oxadiazol-2-yl)-7-oxononyl)propanamide | 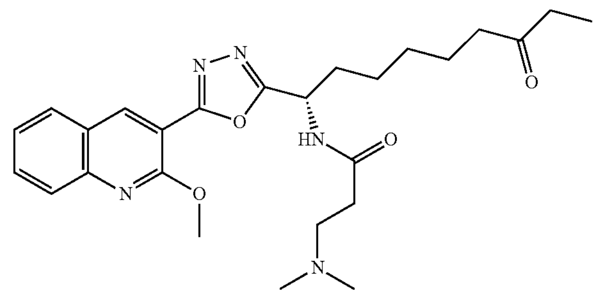 [SMILES: CCC(=O)CCCCC[C@H](NC(=O)CCN(C)C)c1nnc(-c2cc3ccccc3nc2OC)o1] | 482 | Example 4 |
| 52 | (S)-N-(1-(5-(2-methoxyquinolin-3-yl)-1,3,4-oxadiazol-2-yl)-7-oxononyl)-1-methylazetine-3-carboxamide | 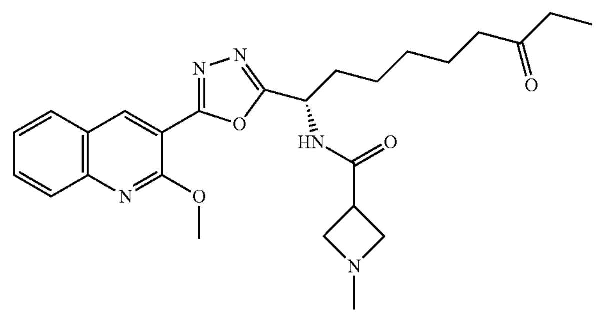 [SMILES: CCC(=O)CCCCC[C@H](NC(=O)C1CN(C)C1)c1nnc(-c2cc3ccccc3nc2OC)o1] | 480 | Example 3 |
| 53 | (S)-N-(1-(5-(4-(1H-pyrazol-5-yl)phenyl)oxazol-2-yl)-7-oxononyl)-1-methylazetidine-3-carboxamide | 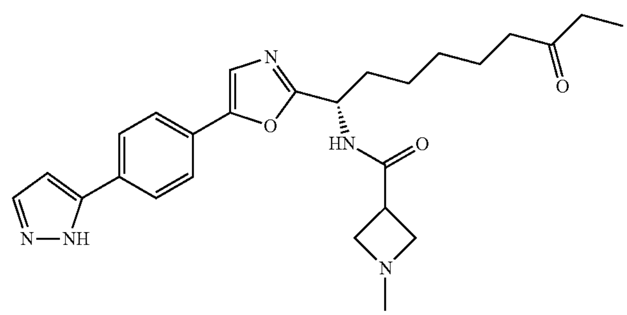 [SMILES: CCC(=O)CCCCC[C@H](NC(=O)C1CN(C)C1)c1ncc(-c2ccc(-c3ccn[nH]3)cc2)o1] | 464 | Example 2 |
| 54 | (S)-1-methyl-N-(1-(5-(4-(1-methyl-1H-pyrazol-5-yl)phenyl)oxazol-2-yl)-7-oxononyl)azetidine-3-carboxamide | 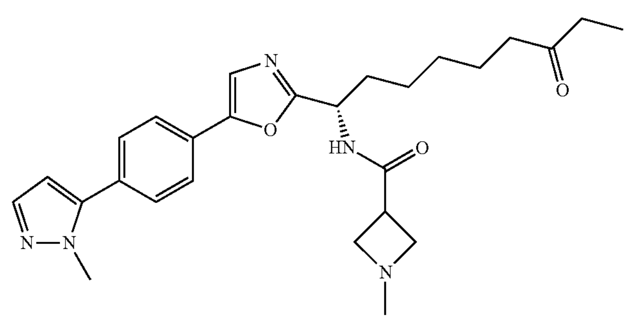 [SMILES: CCC(=O)CCCCC[C@H](NC(=O)C1CN(C)C1)c1ncc(-c2ccc(-c3ccnn3C)cc2)o1] | 478 | Example 2 |
| 55 | (S)-1-acetyl-N-(1-(5-(2-methoxyquinolin-3-yl)oxazol-2-yl)-7-oxononyl)azetidine-3-carboxamide | 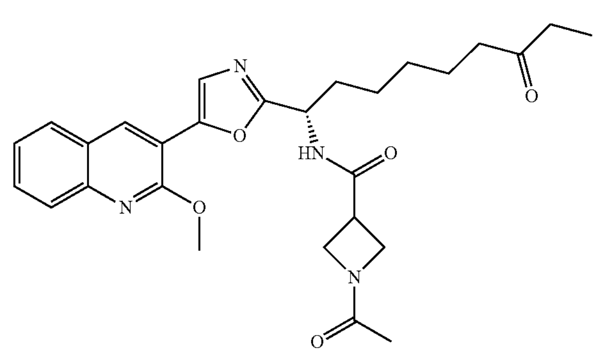 [SMILES: CCC(=O)CCCCC[C@H](NC(=O)C1CN(C(C)=O)C1)c1ncc(-c2cc3ccccc3nc2OC)o1] | 507 | Example 2 |

TABLE 1-continued

| Cpd | Compound Name | Structure | Molecular Ion [M + H]+ | Procedure |
|---|---|---|---|---|
| 56 | (S)-1-benzyl-N-(1-(5-(2-methoxyquinolin-3-yl)oxazol-2-yl)-7-oxononyl)azetidine-3-carboxamide | 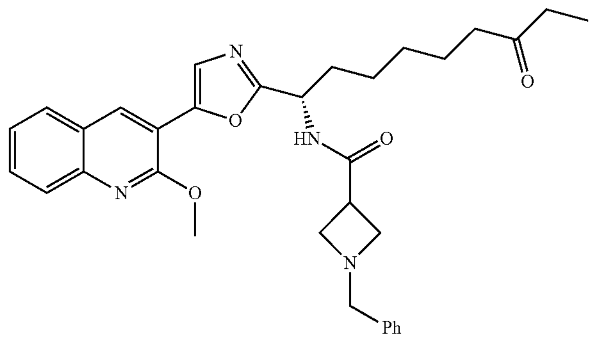 [SMILES: CCC(=O)CCCCC[C@H](NC(=O)C1CN(Cc2ccccc2)C1)c1ncc(-c2cc3ccccc3nc2OC)o1] | 555 | Example 2 |
| 57 | (S)-N-(1-(5-(2-methoxyquinolin-3-yl)oxazol-2-yl)-7-oxononyl)azetidine-3-carboxamide | 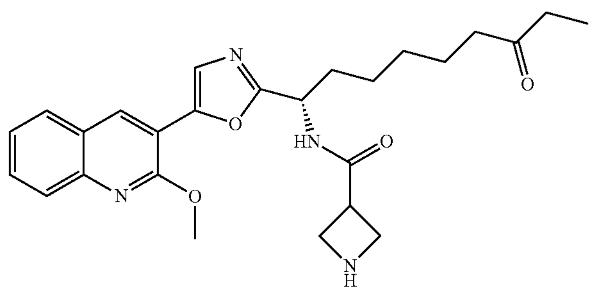 [SMILES: CCC(=O)CCCCC[C@H](NC(=O)C1CNC1)c1ncc(-c2cc3ccccc3nc2OC)o1] | 465 | Example 2 |
| 58 | (S)-4,4-difluoro-N-((S)-1-(5-(2-methoxyquinolin-3-yl)oxazol-2-yl)-7-oxononyl)-1-methypyrrolidine-2-carboxamide | 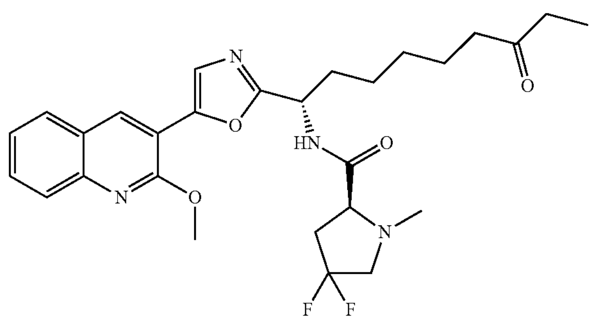 [SMILES: CCC(=O)CCCCC[C@H](NC(=O)[C@@H]1CC(F)(F)CN1C)c1ncc(-c2cc3ccccc3nc2OC)o1] | 529 | Example 2 |
| 59 | (S)-N-(1-(5-(2-methoxyquinolin-3-yl)oxazol-2-yl)-7-oxononyl)-2-(1H-1,2,3-triazol-1-yl)acetamide | 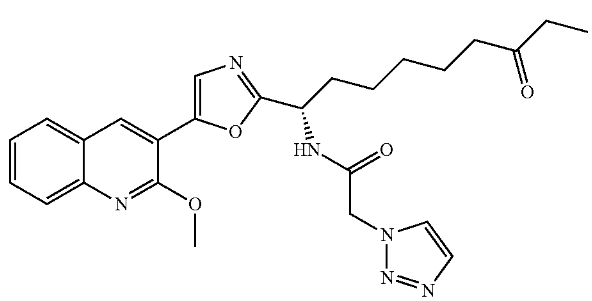 [SMILES: CCC(=O)CCCCC[C@H](NC(=O)Cn1ccnn1)c1ncc(-c2cc3ccccc3nc2OC)o1] | 491 | Example 1 |

TABLE 1-continued

| Cpd | Compound Name | Structure | Molecular Ion [M + H]+ | Procedure |
|---|---|---|---|---|
| 60 | (S)-4,4-difluoro-N-((S)-1-(5-(2-methoxyquinolin-3-yl)oxazol-2-yl)-7-oxononyl)pyrrolidine-2-carboxamide | 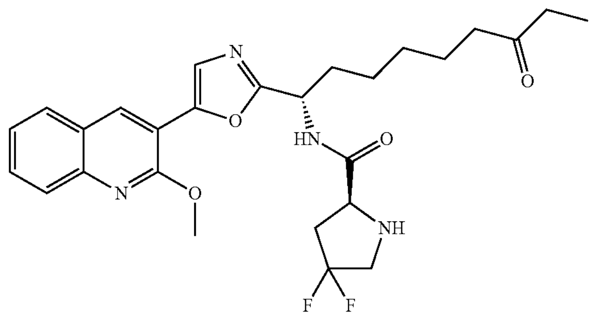 [SMILES: CCC(=O)CCCCC[C@H](NC(=O)[C@@H]1CC(F)(F)CN1)c1ncc(-c2cc3ccccc3nc2OC)o1] | 515 | Example 2 |
| 61 | (S)-N-(1-(5-(4-(1H-pyrazol-1-yl)phenyl)oxazol-2-yl)-7-oxononyl)-1-methylazetidine-3-carboxamide | 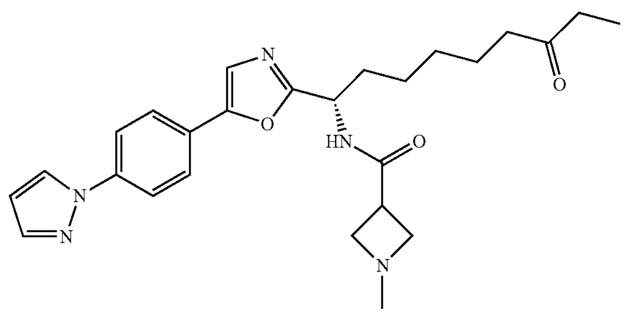 [SMILES: CCC(=O)CCCCC[C@H](NC(=O)C1CN(C)C1)c1ncc(-c2ccc(-n3cccn3)cc2)o1] | 464 | Example 2 |
| 62 | (S)-N-(1-(5-(4-(1H-pyrazol-1-yl)phenyl)oxazol-2-yl)-7-oxononyl)-1-acetylazetidine-3-carboxamide | 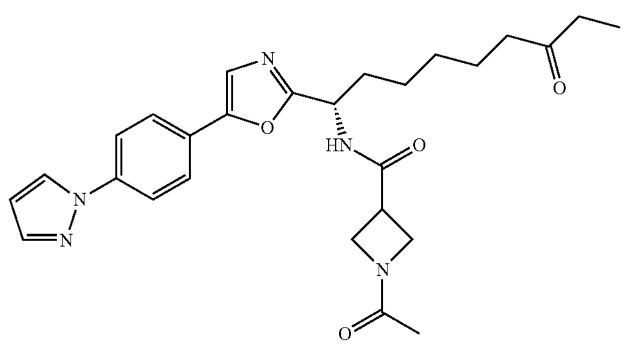 [SMILES: CCC(=O)CCCCC[C@H](NC(=O)C1CN(C(C)=O)C1)c1ncc(-c2ccc(-n3cccn3)cc2)o1] | 492 | Example 2 |
| 63 | (S)-2-(dimethylamino)-4,4,4-trifluoro-N-((S)-1-(5-(2-methoxyquinolin-3-yl)oxazol-2-yl)-7-oxononyl)butanamide | 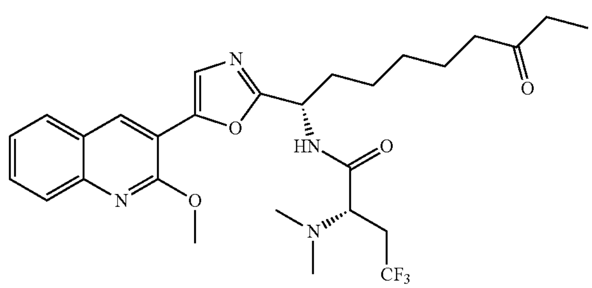 [SMILES: CCC(=O)CCCCC[C@H](NC(=O)[C@H](CC(F)(F)F)N(C)C)c1ncc(-c2cc3ccccc3nc2OC)o1] | 549 | Example 2 |
| 64 | (R)-2-(dimethylamino)-4,4,4-trifluoro-N-((S)-1-(5-(2-methoxyquinolin-3-yl)oxazol-2-yl)-7-oxononyl)butanamide | 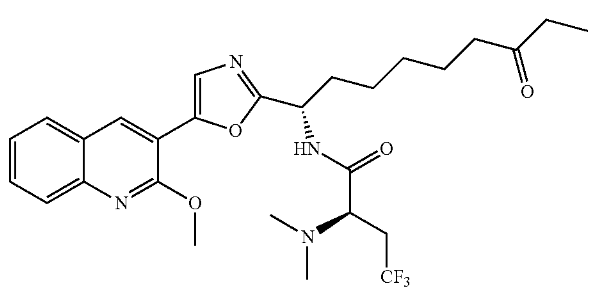 [SMILES: CCC(=O)CCCCC[C@H](NC(=O)[C@@H](CC(F)(F)F)N(C)C)c1ncc(-c2cc3ccccc3nc2OC)o1] | 549 | Example 2 |

TABLE 1-continued

| Cpd | Compound Name | Structure | Molecular Ion [M + H]+ | Procedure |
|---|---|---|---|---|
| 65 | (S)-N-(1-(5-(4-(6-methoxypyridin-3-yl)phenyl)oxazol-2-yl)-7-oxononyl)-1-methylazetidine-3-carboxamide | 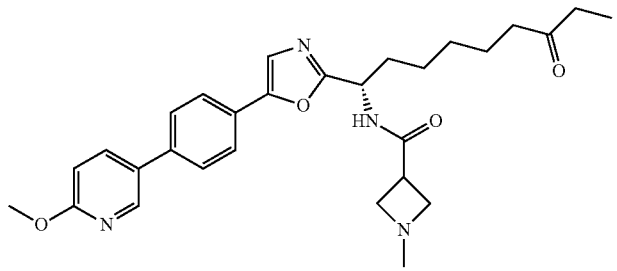 [SMILES: CCC(=O)CCCCC[C@H](NC(=O)C1CN(C)C1)c1ncc(-c2ccc(-c3ccc(OC)nc3)cc2)o1] | 505 | Example 2 |
| 66 | (2S,4S)-4-fluoro-N-((S)-1-(5-(2-methoxyquinolin-3-yl)oxazol-2-yl)-7-oxononyl)-1-methylpyrrolidine-2-carboxamide | 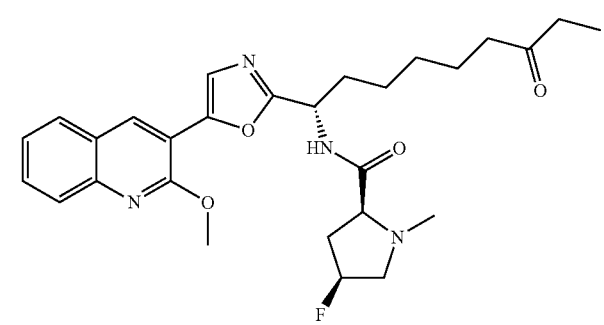 [SMILES: CCC(=O)CCCCC[C@H](NC(=O)[C@@H]1C[C@H](F)CN1C)c1ncc(-c2cc3ccccc3nc2OC)o1] | 511 | Example 2 |
| 67 | (S)-3-fluoro-N-(1-(5-(2-methoxyquinolin-3-yl)oxazol-2-yl)-7-oxononyl)-1-methylazetidine-3-carboxamide | 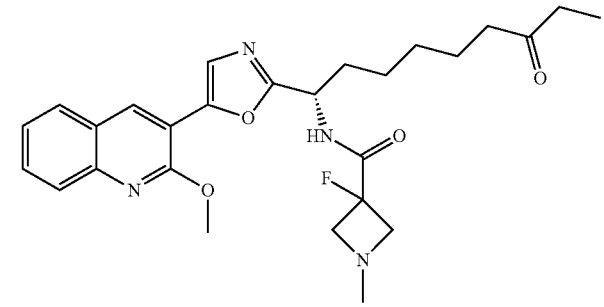 [SMILES: CCC(=O)CCCCC[C@H](NC(=O)C1(F)CN(C)C1)c1ncc(-c2cc3ccccc3nc2OC)o1] | 497 | Example 2 |
| 68 | (S)-4-fluoro-N-(1-(5-(2-methoxyquinolin-3-yl)oxazol-2-yl)-7-oxononyl)-1-methylpiperidine-4-carboxamide | 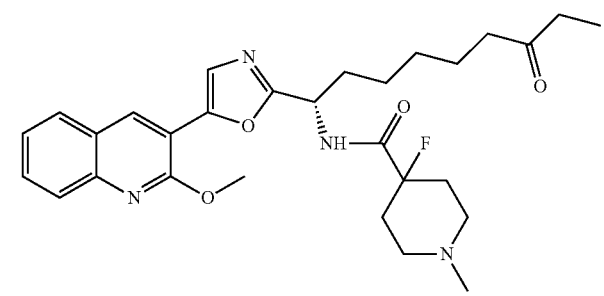 [SMILES: CCC(=O)CCCCC[C@H](NC(=O)C1(F)CCN(C)CC1)c1ncc(-c2cc3ccccc3nc2OC)o1] | 525 | Example 2 |
| 69 | (S)-N-(1-(5-(2-methoxyquinolin-3-yl)oxazol-2-yl)-7-oxononyl)-2-morpholino-2-oxoacetamide | 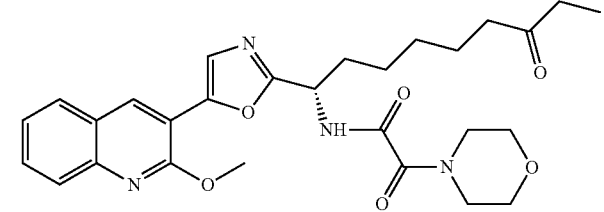 [SMILES: CCC(=O)CCCCC[C@H](NC(=O)C(=O)N1CCOCC1)c1ncc(-c2cc3ccccc3nc2OC)o1] | 523 | Example 1 |

TABLE 1-continued

| Cpd | Compound Name | Structure | Molecular Ion [M + H]+ | Procedure |
|---|---|---|---|---|
| 70 | (S)-1-methyl-N-(7-oxo-1-(5-(quinolin-8-yl)oxazol-2-yl)nonyl)azetidine-3-carboxamide | 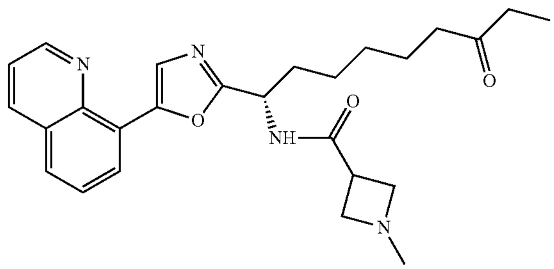 [SMILES: CCC(=O)CCCCC[C@H](NC(=O)C1CN(C)C1)c1ncc(-c2cccc3cccnc23)o1] | 449 | Example 2 |
| 71 | (S)-1-methyl-N-(1-(5-(1-methyl-2-oxo-1,2-dihydroquinolin-3-yl)-1,3,4-oxadiazol-2-yl)-7-oxononyl)azetidine-3-carboxamide | 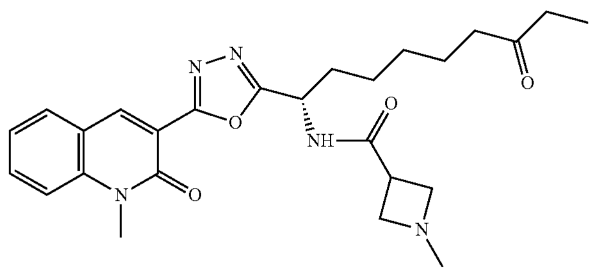 [SMILES: CCC(=O)CCCCC[C@H](NC(=O)C1CN(C)C1)c1nnc(-c2cc3ccccc3n(C)c2=O)o1] | 480 | Example 3 |
| 72 | N-((S)-1-(5-(2-methoxyquinolin-3-yl)oxazol-2-yl)-7-oxononyl)-5-oxopyrrolidine-3-carboxamide | 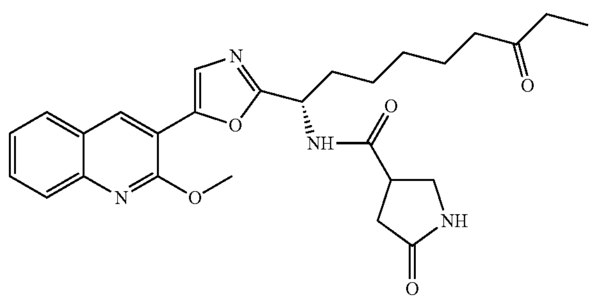 [SMILES: CCC(=O)CCCCC[C@H](NC(=O)C1CNC(=O)C1)c1ncc(-c2cc3ccccc3nc2OC)o1] | 493 | Example 1 |
| 73 | (S)-2-(1H-imidazol-4-yl)-N-(1-(5-(2-methoxyquinolin-3-yl)oxazol-2-yl)-7-oxononyl)acetamide | 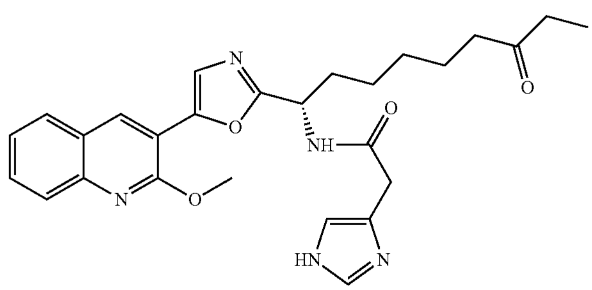 [SMILES: CCC(=O)CCCCC[C@H](NC(=O)Cc1c[nH]cn1)c1ncc(-c2cc3ccccc3nc2OC)o1] | 490 | Example 1 |
| 74 | (S)-N-(1-(5-(2-methoxyquinolin-3-yl)oxazol-2-yl)-7-oxononyl)-2-(pyridin-3-yl)acetamide | 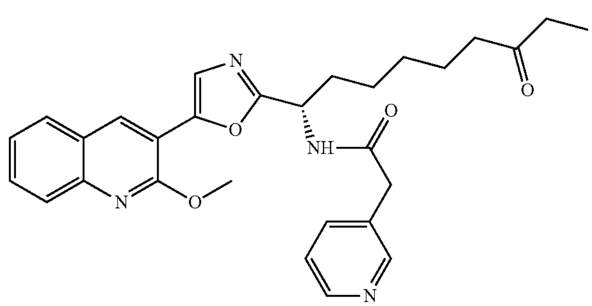 [SMILES: CCC(=O)CCCCC[C@H](NC(=O)Cc1cccnc1)c1ncc(-c2cc3ccccc3nc2OC)o1] | 501 | Example 1 |

TABLE 1-continued

| Cpd | Compound Name | Structure | Molecular Ion [M + H]+ | Procedure |
|---|---|---|---|---|
| 75 | (S)-3-(1H-imidazol-1-yl)-N-(1-(5-(2-methoxyquinolin-3-yl)oxazol-2-yl)-7-oxononyl)propanamide | 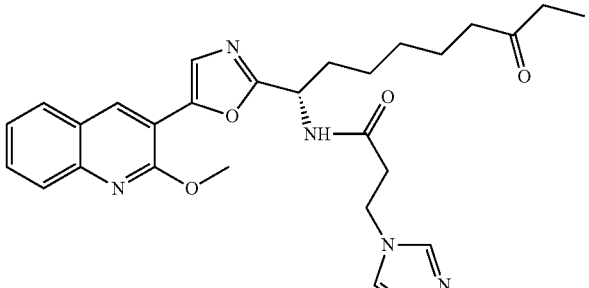 | 504 | Example 1 |
| 76 | (S)-N-(1-(5-(2-methoxyquinolin-3-yl)oxazol-2-yl)-7-oxononyl)-2-(thiazol-2-yl)acetamide | 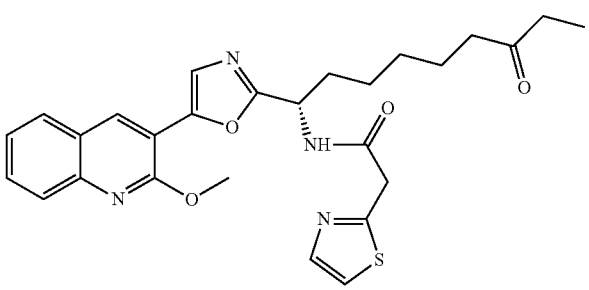 [SMILES: CCC(=O)CCCCC[C@H](NC(=O)Cc1nccs1)c1ncc(-c2cc3ccccc3nc2OC)o1] | 507 | Example 1 |
| 77 | (S)-N-(1-(5-(2-methoxyquinolin-3-yl)oxazol-2-yl)-7-oxononyl)-2-(4-methyl-1,2,5-oxadiazol-3-yl)acetamide | 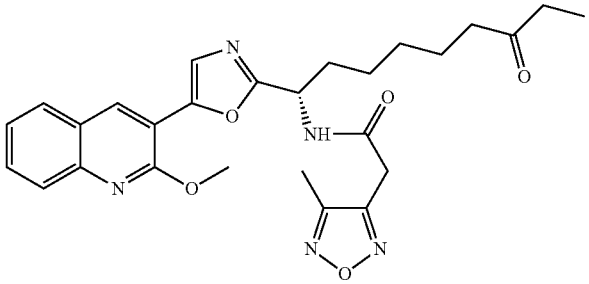 [SMILES: CCC(=O)CCCCC[C@H](NC(=O)Cc1nonc1C)c1ncc(-c2cc3ccccc3nc2OC)o1] | 506 | Example 1 |
| 78 | (S)-N-(1-(5-(2-methoxyquinolin-3-yl)oxazol-2-yl)-7-oxononyl)-2-(3-methyl-1H-pyrazol-1-yl)acetamide | 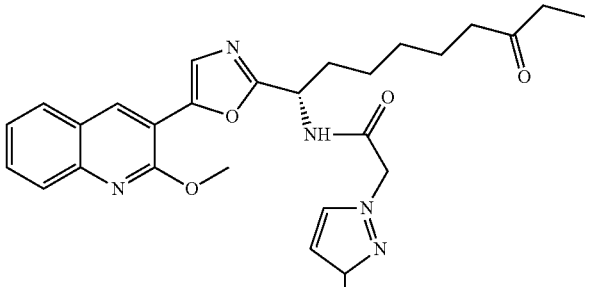 | 504 | Example 1 |
| 79 | (S)-N-(1-(5-(2-methoxyquinolin-3-yl)oxazol-2-yl)-7-oxononyl)-2-(pyrimidin-2-yl)acetamide | 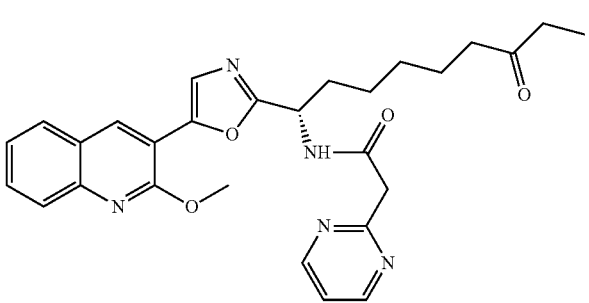 [SMILES: CCC(=O)CCCCC[C@H](NC(=O)Cc1ncccn1)c1ncc(-c2cc3ccccc3nc2OC)o1] | 502 | Example 1 |

TABLE 1-continued

| Cpd | Compound Name | Structure | Molecular Ion [M + H]+ | Procedure |
|---|---|---|---|---|
| 80 | (S)-2-(3,5-dimethyl-1H-1,2,4-triazol-1-yl)-N-(1-(5-(2-methoxyquinolin-3-yl)oxazol-2-yl)-7-oxononyl)acetamide | 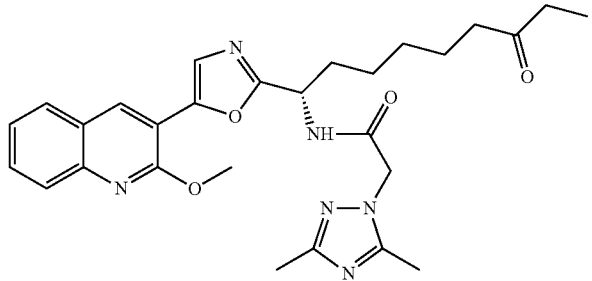 [SMILES: CCC(=O)CCCCC[C@H](NC(=O)Cn1nc(C)nc1C)c1ncc(-c2cc3ccccc3nc2OC)o1] | 519 | Example 1 |
| 81 | (S)-2-(3,5-dimethyl-1H-pyrazol-1-yl)-N-(1-(5-(2-methoxyquinolin-3-yl)oxazol-2-yl)-7-oxononyl)acetamide | 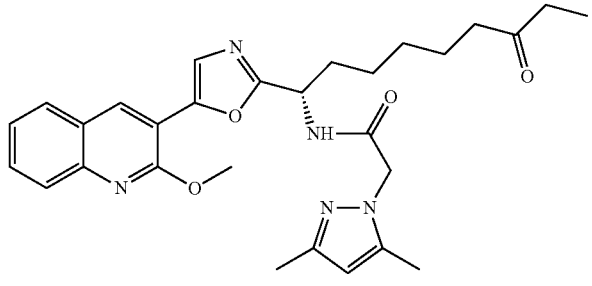 [SMILES: CCC(=O)CCCCC[C@H](NC(=O)Cn1nc(C)cc1C)c1ncc(-c2cc3ccccc3nc2OC)o1] | 518 | Example 1 |
| 82 | (S)-N-(1-(5-(2-methoxyquinolin-3-yl)oxazol-2-yl)-7-oxononyl)-2-(pyrrolidin-1-ylmethyl)thiazole-5-carboxamide | 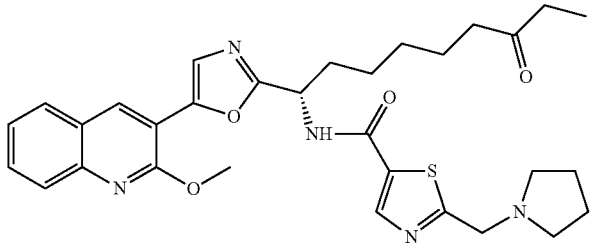 [SMILES: CCC(=O)CCCCC[C@H](NC(=O)c1cnc(CN2CCCC2)s1)c1ncc(-c2cc3ccccc3nc2OC)o1] | 576 | Example 1 |
| 83 | (S)-N-(1-(5-(2-methoxyquinolin-3-yl)oxazol-2-yl)-7-oxononyl)-2,4-dimethylthiazole-5-carboxamide | 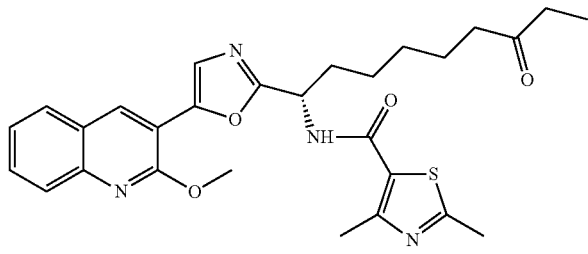 [SMILES: CCC(=O)CCCCC[C@H](NC(=O)c1sc(C)nc1C)c1ncc(-c2cc3ccccc3nc2OC)o1] | 521 | Example 1 |
| 84 | (S)-N-(1-(5-(2-methoxyquinolin-3-yl)oxazol-2-yl)-7-oxononyl)-1,3-dimethylazetidine-3-carboxamide | 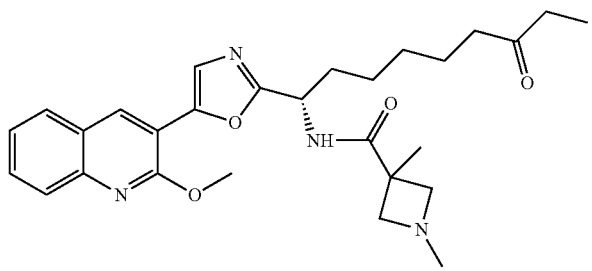 [SMILES: CCC(=O)CCCCC[C@H](NC(=O)C1(C)CN(C)C1)c1ncc(-c2cc3ccccc3nc2OC)o1] | 493 | Example 2 |

TABLE 1-continued

| Cpd | Compound Name | Structure | Molecular Ion [M + H]+ | Procedure |
|---|---|---|---|---|
| 85 | N-((S)-1-(5-(2-methoxyquinolin-3-yl)oxazol-2-yl)-7-oxononyl)-1-methylazetidine-2-carboxamide | 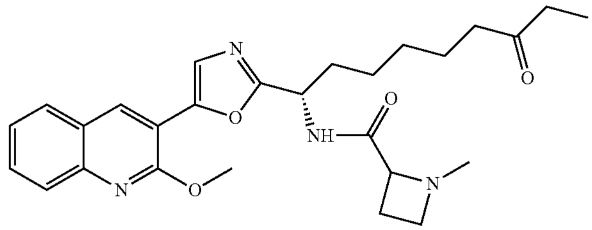 [SMILES: CCC(=O)CCCCC[C@H](NC(=O)C1CCN1C)c1ncc(-c2cc3ccccc3nc2OC)o1] | 479 | Example 2 |
| 86 | (S)-N-(1-(5-(2-methoxyquinolin-3-yl)oxazol-2-yl)-7-oxononyl)-2-(1H-1,2,4-triazol-1-yl)acetamide | 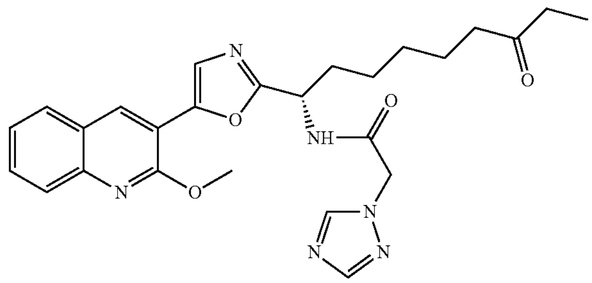 [SMILES: CCC(=O)CCCCC[C@H](NC(=O)Cn1cncn1)c1ncc(-c2cc3ccccc3nc2OC)o1] | 491 | Example 1 |
| 87 | (S)-N-(1-(5-(2-methoxyquinolin-3-yl)oxazol-2-yl)-7-oxononyl)-1-methyl-1H-pyrazole-5-carboxamide | 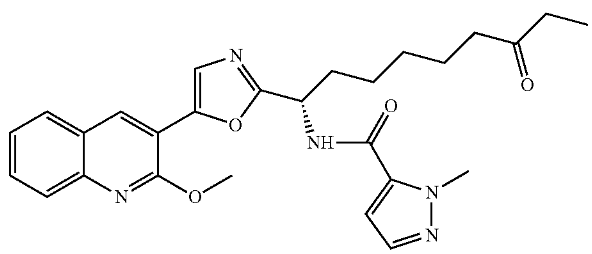 [SMILES: CCC(=O)CCCCC[C@H](NC(=O)c1ccnn1C)c1ncc(-c2cc3ccccc3nc2OC)o1] | 490 | Example 1 |
| 88 | (S)-2-(2H-indazol-2-yl)-N-(1-(5-(2-methoxyquinolin-3-yl)oxazol-2-yl)-7-oxononyl)acetamide | 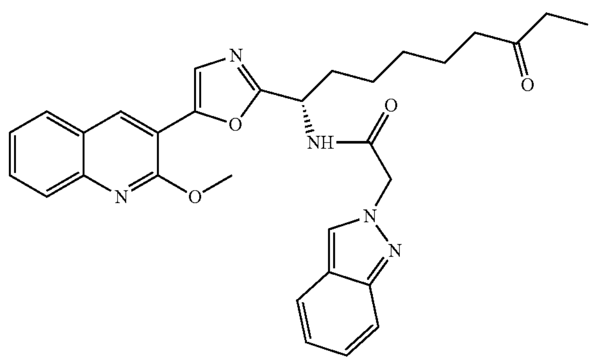 [SMILES: CCC(=O)CCCCC[C@H](NC(=O)Cn1cc2ccccc2n1)c1ncc(-c2cc3ccccc3nc2OC)o1] | 540 | Example 1 |
| 89 | (S)-N-(1-(5-(2-methoxyquinolin-3-yl)oxazol-2-yl)-7-oxononyl)-2-(pyrazolo[1,5-a]pyrimidin-2-yl)acetamide | 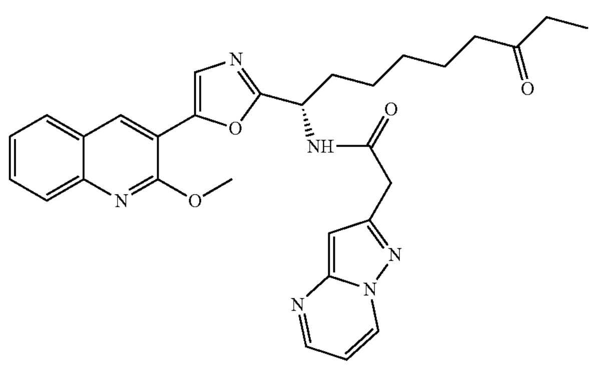 [SMILES: CCC(=O)CCCCC[C@H](NC(=O)Cc1cc2ncccn2n1)c1ncc(-c2cc3ccccc3nc2OC)o1] | 541 | Example 1 |

TABLE 1-continued

| Cpd | Compound Name | Structure | Molecular Ion [M + H]+ | Procedure |
|---|---|---|---|---|
| 90 | (S)-N-(1-(5-(2-methoxyquinolin-3-yl)oxazol-2-yl)-7-oxononyl)-5-methyl-1,3,4-oxadiazole-2-carboxamide | 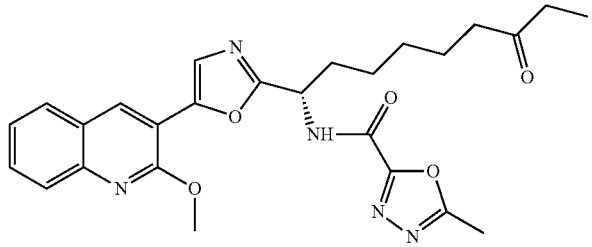 [SMILES: CCC(=O)CCCCC[C@H](NC(=O)c1nnc(C)o1)c1ncc(-c2cc3ccccc3nc2OC)o1] | 492 | Example 1 |
| 91 | (S)-N-(1-(5-(2-methoxyquinolin-3-yl)oxazol-2-yl)-7-oxononyl)nicotinamide | 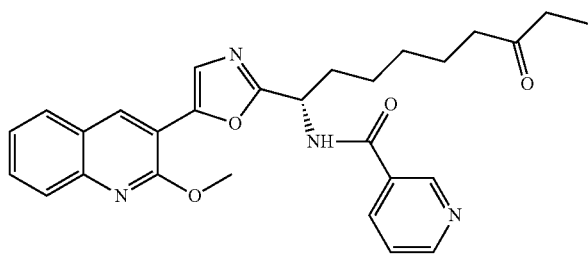 [SMILES: CCC(=O)CCCCC[C@H](NC(=O)c1cccnc1)c1ncc(-c2cc3ccccc3nc2OC)o1] | 487 | Example 1 |
| 92 | (S)-1-methyl-N-(1-(5-(1-methyl-2-oxo-1,2-dihydroquinolin-3-yl)oxazol-2-yl)-7-oxononyl)azetidine-3-carboxamide | 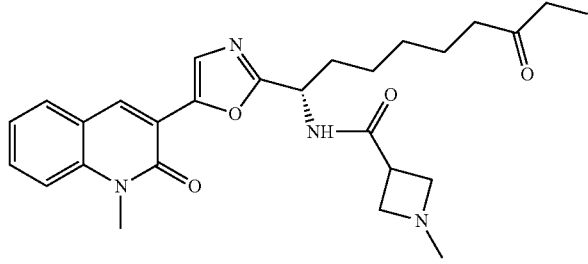 [SMILES: CCC(=O)CCCCC[C@H](NC(=O)C1CN(C)C1)c1ncc(-c2cc3ccccc3n(C)c2=O)o1] | 479 | Example 7 |
| 93 | (S)-N-(1-(5-(2-methoxyquinolin-3-yl)oxazol-2-yl)-7-oxononyl)-3-(1-methyl-1H-pyrazol-4-yl)propanamide | 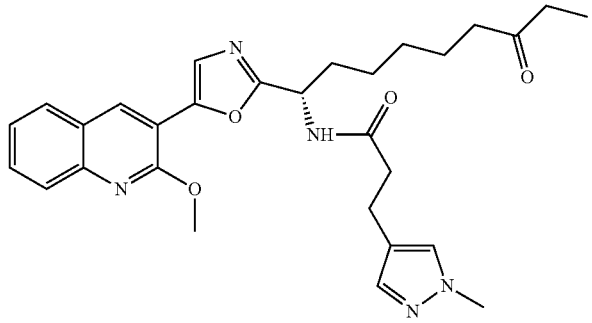 [SMILES: CCC(=O)CCCCC[C@H](NC(=O)CCc1cnn(C)c1)c1ncc(-c2cc3ccccc3nc2OC)o1] | 518 | Example 1 |
| 94 | (S)-N-(1-(5-(2-methoxyquinolin-3-yl)oxazol-2-yl)-7-oxononyl)-3-(piperidin-1-ylmethyl)isothiazole-5-carboxamide | 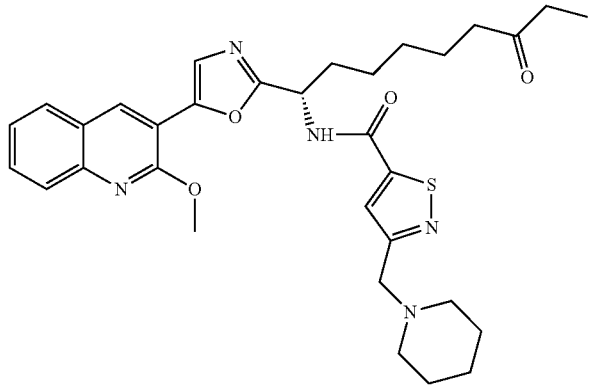 [SMILES: CCC(=O)CCCCC[C@H](NC(=O)c1cc(CN2CCCCC2)ns1)c1ncc(-c2cc3ccccc3nc2OC)o1] | 590 | Example 1 |

TABLE 1-continued

| Cpd | Compound Name | Structure | Molecular Ion [M + H]+ | Procedure |
|---|---|---|---|---|
| 95 | 2-(3,5-dimethyl-1H-pyrazol-1-yl)-N-((S)-1-(5-(2-methoxyquinolin-3-yl)oxazol-2-yl)-7-oxononyl)propanamide | 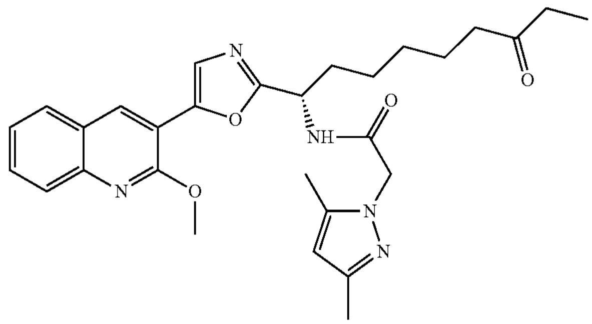 [SMILES: CCC(=O)CCCCC[C@H](NC(=O)Cn1nc(C)cc1C)c1ncc(-c2cc3ccccc3nc2OC)o1] | 532 | Example 1 |
| 96 | (S)-N-(1-(5-(2-methoxyquinolin-3-yl)oxazol-2-yl)-7-oxononyl)-1,3-dimethyl-1H-pyrazole-5-carboxamide | 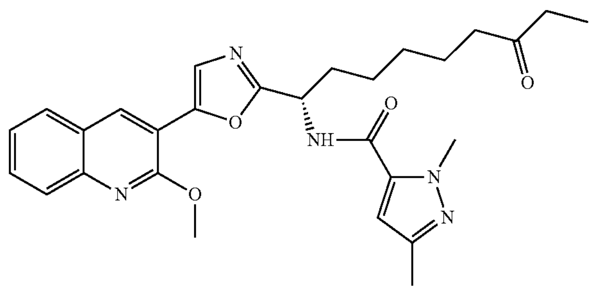 [SMILES: CCC(=O)CCCCC[C@H](NC(=O)c1cc(C)nn1C)c1ncc(-c2cc3ccccc3nc2OC)o1] | 504 | Example 1 |
| 97 | (S)-2-(1H-benzo[d]imidazol-1-yl)-N-(1-(5-(2-methoxyquinolin-3-yl)oxazol-2-yl)-7-oxononyl)acetamide | 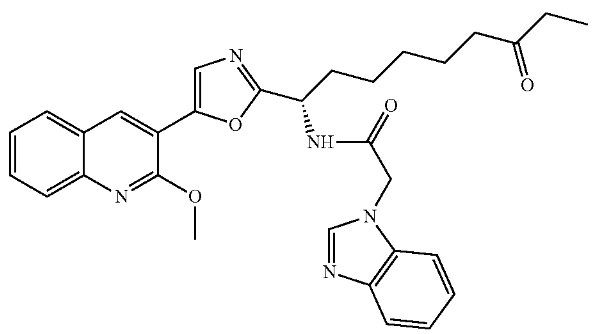 [SMILES: CCC(=O)CCCCC[C@H](NC(=O)Cn1cnc2ccccc21)c1ncc(-c2cc3ccccc3nc2OC)o1] | 540 | Example 1 |
| 98 | (S)-N-(1-(5-(2-methoxyquinolin-3-yl)oxazol-2-yl)-7-oxononyl)-1-methyl-1H-pyrazole-3-carboxamide | 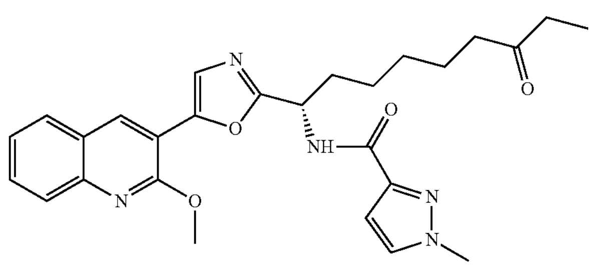 [SMILES: CCC(=O)CCCCC[C@H](NC(=O)c1ccn(C)n1)c1ncc(-c2cc3ccccc3nc2OC)o1] | 490 | Example 1 |
| 99 | (S)-N-(1-(5-(2-methoxyquinolin-3-yl)oxazol-2-yl)-7-oxononyl)-1,2,3-thiadiazole-4-carboxamide | 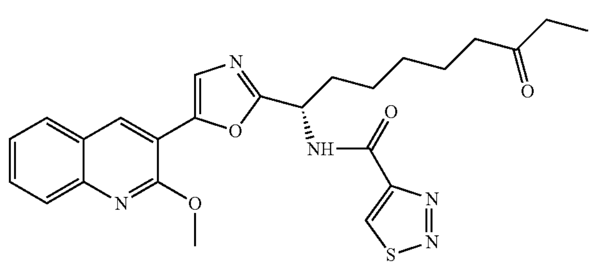 [SMILES: CCC(=O)CCCCC[C@H](NC(=O)c1csnn1)c1ncc(-c2cc3ccccc3nc2OC)o1] | 494 | Example 1 |

TABLE 1-continued

| Cpd | Compound Name | Structure | Molecular Ion [M + H]+ | Procedure |
|---|---|---|---|---|
| 100 | (S)-N-(1-(5-(2-methoxyquinolin-3-yl)oxazol-2-yl)-7-oxononyl)isothiazole-5-carboxamide | 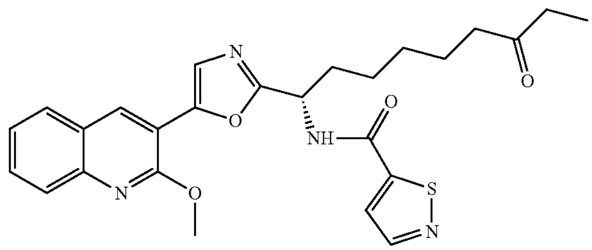 [SMILES: CCC(=O)CCCCC[C@H](NC(=O)c1ccns1)c1ncc(-c2cc3ccccc3nc2OC)o1] | 493 | Example 1 |
| 101 | (S)-N-(1-(5-(2-methoxyquinolin-3-yl)oxazol-2-yl)-7-oxononyl)-4-methyl-1,2,3-thiadiazole-5-carboxamide | 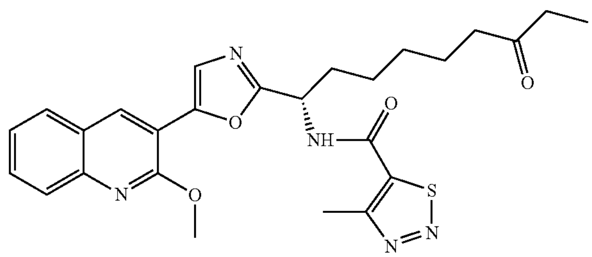 [SMILES: CCC(=O)CCCCC[C@H](NC(=O)c1snnc1C)c1ncc(-c2cc3ccccc3nc2OC)o1] | 508 | Example 1 |
| 102 | N-((S)-1-(5-(2-methoxyquinolin-3-yl)oxazol-2-yl)-7-oxononyl)2-(1H-pyrazol-1-yl)propanamide | 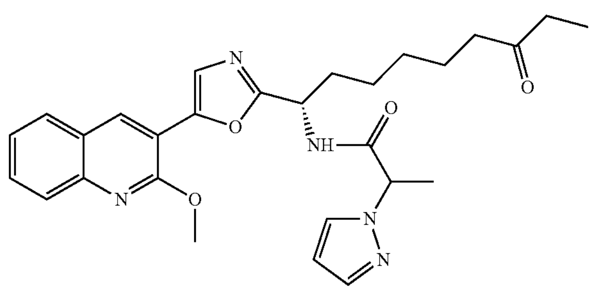 [SMILES: CCC(=O)CCCCC[C@H](NC(=O)C(C)n1cccn1)c1ncc(-c2cc3ccccc3nc2OC)o1] | 504 | Example 1 |
| 103 | (S)-2-((dimethylamino)methyl)-N-(1-(5-(2-methoxyquinolin-3-yl)oxazol-2-yl)-7-oxononyl)thiazole-4-carboxamide | 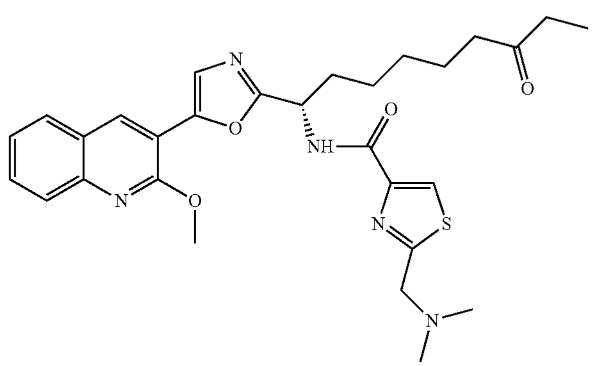 [SMILES: CCC(=O)CCCCC[C@H](NC(=O)c1csc(CN(C)C)n1)c1ncc(-c2cc3ccccc3nc2OC)o1] | 550 | Example 1 |
| 104 | N-((S)-1-(5-(2-methoxyquinolin-3-yl)oxazol-2-yl)-7-oxononyl)-1-methylpiperidine-3-carboxamide | 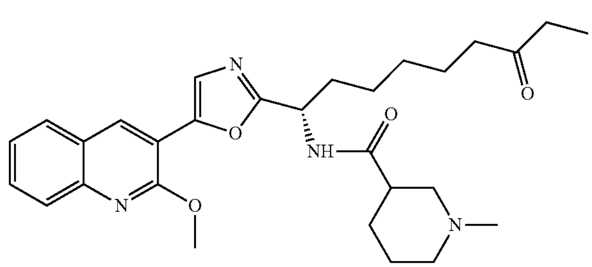 [SMILES: CCC(=O)CCCCC[C@H](NC(=O)C1CCCN(C)C1)c1ncc(-c2cc3ccccc3nc2OC)o1] | 507 | Example 2 |

TABLE 1-continued

| Cpd | Compound Name | Structure | Molecular Ion [M + H]+ | Procedure |
|---|---|---|---|---|
| 105 | (S)-1-(dimethylamino)-N-(1-(5-(2-methoxyquinolin-3-yl)oxazol-2-yl)-7-oxononyl)cyclopentanecarboxamide | 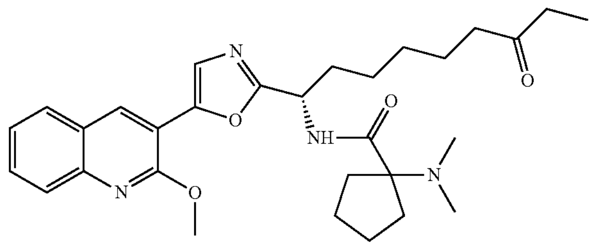 [SMILES: CCC(=O)CCCCC[C@H](NC(=O)C1(N(C)C)CCCC1)c1ncc(-c2cc3ccccc3nc2OC)o1] | 521 | Example 2 |
| 106 | (S)-3-(dimethylamino)-N-(1-(5-(1-methyl-2-oxo-1,2-dihydroquinolin-3-yl)oxazol-2-yl)-7-oxononyl)propanamide | 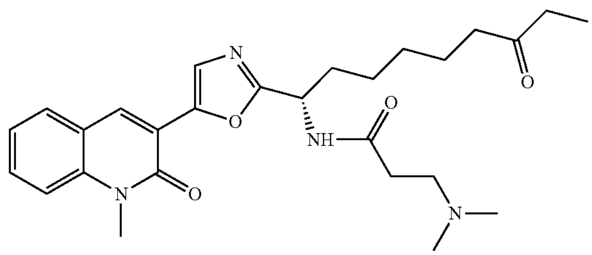 [SMILES: CCC(=O)CCCCC[C@H](NC(=O)CCN(C)C)c1ncc(-c2cc3ccccc3n(C)c2=O)o1] | 481 | Example 8 |
| 107 | (S)-2-(dimethylamino)-2-methyl-N-(1-(5-(1-methyl-2-oxo-1,2-dihydroquinolin-3-yl)oxazol-2-yl)-7-oxononyl)propanamide | 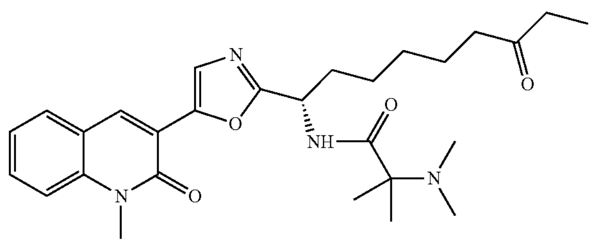 [SMILES: CCC(=O)CCCCC[C@H](NC(=O)C(C)(C)N(C)C)c1ncc(-c2cc3ccccc3n(C)c2=O)o1] | 495 | Example 7 |
| 108 | (S)-N-(1-(5-(2-methoxyquinolin-3-yl)oxazol-2-yl)-7-oxononyl)-2-(1-methylazetidin-3-yl)acetamide | 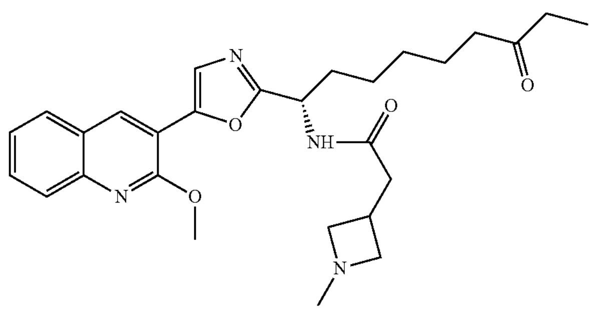 [SMILES: CCC(=O)CCCCC[C@H](NC(=O)CC1CN(C)C1)c1ncc(-c2cc3ccccc3nc2OC)o1] | 493 | Example 7 |
| 109 | (S)-1-methyl-N-(1-(5-(1-methyl-2-oxo-1,2-dihydroquinolin-3-yl)oxazol-2-yl)-7-oxononyl)piperidine-4-carboxamide | 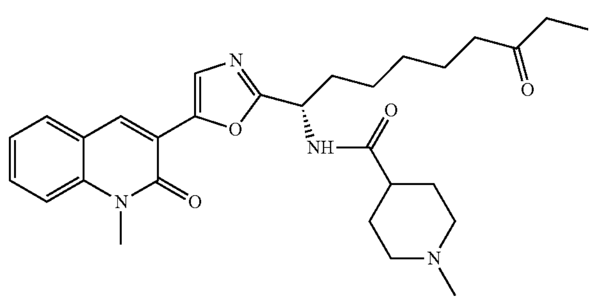 [SMILES: CCC(=O)CCCCC[C@H](NC(=O)C1CCN(C)CC1)c1ncc(-c2cc3ccccc3n(C)c2=O)o1] | 507 | Example 7 |

TABLE 1-continued

| Cpd | Compound Name | Structure | Molecular Ion [M + H]+ | Procedure |
|---|---|---|---|---|
| 110 | (S)-N-(1-(5-(1-methyl-2-oxo-1,2-dihydroquinolin-3-yl)oxazol-2-yl)-7-oxononyl)thiazole-5-carboxamide | 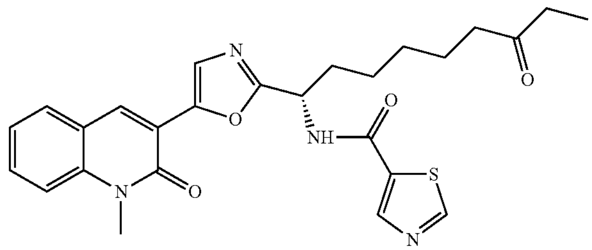 [SMILES: CCC(=O)CCCCC[C@H](NC(=O)c1cncs1)c1ncc(-c2cc3ccccc3n(C)c2=O)o1] | 493 | Example 8 |
| 111 | (S)-1-(dimethylamino)-N-(1-(5-(1-methyl-2-oxo-1,2-dihydroquinolin-3-yl)oxazol-2-yl)-7-oxononyl)cyclopentanecarboxamide | 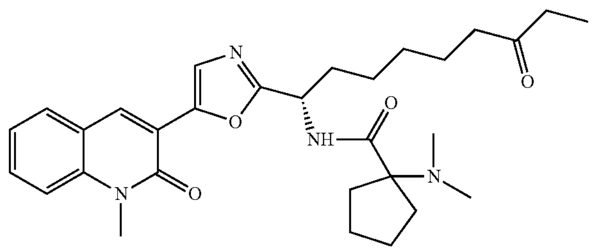 [SMILES: CCC(=O)CCCCC[C@H](NC(=O)C1(N(C)C)CCCC1)c1ncc(-c2cc3ccccc3n(C)c2=O)o1] | 521 | Example 7 |

Biology
HDAC1 Assay

Assay Description:

The HDAC1 assay is used to quantify the histone deacetylase (HDAC) activity. The assay is performed in 384 well microtiter plates by pre-incubating serial dilutions of the compounds with a fixed concentration of HeLa nuclear extract or purified HDAC1 and then adding an acetylated lysine-containing substrate/developer that fluoresces upon deacetylation. The deacetylase reaction is performed at room temperature for 60 min, terminated by addition of the developer solution, and then fluorescence (ex 360 nm, em 460 nm) is measured using a plate reader.

HDAC Substrate Buffer System

Reagents of the HDAC Fluorescent Activity Assay are purchased from BioMol Research Laboratories (Plymouth Meeting, Pa.) and feature the Fluor-de-Lys™ Substrate/Developer System. The reagents include the proprietary fluorescent substrate as a 50 mM stock solution (KI-104), and the Developer Concentrate (KI-105). Deacetylation of the lysine residue of the Fluor-de-Lys substrate is quantified by measuring the fluorescence (ex 360 nm, em 460 nm) after addition of the proprietary Developer.

Working Reagents:

TSA Stock: TSA is provided as a 10 mM stock solution in 100% dimethylsulfoxide (DMSO). Assay Buffer: 25 mM Tris/HCl pH8, 137 mM NaCl, 2.7 mM KCl, 1 mM $MgCl_2$, 0.1 mg/ml BSA. Diluted Substrate Solution: The commercial 50 mM Fluor-de-Lys substrate (KI-104) is diluted to 80 uM with HDAC Assay Buffer prior to each use. The final concentration in the assay is 20 uM.

Diluted Developer Solution: The commercial 20× Developer Concentrate (KI-105) is diluted 1:666 into HDAC Assay Buffer. 3 uM [final] TSA to this solution increases its ability to stop the reaction.

HDAC1 Working Solution: The HDAC1 enzyme is diluted in assay buffer prior to each use from a fresh aliquot of enzyme. The final concentration in the assay is 1-2 nM.

Compounds: Test compounds are directly transferred from a 100% DMSO solution into assay plates by spotting nanoliters of solutions by an acoustic dispenser (ATS-100, EDC biosystems, US). The final DMSO concentration is 0.25%.

Experimental Design:

The reaction is performed in 384-well microplate in a final volume of 20 ul/well, as following:

Add 50 nl of DMSO/compound solution
Add 15 ul of HDAC1 in assay buffer (or 35 ul assay buffer in the negative controls)
Incubate 10' at room temperature
Start the reaction by adding 5 ul of the 80 uM Substrate Solution
Incubate 1 h at room temperature
Stop by adding 10 ul of Developer/3 uM TSA solution
Incubate 10 min at room temperature
Measure the fluorescence at Ex.360 nm and Em.460 nm Extraction and Purification Protocol for Flag-Tagged HDAC1 Expressed in HeLa Cells HeLa cells transiently transfected with pCDNA3-HDAC1-FLAG are grown to 80% confluence on 10 cm culture dishes in DMEM, 10% Fetal bovine serum supplemented with antibiotics and glutamine. Cells are washed with 10 ml cold PBS and scraped into 2 ml of PBS. Cells are centrifuged for 5 minutes at 800×g at 4° C., washed with 30 ml PBS and resuspended in 10 ml PBS, counted, re-centrifuged and frozen at −80° C.

The frozen cell pellet is re-suspended in 1 ml of hypotonic lysis buffer (LB: 20 mM Hepes pH7.9, 0.25 mM EDTA, 10% glycerol) containing COMPLETE protease inhibitor and incubated on ice for 15 minutes, followed by homogenization on a 2-ml DounceB homogenizer (25 strokes). 150 mM KCl and 0.5% NP-40 are added to the homogenate and the solution is sonicated twice for 30 seconds (output5/6, duty cycle 90) and incubated for 1 hour at 4° C. After a 30 minutes centrifugation at 12000 rpm and 4° C. the supernatant (soluble extract) is collected and protein concentration is determined using the BIORAD assay.

Anti-FLAG M2 affinity resin (Sigma) is washed three times with TBS and twice with LB. 10 μl of the LB-washed resin/mg of protein (2-3 ug of Flagged-HDAC1) are added to the soluble extract (1 mL) and incubated overnight at 4° C.

with gentle mixing. The resin is then collected by centrifugation, washed once with LB, twice with LB+0.1% NP40 and twice with elution buffer (50 mM Hepes pH 7.4, 5% glycerol, 100 mM KCl, 0.01% Triton X-100).

The affinity-purified HDAC is eluted from the resin by addition of a 10-fold excess (with respect to the resin) of elution buffer containing 100 µg/ml 3×FLAG peptide (SIGMA). The concentration of purified HDAC is determined by Western blot analysis.

Other assays are known in the literature and can be readily performed by those skilled in the art.

In Vitro Model System for Screening of Potential Inducers of Fetal Hemoglobin

In order to test several compounds, a model system was produced based on previous findings present in the literature. The K562 erythroid-like cell lines, isolated and characterized by Lozzio & Lozzio (Blood, 45(3), pp 321-334) from a patient with chronic myelogenous leukemia in blast crisis, have been extensively employed as a useful in vitro model to study the molecular mechanism(s) regulating the expression of embryonic and fetal human globin genes, as well as for screening of new differentiation-inducing compounds. A stable cell line where reporter genes encoding green EGFP and far-red fluorescent protein red-FP are placed under the control of the human γ-globin or β-globin promoters respectively was used (see Vadolas et al, Hum. Mol. Genet. 2004, 13, 2, 223-233 for details). The modified 3-cluster also contains the upstream regulatory region called LCR. This cell line grows in suspension at 37° C. and 5% $CO_2$ in humidified atmosphere in the following medium: DMEM, 10% foetal bovine serum, glutamine and antibiotics (penicillin and streptomycin);

The assay procedures is as follows:
Single concentration compounds or serially diluted samples are transferred to an empty assay plates by a spotter (ATS-100, EDC Biosystems, USA) in order to have a final concentration of DMSO of 0.25% in 50 µL of cell culture. Source plats contains compounds dissolved in 100% DMSO Black, transparent bottom, 384 wells, tissue culture treated plates are used as assay plates.

Assay plates containing spotted compounds are filled with a suspension of cell in the described assay medium. The final cell concentration is of 1000 cells per well.

Cells are incubated in humidified atmosphere, 37° C.-5% $CO_2$, for 60 hours

Cell nuclei are stained by adding 10 ul (6 µM; 1 µM final) Hoechst 33342 (Life Technologies, USA)

The cell associated intensity is read by a plate based cytometer (ACUMEN explorer, TTP Labtech, UK)

The nuclei count is used to assess the cell proliferation/death and to normalize the total EGFP/RFP intensity.

HbF Activation Assay in Human Cell Line K562

The biological activity of the compounds of the present application was evaluated by examining the capacity to modulate the expression of γ-globin genes in the human K562 cell line, which is capable of differentiating in the erythroid manner by expressing genes for γ-globin if treated with modifiers of the biological response that are suitable for the purpose (Bianchi et al, J. Haematol., 113, 4, p. 951-961, 2001). The human K562 cells were cultured in RPMI 1640 medium (Sigma, St Louis, Mo., USA) supplemented with 10% foetal bovine serum (FBS; Analitical de Mori, Milan, Italy), 100 units/mL penicillin and 100 µg/mL streptomycin. Cell growth was determined according to cell number/ml, using a cell counter (Coulter Electronics, Hialeah, Fla., USA). For experiments, K562 cell cultures were initiated at $3 \times 10^4$/mL and the chemical inducers at the indicated concentrations added. Following 3-5 days incubation without a medium change erythroid differentiation was determined by staining the cells in a solution containing 0.2% benzidine in 0.5 M glacial acetic acid, 10% $H_2O_2$. Benzidine positivity indicates the presence of intracellular Hb.

The expression of the genes encoding for γ-globin was evaluated by quantitative RT-PCR. The analyses were carried out on material extracted from cells treated for 6 days in the conditions indicated.

Production of γ-Globin mRNA and HbF in Human Erythroid Precursors.

Stimulation of the production of mRNA for γ-globin in human erythroid precursors isolated from peripheral blood was detected by using the technique by Fibach (Fibach, E. Hemoglobin, 1998, 22, 445-458; Blood, 1993, 81, 1630-1635). Blood samples were obtained from subjects after written informed consent and the local ethical commette approved the study. This technique provides for two stages: in the first stage, the cells isolated from peripheral blood of an healthy subject or a subject suffering from a hemopoietic pathology, such as sickle cell anaemia or beta-thalassemia, are sown in a culture medium to which 10% of conditioned medium derived from the vescicle carcinoma cell line 5637 has been added. The second stage consists in cultivating the isolated cells in a suitable culture medium, supplemented with erythropoiethin. In short, mononuclear cells were isolated from peripheral blood samples of normal donors and patients by Ficoll-Hypaque density gradient centrifugation and seeded in alpha-minimal essential medium (Sigma-Aldrich) supplemented with 10% FBS (Analitica de Mori), 1 µg/mL cyclosporin A (Sigma-Aldrich), and 10% conditioned medium from the 5637 bladder carcinoma cell line and 10 ng/ml stem cell factor (PeproTech EC Ltd, London, England). After 7-day incubation in this phase I culture, the non-adherent cells were harvested, washed, and recultured in fresh medium composed of α-medium, 30% FBS, 1% de-ionized bovine serum albumin (Sigma-Aldrich), $10^{-5}$ M β-mercaptoethanol, 2 mM L-glutamine, $10^{-6}$ M dexamethasone, 1 U/ml human recombinant erythropoietin (Tebu-bio, Magenta, MI, Italy) and 10 ng/ml stem cell factor. This part of the culture is referred to as phase II. Compounds were added on day 4-5 of phase II and cells were harvested on day 12. All cultures were incubated at 37° C., under an atmosphere of 5% $CO_2$ in air, with extra humidity. The expression of the genes encoding for γ-globin was evaluated by quantitative RT-PCR. The production of HbF was analyzed by HPLC.

Quantitative Real-Time RT-PCR for Analysis of Production of γ-Globin mRNA.

Total RNA was extracted from cells by the use of TRI Reagent RNA isolation Reagent (Sigma Aldrich). All solutions and laboratory equipment were certified RNAse free. Following the manufacturers instructions, 1 mL of the reagent was added to $5*10^6$ cells. After a 3 minute incubation at room temperature, 20 µg of glycogen and 200 µL of chloroform were added. The samples were then centrifuged and the aqueous phase recovered. This phase was diluted with one volume of isopropanol and centrifuged at 4° C. to let the RNA precipitate. After a washing step with methanol, the extracted RNA was dried and then resuspended in RNAse free water. The purified RNAs were stored at −80° C.

In order to determine the quality of the extracted RNA, electrophoresis runs on 0.8% agarose gel were carried out. The amount of the recovered RNA was quantified by its absorbance at 260 nm. Protein contamination quality control was carried out by ensuring that the 260/280 nm absorbance ratio was greater than 1.8 cDNA production from the extracted RNA was carried out as per ImProm-II™ Reverse Transcription System (Promega). 0.5 µg di RNA was retro-transcribed by using random hexamer. The produced cDNA was then stored at −80° C. until use.

The expression of the genes encoding for γ-globin was evaluated by quantitative RT-PCR, using the following primer and probe oligonucleotides (FAM=6-carboxy fluorescein, TAMRA=6-carboxy-N,N,N',N'-tetramethyl-rhodamine):

```
(γ-globin forward primer)
5'-TGG CAA GAA GGT GCT GAC TTC-3';

(γ-globin REVERSE primer)
5'-TCA CTC AGC TGG GCA AAG G-3';

(γ-globin probe)
5'-FAM-TGG GAG ATG CCA TAA AGC ACC TGG-TAMRA-3'.
```

For real-time PCR analysis we used as reference gene the endogenous control human GAPDH kit (Applied Biosystems).

High Performance Liquid Chromatography for Analysis of Production of HbF.

Human erythroid precursor cells were harvested, washed once with PBS and the pellets were lysed in lysis buffer (sodium dodecyl sulphate 0.01%). After incubation on ice for 15 minutes, and centrifugation for 5 minutes at 14,000 rpm in a microcentrifuge, the supernatant was separated from the membrane debris and injected. Hb proteins present in the lysates were separated by cation-exchange HPLC, using a Beckman Coulter instrument System Gold 126 Solvent Module-166 Detector. Hemoglobins were separated using a Syncropak CCM 103/25 (250 mm×4.6 mm) column, samples were eluted in a solvent gradient utilizing aqueous sodium acetate-BisTris-KCN buffers and detection was performed at 415 nm. The standard controls were the purified HbA (SIGMA, St Louis, Mo., USA) and HbF (Alpha Wassermann, Milano, Italy).

Studies Using Pooled Rat, Mouse or Human Liver Microsomes

Assays were performed in presence of 0.5 mg/ml of microsomal protein, with a NADPH-generating system (1 mM NADP, 2.5 mM glucose 6-phosphate and 2 U/ml glucose 6-phosphate dehydrogenase) in 100 mM potassium phosphate buffer containing 3.3 mM $MgCl_2$ (pH 7.4). Tested compounds were stored in 10 mM DMSO solution and incubated at 1 µM final concentration (final DMSO concentration in incubation less than 0.1%). Microsomes and substrates were preincubated at 37° C. for 5 min and then the enzymatic reactions were initiated by the addition of cofactors and incubated at 37° C. for up to 90 min. Incubations were terminated by the addition of an equivalent volume of cold acetonitrile containing I.S. Control incubations, where the substrate was incubated in the same buffer system containing pRLM without the NADPH-generating system, were also run.

Rat PK Studies

Rats Male Sprague-Dawley rats (250-350 g) were used for the absorption disposition studies. In each rat an indwelling cannula was implanted in the right jugular vein for blood sampling. The surgery was performed under light anaesthesia (Ketamine-Xilazine (85 mg/kg and 2.5 mg/kg respectively i.m.) one day prior the experiment). During the kinetic study, all animals were housed individually in plastic metabolism cages, and were unrestrained throughout the experiment. Compounds (6 mg/mL) were dissolved in 20% DMSO/60% PEG400/20% water for intravenous administration, and dissolved or suspended in 1% methylcellulose for oral administration (2 mg/ml). After an overnight fast, the rats received an i.v. (via caudal vein) or an oral dose of the compound. Blood samples were collected at different times point after dosing. Plasma was separated immediately after blood sampling by centrifugation, and the plasma samples were kept frozen (−20° C.) until assayed by LC/MS/MS.

Analytical procedures: Plasma samples were extracted using Liquid Handling Robot MultiProbe Packard by protein precipitation with acetonitrile. Then the samples were centrifuged (3000 rpm×15 min at 4° C.) and the supernatant transferred and dried under nitrogen. The samples were reconstituted in water/acetonitrile 90/10 and then injected directly into an HPLC column. Sample analyses were performed using a an API 3000 or/and API 2000 or/and API 4000 Mass Spectrometer interfaced via the Turbo Ion Spray (ESI)/APCI to an LC system consisting of an HTS PAL CTC autosampler and an Agilen HP 1100 Binary Pump. The results are calculated using Analyst Software linear regression with $1/x*x$ weighting. The Assay Precision was calculated for the Quality Controls by Watson Lims database.

Pharmacokinetic Analysis: The plasma clearance (CLp) of the compounds were calculated (using Watson PK program) as the dose divided by the area under the plasma concentration-time curve from time zero to infinity (AUC0-∞). The apparent half-life was estimated from the slope of the terminal phase of the log plasma concentration-time data. The volume of distribution (Vdss) was determined using the following noncompartmental method:

$$Vdss=(\text{Dose IV} \times \text{AUMC})/(\text{AUC}_{0-\infty})2$$

where AUMC is the total area under the first moment of the drug concentration time curve from time zero to infinity. Bioavailability was estimated as the $\text{AUC}_{0-\infty}$ ratio following oral and intravenous administration, normalized for differences in dose.

Results

The exemplified compounds described herein were tested in the HDAC assays described above, and were found to have an $IC_{50}$ value less than 10 µM.

The compounds of the invention were tested in the HbF activation assay on K562, as model system for screening of potential inducers of fetal hemoglobin. Results show an appreciable reporter accumulation effect with EC50s in the order of high nanomolar.

Results are reported in the following Table 2.

TABLE 2

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 1 | (S)-2-(5-methoxy-2-methyl-1H-indol-3-yl)-N-(1-(5-(2-methoxyquinolin-3-yl)oxazol-2-yl)-7-oxononyl)acetamide | 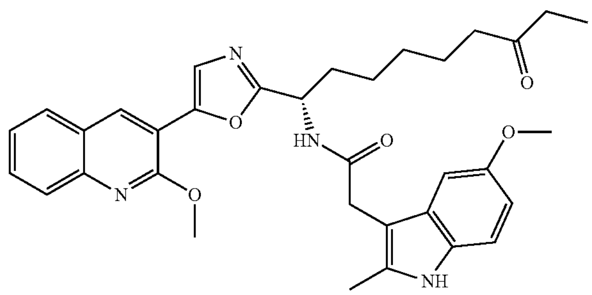 [SMILES: CCC(=O)CCCCC[C@H](NC(=O)Cc1c(C)[nH]c2ccc(OC)cc12)c1ncc(-c2cc3ccccc3nc2OC)o1] | C | A | B |
| 2 | (S)-N-(1-(5-(2-methoxyquinolin-3-yl)oxazol-2-yl)-7-oxononyl)-1-methylazetidine-3-carboxamide | 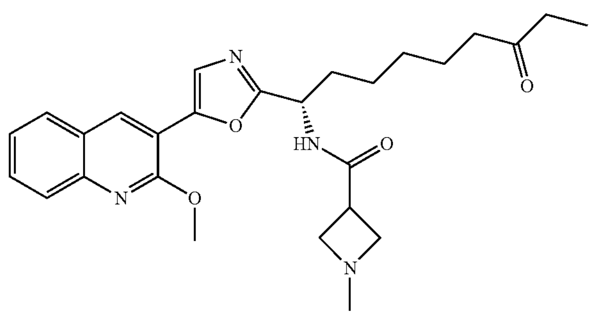 [SMILES: CCC(=O)CCCCC[C@H](NC(=O)C1CN(C)C1)c1ncc(-c2cc3ccccc3nc2OC)o1] | B | A | A |
| 3 | (S)-1-methyl-N-(7-oxo-1-(5-phenyloxazol-2-yl)nonyl)piperidine-4-carboxamide | 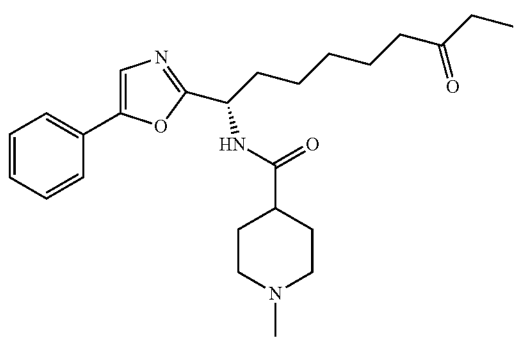 [SMILES: CCC(=O)CCCCC[C@H](NC(=O)C1CCN(C)CC1)c1ncc(-c2ccccc2)o1] | C | A | C |
| 4 | (S)-2-(5-methoxy-2-methyl-1H-indol-3-yl)-N-(7-oxo-1-(5-phenyloxazol-2-yl)nonyl)acetamide | 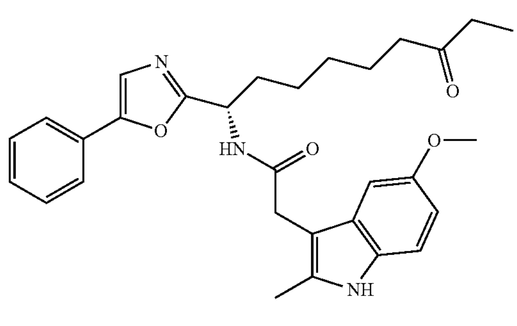 [SMILES: CCC(=O)CCCCC[C@H](NC(=O)Cc1c(C)[nH]c2ccc(OC)cc12)c1ncc(-c2ccccc2)o1] | C | A | C |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 5 | ((S)-N-(1-(5-(2,3-dihydrobenzo[b][1,4]dioxin-5-yl)oxazol-2-yl)-7-oxononyl)-1-methylpiperidine-4-carboxamide | 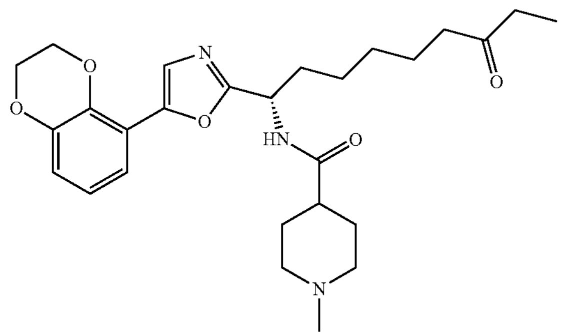 [SMILES: CCC(=O)CCCCC[C@H](NC(=O)C1CCN(C)CC1)c1ncc(-c2cccc3c2OCCO3)o1] | C | A | C |
| 6 | (S)-N-(7-oxo-1-(5-phenyloxazol-2-yl)nonyl)thiazole-5-carboxamide | 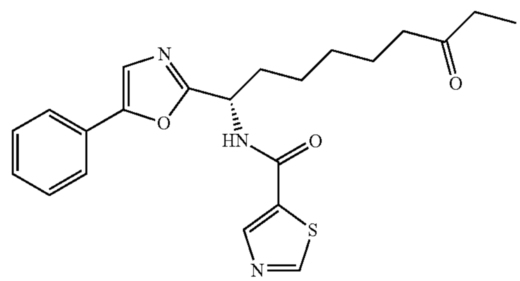 [SMILES: CCC(=O)CCCCC[C@H](NC(=O)c1cncs1)c1ncc(-c2ccccc2)o1] | C | A | C |
| 7 | (S)-3-(dimethylamino)-N-(7-oxo-1-(5-phenyloxazol-2-yl)nonyl)propanamide | 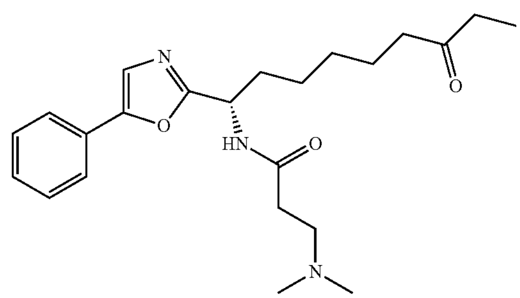 [SMILES: CCC(=O)CCCCC[C@H](NC(=O)CCN(C)C)c1ncc(-c2ccccc2)o1] | C | A | C |
| 8 | 1-methyl-N-((S)-7-oxo-1-(5-phenyloxazol-2-yl)nonyl)pyrrolidine-3-carboxamide | 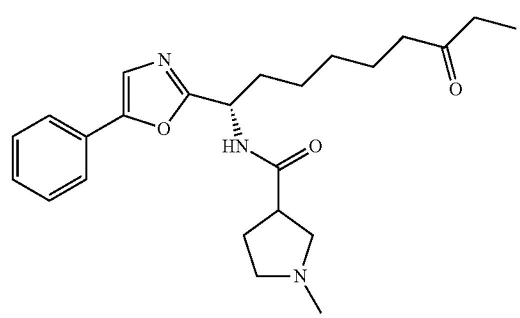 [SMILES: CCC(=O)CCCCC[C@H](NC(=O)C1CCN(C)C1)c1ncc(-c2ccccc2)o1] | C | A | C |
| 9 | (S)-2-(dimethylamino)-2-methyl-N-(7-oxo-1-(5-phenyloxazol-2-yl)nonyl)propanamide | 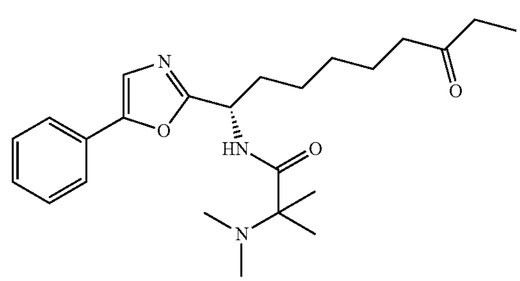 [SMILES: CCC(=O)CCCCC[C@H](NC(=O)C(C)(C)N(C)C)c1ncc(-c2ccccc2)o1] | C | A | C |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 13 | (R)-2-oxo-N-((S)-7-oxo-1-(5-phenyloxazol-2-yl)nonyl)thiazolidine-4-carboxamide | 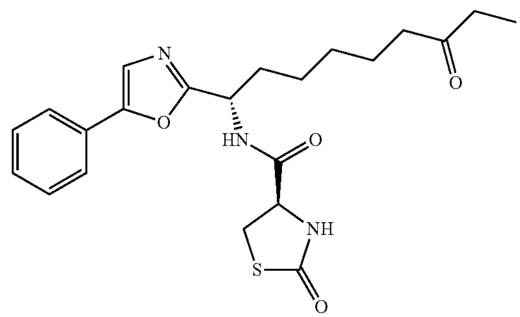 [SMILES: CCC(=O)CCCCC[C@H](NC(=O)[C@@H]1CSC(=O)N1)c1ncc(-c2ccccc2)o1] | C | A | C |
| 14 | (S)-2-chloro-N-(7-oxo-1-(5-phenyloxazol-2-yl)nonyl)isonicotinamide | 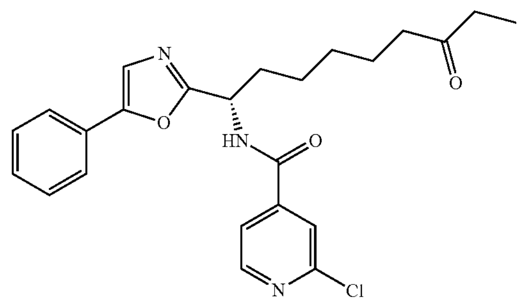 [SMILES: CCC(=O)CCCCC[C@H](NC(=O)c1ccnc(Cl)c1)c1ncc(-c2ccccc2)o1] | C | B | C |
| 15 | (S)-2-(4-methylpiperazin-1-yl)-N-(7-oxo-1-(5-phenyloxazol-2-yl)nonyl)acetamide | 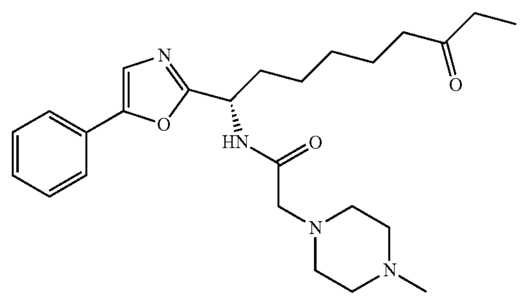 [SMILES: CCC(=O)CCCCC[C@H](NC(=O)CN1CCN(C)CC1)c1ncc(-c2ccccc2)o1] | C | B | C |
| 18 | (S)-2-(2-methyl-1H-benzo[d]imidazol-1-yl)-N-(7-oxo-1-(5-phenyloxazol-2-yl)nonyl)acetamide | 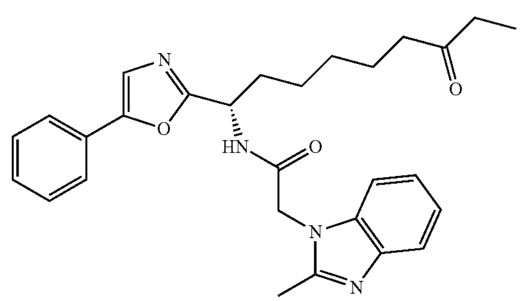 [SMILES: CCC(=O)CCCCC[C@H](NC(=O)Cn1c(C)nc2ccccc21)c1ncc(-c2ccccc2)o1] | C | B | C |
| 21 | 1-methyl-N-((S)-7-oxo-1-(5-phenyloxazol-2-yl)nonyl)azepane-2-carboxamide | 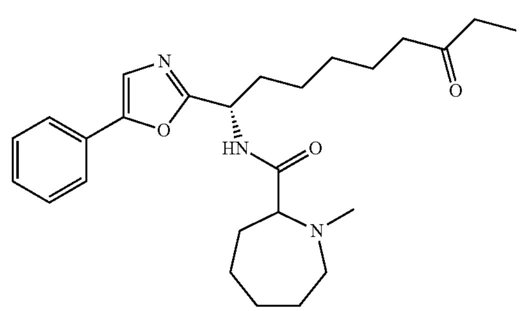 [SMILES: CCC(=O)CCCCC[C@H](NC(=O)C1CCCCCN1C)c1ncc(-c2ccccc2)o1] | C | B | C |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 25 | 3-(1-methylpiperidin-3-yl)-N-((S)-7-oxo-1-(5-phenyloxazol-2-yl)nonyl)propanamide | 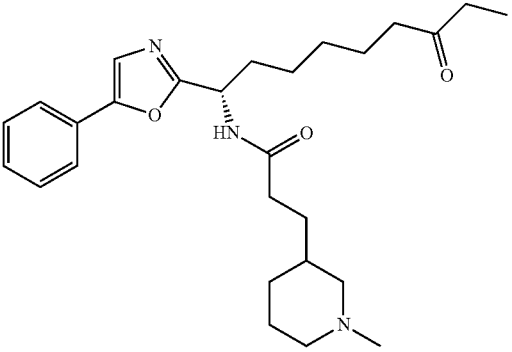 [SMILES: CCC(=O)CCCCC[C@H](NC(=O)CCC1CCCN(C)C1)c1ncc(-c2ccccc2)o1] | C | B | C |
| 26 | (S)-3-(2-ethyl-1H-benzo[d]imidazol-1-yl)-N-(7-oxo-1-(5-phenyloxazol-2-yl)nonyl)propanamide | 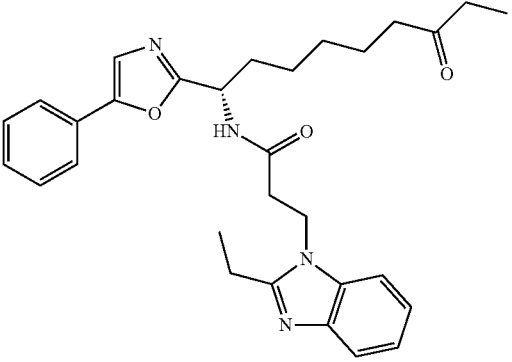 [SMILES: CCC(=O)CCCCC[C@H](NC(=O)CCn1c(CC)nc2ccccc21)c1ncc(-c2ccccc2)o1] | C | B | C |
| 29 | (S)-3-(2-ethyl-1H-benzo[d]imidazol-1-yl)-N-(1-(5-(2-methoxyquinolin-3-yl)oxazol-2-yl)-7-oxononyl)propanamide | 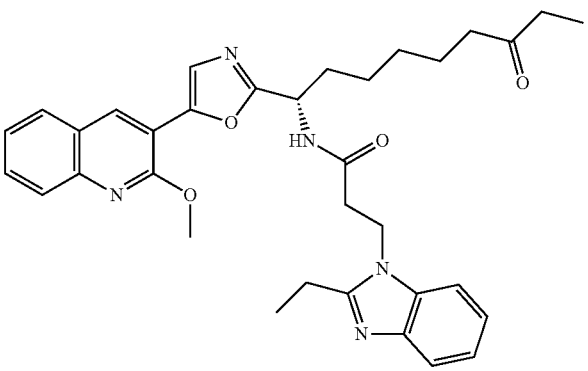 [SMILES: CCC(=O)CCCCC[C@H](NC(=O)CCn1c(CC)nc2ccccc21)c1ncc(-c2cc3ccccc3nc2OC)o1] | B | A | A |
| 32 | (S)-1-methyl-N-(7-oxo-1-(5-phenyloxazol-2-yl)nonyl)azetidine-3-carboxamide | 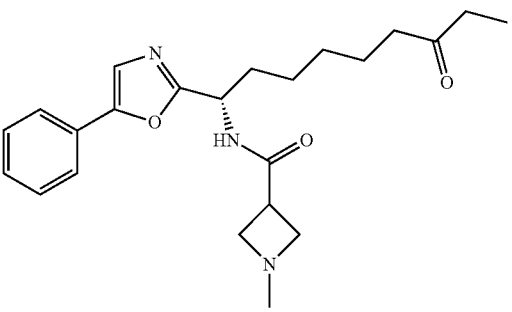 [SMILES: CCC(=O)CCCCC[C@H](NC(=O)C1CN(C)C1)c1ncc(-c2ccccc2)o1] | C | A | C |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 34 | N-((S)-1-(5-(2-methoxyquinolin-3-yl)oxazol-2-yl)-7-oxononyl)-1-methylpyrrolidine-3-carboxamide | 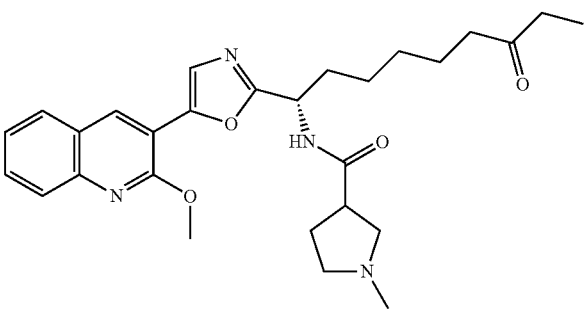 [SMILES: CCC(=O)CCCCC[C@H](NC(=O)C1CCN(C)C1)c1ncc(-c2cc3ccccc3nc2OC)o1] | B | A | B |
| 35 | (S)-2-(dimethylamino)-N-(1-(5-(2-methoxyquinolin-3-yl)oxazol-2-yl)-7-oxononyl)-2-methylpropanamide | 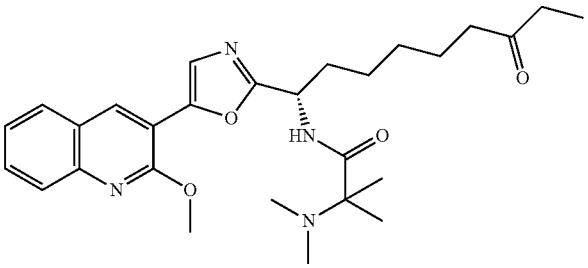 [SMILES: CCC(=O)CCCCC[C@H](NC(=O)C(C)(C)N(C)C)c1ncc(-c2cc3ccccc3nc2OC)o1] | B | A | A |
| 36 | (S)-N1-(1-(5-(2-methoxyquinolin-3-yl)oxazol-2-yl)-7-oxononyl)-N2,N2-dimethyloxalamide | 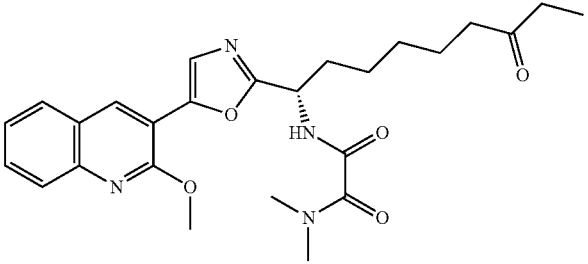 | C | B | B |
| 37 | (S)-N-(1-(5-(2-methoxyquinolin-3-yl)oxazol-2-yl)-7-oxononyl)-2-(4-methylpiperazin-1-yl)-2-oxoacetamide | 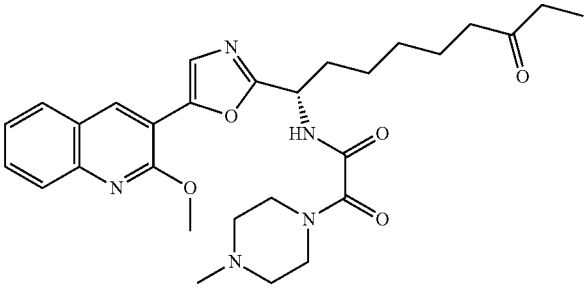 [SMILES: CCC(=O)CCCCC[C@H](NC(=O)C(=O)N1CCN(C)CC1)c1ncc(-c2cc3ccccc3nc2OC)o1] | C | A | B |
| 38 | (S)-3-(dimethylamino)-N-(1-(5-(2-methoxyquinolin-3-yl)oxazol-2-yl)-7-oxononyl)propanamide | 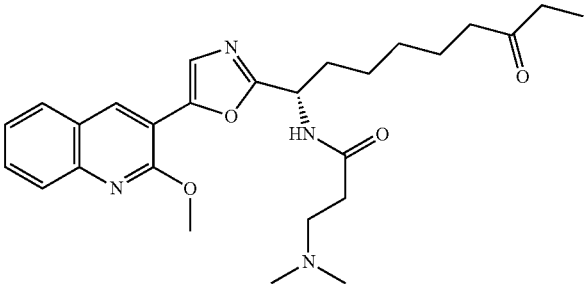 [SMILES: CCC(=O)CCCCC[C@H](NC(=O)CCN(C)C)c1ncc(-c2cc3ccccc3nc2OC)o1] | B | A | A |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 39 | (S)-9-((2-(dimethylamino)ethyl)amino)-9-(5-(2-methoxyquinolin-3-yl)oxazol-2-yl)nonan-3-one | 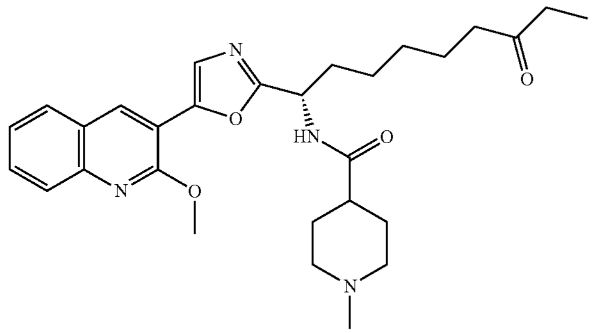 | B | A | A |
| 40 | (S)-N-(1-(5-(2-methoxyquinolin-3-yl)oxazol-2-yl)-7-oxononyl)thiazole-5-carboxamide | 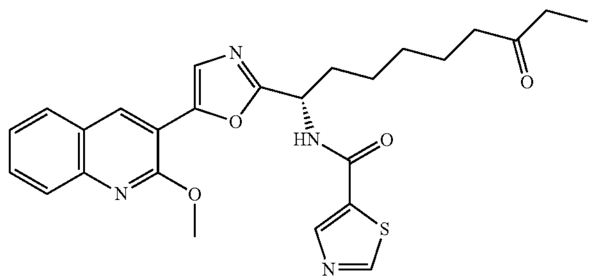 [SMILES: CCC(=O)CCCCC[C@H](NC(=O)c1cncs1)c1ncc(-c2cc3ccccc3nc2OC)o1] | C | A | A |
| 41 | (S)-N-(1-(5-(2-methoxyquinolin-3-yl)oxazol-2-yl)-7-oxononyl)quinuclidine-4-carboxamide | 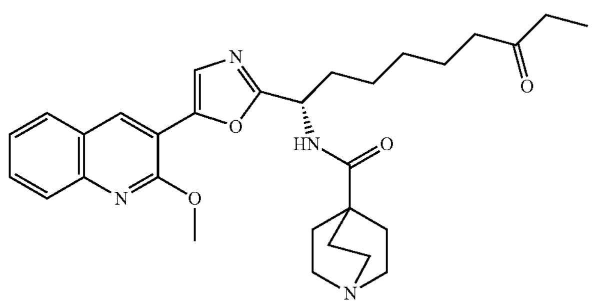 [SMILES: CCC(=O)CCCCC[C@H](NC(=O)C12CCN(CC1)CC2)c1ncc(-c2cc3ccccc3nc2OC)o1] | C | A | A |
| 42 | (R)-N-(1-(5-(2-methoxyquinolin-3-yl)oxazol-2-yl)-7-oxononyl)-1-methylazetidine-3-carboxamide | 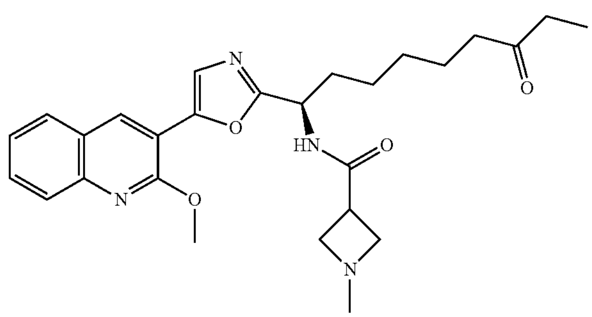 [SMILES: CCC(=O)CCCCC[C@@H](NC(=O)C1CN(C)C1)c1ncc(-c2cc3ccccc3nc2OC)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 44 | (S)-1-methyl-N-(7-oxo-1-(5-(2-oxo-1,2-dihydroquinolin-3-yl)oxazol-2-yl)nonyl)azetidine-3-carboxamide | 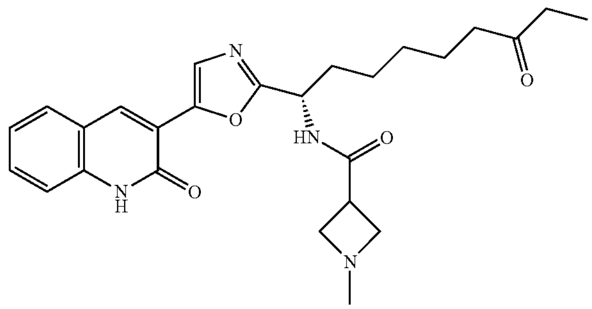 [SMILES: CCC(=O)CCCCC[C@H](NC(=O)C1CN(C)C1)c1ncc(-c2cc3ccccc3[nH]c2=O)o1] | B | A | A |
| 45 | (S)-N1-(1-(5-(2-methoxyquinolin-3-yl)-1,3,4-oxadiazol-2-yl)-7-oxononyl)-N2,N2-dimethyloxalamide | 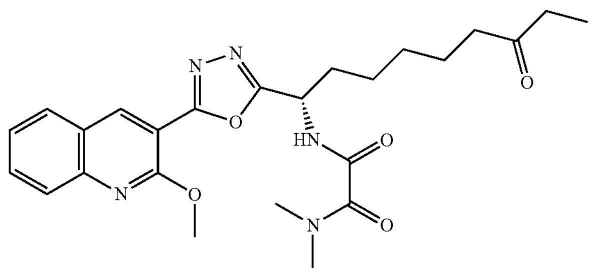 [SMILES: CCC(=O)CCCCC[C@H](NC(=O)C(=O)N(C)C)c1nnc(-c2cc3ccccc3nc2OC)o1] | C | A | B |
| 46 | (S)-N-(1-(5-(2-methoxyquinolin-3-yl)-1,3,4-oxadiazol-2-yl)-7-oxononyl)-2-(4-methylpiperazin-1-yl)-2-oxoacetamide | 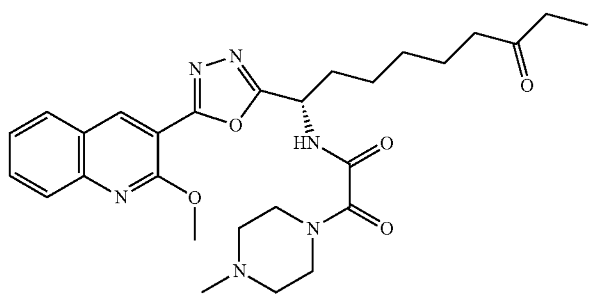 | C | A | B |
| 47 | (S)-N-(1-(5-(2-methoxyquinolin-3-yl)-1,3,4-oxadiazol-2-yl)-7-oxononyl)-1-methylpiperidine-4-carboxamide | 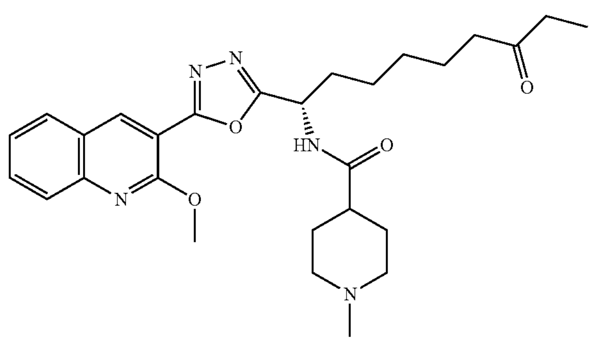 [SMILES: CCC(=O)CCCCC[C@H](NC(=O)C1CCN(C)CC1)c1nnc(-c2cc3ccccc3nc2OC)o1] | B | A | B |
| 48 | (S)-2-(5-methoxy-2-methyl-1H-indol-3-yl)-N-(1-(5-(2-methoxyquinolin-3-yl)-1,3,4-oxadiazol-2-yl)-7-oxononyl)acetamide | 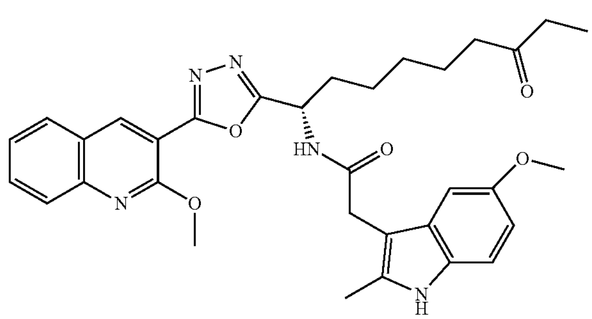 [SMILES: CCC(=O)CCCCC[C@H](NC(=O)Cc1c(C)[nH]c2ccc(OC)cc12)c1nnc(-c2cc3ccccc3nc2OC)o1] | C | A | A |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 49 | (S)-N-(1-(5-(2-methoxyquinolin-3-yl)-1,3,4-oxadiazol-2-yl)-7-oxononyl)thiazole-5-carboxamide | 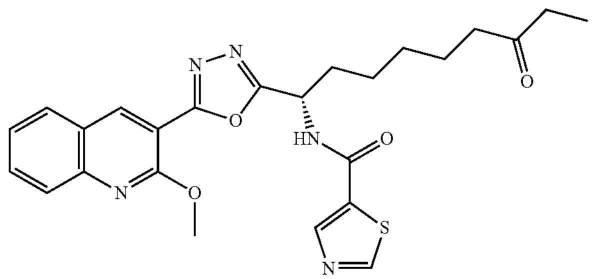 [SMILES: CCC(=O)CCCCC[C@H](NC(=O)c1cncs1)c1nnc(-c2cc3ccccc3nc2OC)o1] | C | A | B |
| 50 | (S)-3-(2-ethyl-1H-benzo[d]imidazol-1-yl)-N-(1-(5-(2-methoxyquinolin-3-yl)-1,3,4-oxadiazol-2-yl)-7-oxononyl)propanamide | 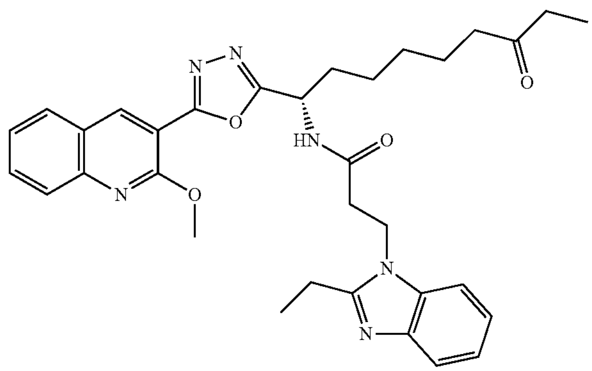 [SMILES: CCC(=O)CCCCC[C@H](NC(=O)CCn1c(CC)nc2ccccc21)c1nnc(-c2cc3ccccc3nc2OC)o1] | B | A | B |
| 51 | (S)-3-(dimethylamino)-N-(1-(5-(2-methoxyquinolin-3-yl)-1,3,4-oxadiazol-2-yl)-7-oxononyl)propanamide | 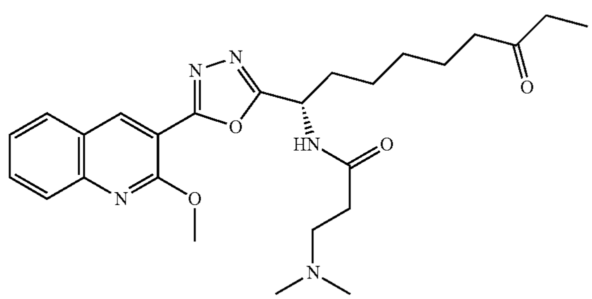 [SMILES: CCC(=O)CCCCC[C@H](NC(=O)CCN(C)C)c1nnc(-c2cc3ccccc3nc2OC)o1] | C | A | B |
| 52 | (S)-N-(1-(5-(2-methoxyquinolin-3-yl)-1,3,4-oxadiazol-2-yl)-7-oxononyl)-1-methylazetidine-3-carboxamide | 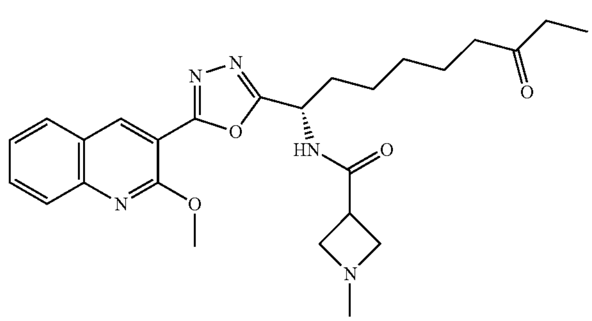 [SMILES: CCC(=O)CCCCC[C@H](NC(=O)C1CN(C)C1)c1nnc(-c2cc3ccccc3nc2OC)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 53 | (S)-N-(1-(5-(4-(1H-pyrazol-5-yl)phenyl)oxazol-2-yl)-7-oxononyl)-1-methylazetidine-3-carboxamide | 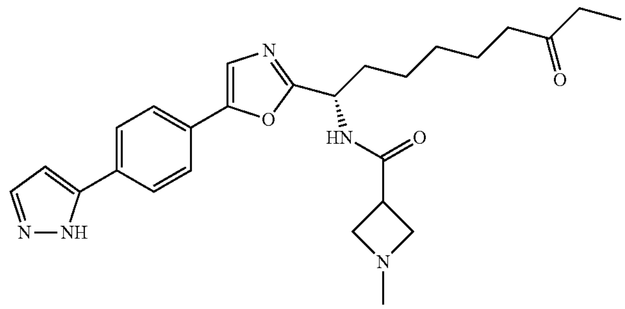 [SMILES: CCC(=O)CCCCC[C@H](NC(=O)C1CN(C)C1)c1ncc(-c2ccc(-c3ccn[nH]3)cc2)o1] | C | A | B |
| 54 | (S)-1-methyl-N-(1-(5-(4-(1-methyl-1H-pyrazol-5-yl)phenyl)oxazol-2-yl)-7-oxononyl)azetidine-3-carboxamide | 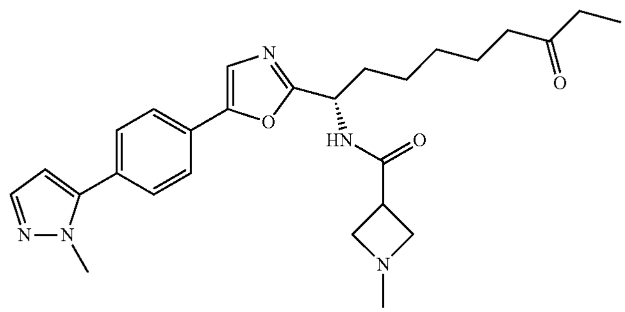 [SMILES: CCC(=O)CCCCC[C@H](NC(=O)C1CN(C)C1)c1ncc(-c2ccc(-c3ccnn3C)cc2)o1] | C | A | B |
| 55 | (S)-1-acetyl-N-(1-(5-(2-methoxyquinolin-3-yl)oxazol-2-yl)-7-oxononyl)azetidine-3-carboxamide | 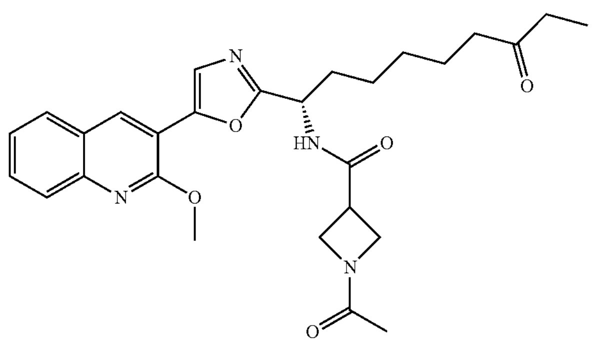 [SMILES: CCC(=O)CCCCC[C@H](NC(=O)C1CN(C(C)=O)C1)c1ncc(-c2cc3ccccc3nc2OC)o1] | C | A | B |
| 56 | (S)-1-benzyl-N-(1-(5-(2-methoxyquinolin-3-yl)oxazol-2-yl)-7-oxononyl)azetidine-3-carboxamide | 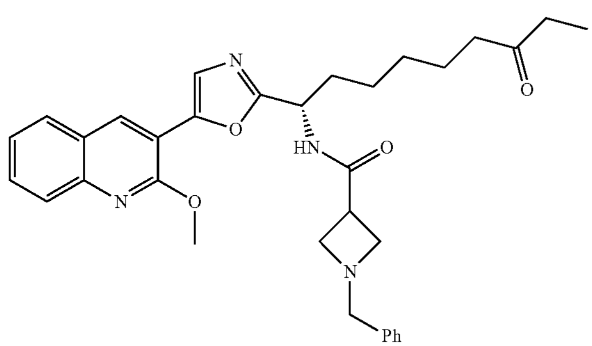 [SMILES: CCC(=O)CCCCC[C@H](NC(=O)C1CN(Cc2ccccc2)C1)c1ncc(-c2cc3ccccc3nc2OC)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 57 | (S)-N-(1-(5-(2-methoxyquinolin-3-yl)oxazol-2-yl)-7-oxononyl)azetidine-3-carboxamide | 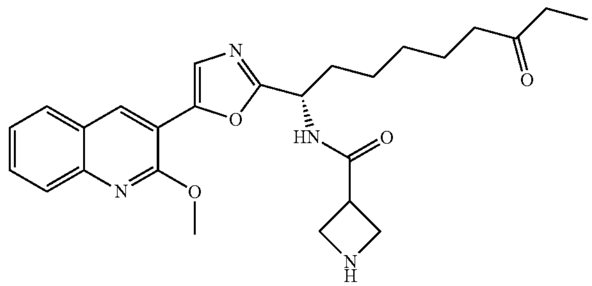 [SMILES: CCC(=O)CCCCC[C@H](NC(=O)C1CNC1)c1ncc(-c2cc3ccccc3nc2OC)o1] | C | A | B |
| 58 | (S)-4,4-difluoro-N-((S)-1-(5-(2-methoxyquinolin-3-yl)oxazol-2-yl)-7-oxononyl)-1-methylpyrrolidine-2-carboxamide | 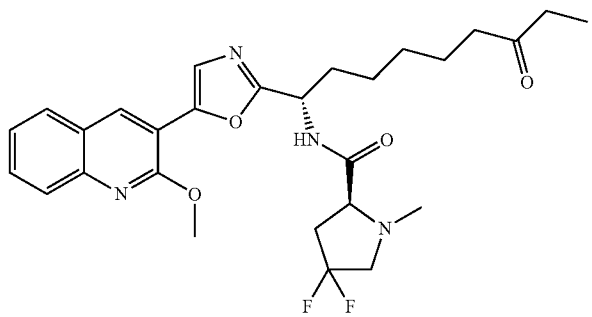 [SMILES: CCC(=O)CCCCC[C@H](NC(=O)[C@@H]1CC(F)(F)CN1C)c1ncc(-c2cc3ccccc3nc2OC)o1] | C | A | B |
| 59 | (S)-N-(1-(5-(2-methoxyquinolin-3-yl)oxazol-2-yl)-7-oxononyl)-2-(1H-1,2,3-triazol-1-yl)acetamide | 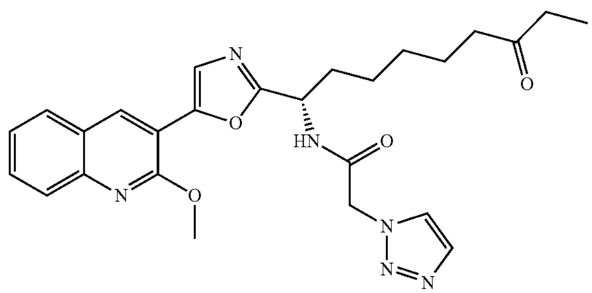 [SMILES: CCC(=O)CCCCC[C@H](NC(=O)Cn1ccnn1)c1ncc(-c2cc3ccccc3nc2OC)o1] | C | A | B |
| 60 | (S)-4,4-difluoro-N-((S)-1-(5-(2-methoxyquinolin-3-yl)oxazol-2-yl)-7-oxononyl)pyrrolidine-2-carboxamide | 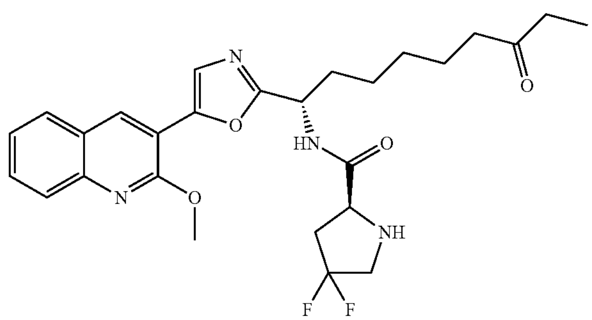 [SMILES: CCC(=O)CCCCC[C@H](NC(=O)[C@@H]1CC(F)(F)CN1)c1ncc(-c2cc3ccccc3nc2OC)o1] | C | A | C |
| 61 | (S)-N-(1-(5-(4-(1H-pyrazol-1-yl)phenyl)oxazol-2-yl)-7-oxononyl)-1-methylazetidine-3-carboxamide | 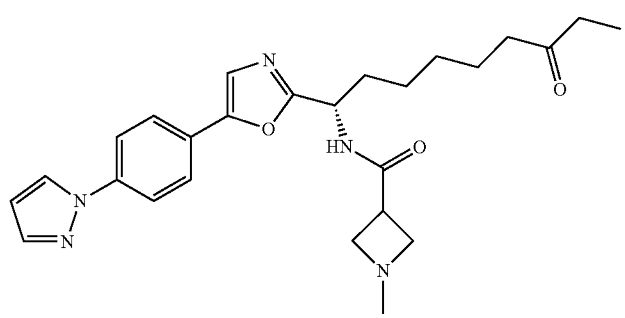 [SMILES: CCC(=O)CCCCC[C@H](NC(=O)C1CN(C)C1)c1ncc(-c2ccc(-n3cccn3)cc2)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 62 | (S)-N-(1-(5-(4-(1H-pyrazol-1-yl)phenyl)oxazol-2-yl)-7-oxononyl)-1-acetylazetidine-3-carboxamide | 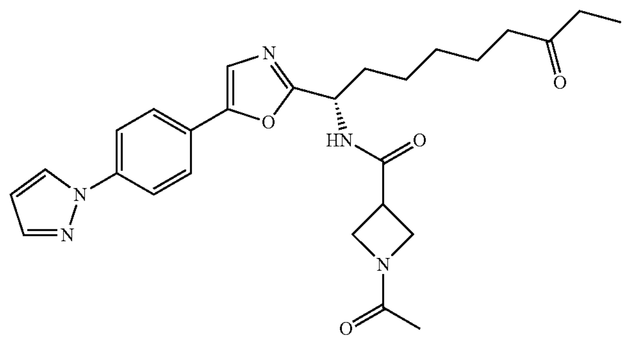 [SMILES: CCC(=O)CCCCC[C@H](NC(=O)C1CN(C(C)=O)C1)c1ncc(-c2ccc(-n3cccn3)cc2)o1] | C | A | B |
| 63 | (S)-2-(dimethylamino)-4,4,4-trifluoro-N-((S)-1-(5-(2-methoxyquinolin-3-yl)oxazol-2-yl)-7-oxononyl)butanamide | 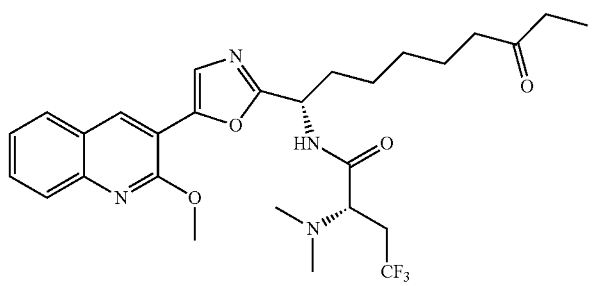 [SMILES: CCC(=O)CCCCC[C@H](NC(=O)[C@H](CC(F)(F)F)N(C)C)c1ncc(-c2cc3ccccc3nc2OC)o1] | C | B | C |
| 64 | (R)-2-(dimethylamino)-4,4,4-trifluoro-N-((S)-1-(5-(2-methoxyquinolin-3-yl)oxazol-2-yl)-7-oxononyl)butanamide | 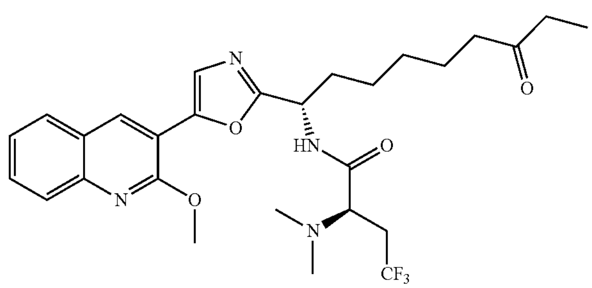 [SMILES: CCC(=O)CCCCC[C@H](NC(=O)[C@@H](CC(F)(F)F)N(C)C)c1ncc(-c2cc3ccccc3nc2OC)o1] | C | A | C |
| 65 | (S)-N-(1-(5-(4-(6-methoxypyridin-3-yl)phenyl)oxazol-2-yl)-7-oxononyl)-1-methylazetidine-3-carboxamide | 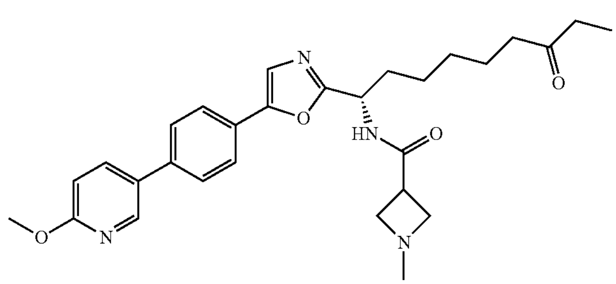 [SMILES: CCC(=O)CCCCC[C@H](NC(=O)C1CN(C)C1)c1ncc(-c2ccc(-c3ccc(OC)nc3)cc2)o1] | C | A | B |
| 66 | (2S,4S)-4-fluoro-N-((S)-1-(5-(2-methoxyquinolin-3-yl)oxazol-2-yl)-7-oxononyl)-1-methylpyrrolidine-2-carboxamide | 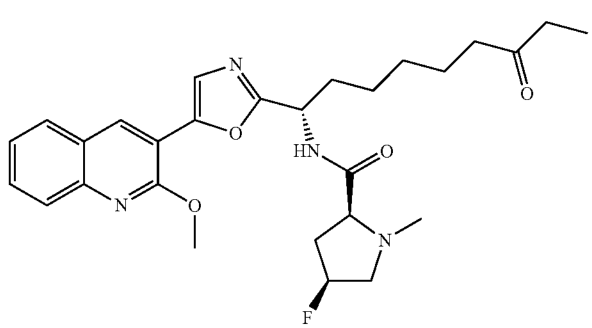 [SMILES: CCC(=O)CCCCC[C@H](NC(=O)[C@@H]1C[C@H](F)CN1C)c1ncc(-c2cc3ccccc3nc2OC)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 67 | (S)-3-fluoro-N-(1-(5-(2-methoxyquinolin-3-yl)oxazol-2-yl)-7-oxononyl)-1-methylazetidine-3-carboxamide | 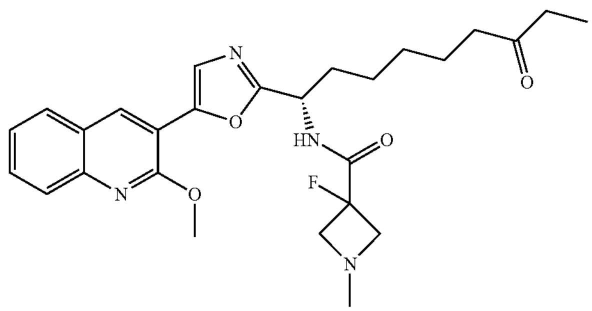 [SMILES: CCC(=O)CCCCC[C@H](NC(=O)C1(F)CN(C)C1)c1ncc(-c2cc3ccccc3nc2OC)o1] | C | A | B |
| 68 | (S)-4-fluoro-N-(1-(5-(2-methoxyquinolin-3-yl)oxazol-2-yl)-7-oxononyl)-1-methylpiperidine-4-carboxamide | 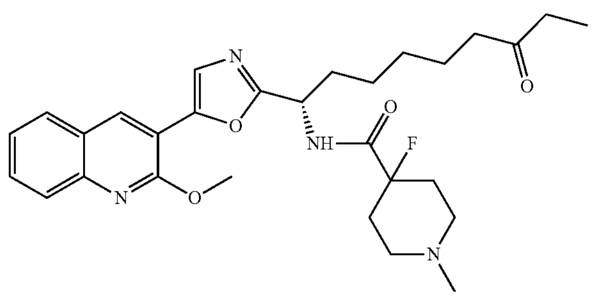 [SMILES: CCC(=O)CCCCC[C@H](NC(=O)C1(F)CCN(C)CC1)c1ncc(-c2cc3ccccc3nc2OC)o1] | C | A | B |
| 69 | (S)-N-(1-(5-(2-methoxyquinolin-3-yl)oxazol-2-yl)-7-oxononyl)-2-morpholino-2-oxoacetamide | 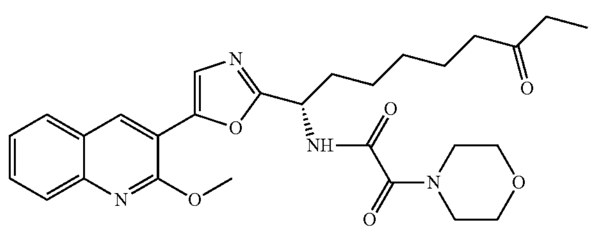 [SMILES: CCC(=O)CCCCC[C@H](NC(=O)C(=O)N1CCOCC1)c1ncc(-c2cc3ccccc3nc2OC)o1] | C | A | B |
| 70 | (S)-1-methyl-N-(7-oxo-1-(5-(quinolin-8-yl)oxazol-2-yl)nonyl)azetidine-3-carboxamide | 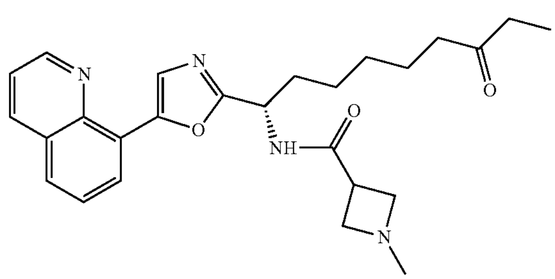 [SMILES: CCC(=O)CCCCC[C@H](NC(=O)C1CN(C)C1)c1ncc(-c2cccc3cccnc23)o1] | C | A | B |
| 71 | (S)-1-methyl-N-(1-(5-(1-methyl-2-oxo-1,2-dihydroquinolin-3-yl)-1,3,4-oxadiazol-2-yl)-7-oxononyl)azetidine-3-carboxamide | 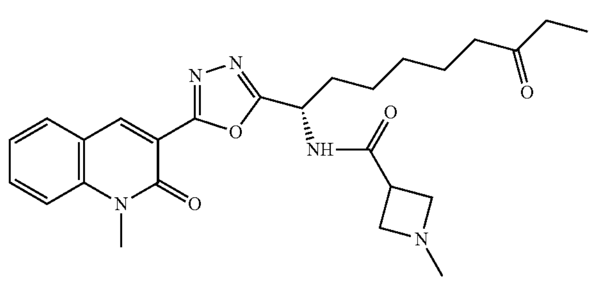 [SMILES: CCC(=O)CCCCC[C@H](NC(=O)C1CN(C)C1)c1nnc(-c2cc3ccccc3n(C)c2=O)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 72 | N-((S)-1-(5-(2-methoxyquinolin-3-yl)oxazol-2-yl)-7-oxononyl)-5-oxopyrrolidine-3-carboxamide | 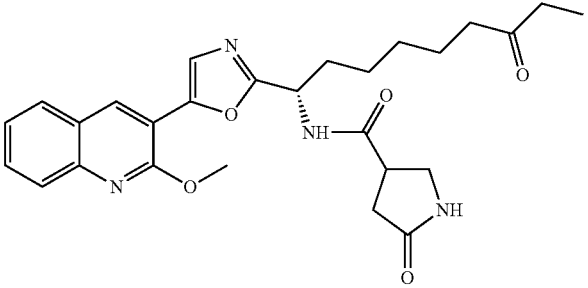 [SMILES: CCC(=O)CCCCC[C@H](NC(=O)C1CNC(=O)C1)c1ncc(-c2cc3ccccc3nc2OC)o1] | B | A | B |
| 73 | (S)-2-(1H-imidazol-4-yl)-N-(1-(5-(2-methoxyquinolin-3-yl)oxazol-2-yl)-7-oxononyl)acetamide | 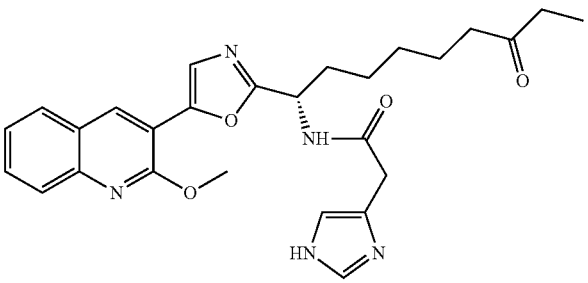 [SMILES: CCC(=O)CCCCC[C@H](NC(=O)Cc1c[nH]cn1)c1ncc(-c2cc3ccccc3nc2OC)o1] | C | A | B |
| 74 | (S)-N-(1-(5-(2-methoxyquinolin-3-yl)oxazol-2-yl)-7-oxononyl)-2-(pyridin-3-yl)acetamide | 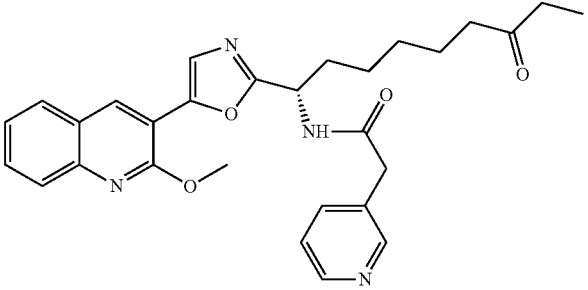 [SMILES: CCC(=O)CCCCC[C@H](NC(=O)Cc1cccnc1)c1ncc(-c2cc3ccccc3nc2OC)o1] | C | A | B |
| 75 | (S)-3-(1H-imidazol-1-yl)-N-(1-(5-(2-methoxyquinolin-3-yl)oxazol-2-yl)-7-oxononyl)propanamide | 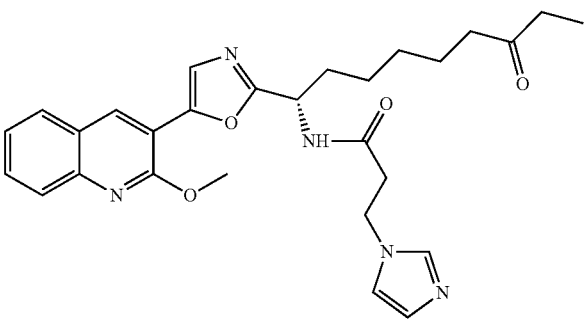 [SMILES: CCC(=O)CCCCC[C@H](NC(=O)CCn1ccnc1)c1ncc(-c2cc3ccccc3nc2OC)o1] | B | A | B |
| 76 | (S)-N-(1-(5-(2-methoxyquinolin-3-yl)oxazol-2-yl)-7-oxononyl)-2-(thiazol-2-yl)acetamide | 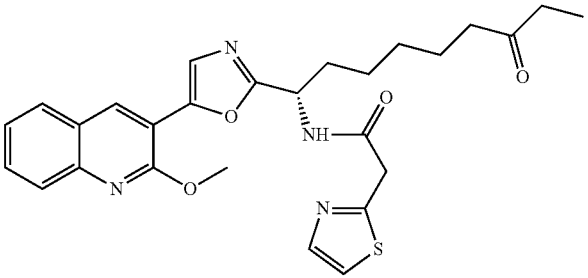 [SMILES: CCC(=O)CCCCC[C@H](NC(=O)Cc1nccs1)c1ncc(-c2cc3ccccc3nc2OC)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 77 | (S)-N-(1-(5-(2-methoxyquinolin-3-yl)oxazol-2-yl)-7-oxononyl)-2-(4-methyl-1,2,5-oxadiazol-3-yl)acetamide | 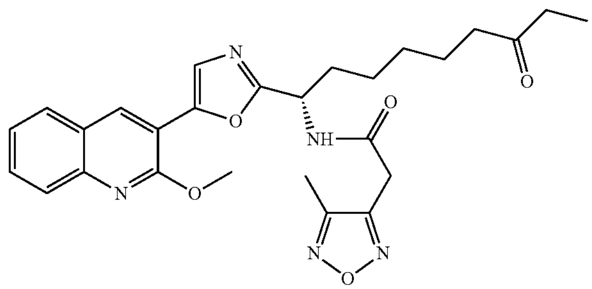 [SMILES: CCC(=O)CCCCC[C@H](NC(=O)Cc1nonc1C)c1ncc(-c2cc3ccccc3nc2OC)o1] | C | A | B |
| 78 | (S)-N-(1-(5-(2-methoxyquinolin-3-yl)oxazol-2-yl)-7-oxononyl)-2-(3-methyl-1H-pyrazol-1-yl)acetamide | 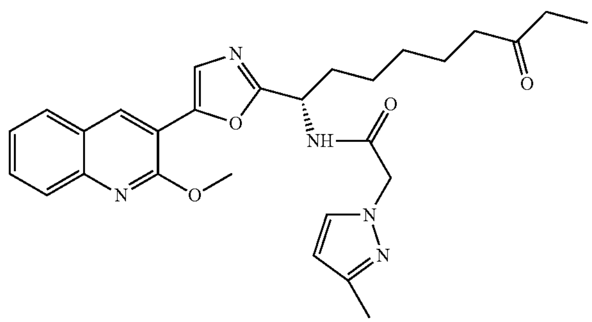 [SMILES: CCC(=O)CCCCC[C@H](NC(=O)Cn1ccc(C)n1)c1ncc(-c2cc3ccccc3nc2OC)o1] | C | A | B |
| 79 | (S)-N-(1-(5-(2-methoxyquinolin-3-yl)oxazol-2-yl)-7-oxononyl)-2-(pyrimidin-2-yl)acetamide | 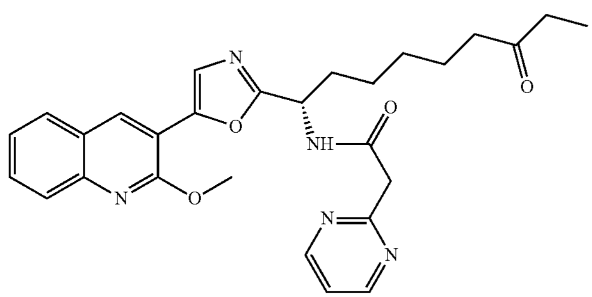 [SMILES: CCC(=O)CCCCC[C@H](NC(=O)Cc1ncccn1)c1ncc(-c2cc3ccccc3nc2OC)o1] | C | A | B |
| 80 | (S)-2-(3,5-dimethyl-1H-1,2,4-triazol-1-yl)-N-(1-(5-(2-methoxyquinolin-3-yl)oxazol-2-yl)-7-oxononyl)acetamide | 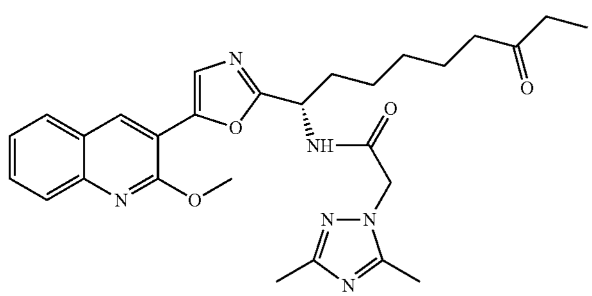 [SMILES: CCC(=O)CCCCC[C@H](NC(=O)Cn1nc(C)nc1C)c1ncc(-c2cc3ccccc3nc2OC)o1] | B | A | B |
| 81 | (S)-2-(3,5-dimethyl-1H-pyrazol-1-yl)-N-(1-(5-(2-methoxyquinolin-3-yl)oxazol-2-yl)-7-oxononyl)acetamide | 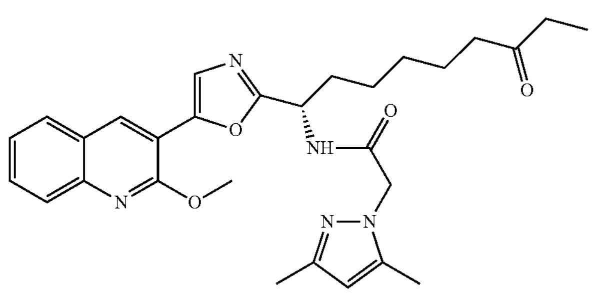 [SMILES: CCC(=O)CCCCC[C@H](NC(=O)Cn1nc(C)cc1C)c1ncc(-c2cc3ccccc3nc2OC)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 82 | (S)-N-(1-(5-(2-methoxyquinolin-3-yl)oxazol-2-yl)-7-oxononyl)-2-(pyrrolidin-1-ylmethyl)thiazole-5-carboxamide | 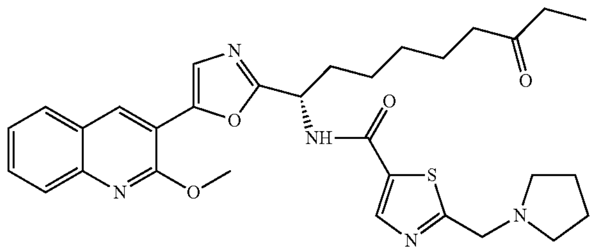 [SMILES: CCC(=O)CCCCC[C@H](NC(=O)c1cnc(CN2CCCC2)s1)c1ncc(-c2cc3ccccc3nc2OC)o1] | B | A | A |
| 83 | (S)-N-(1-(5-(2-methoxyquinolin-3-yl)oxazol-2-yl)-7-oxononyl)-2,4-dimethylthiazole-5-carboxamide | 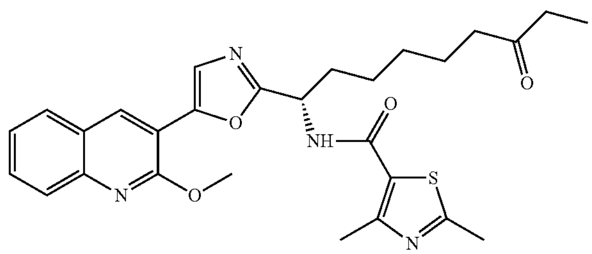 [SMILES: CCC(=O)CCCCC[C@H](NC(=O)c1sc(C)nc1C)c1ncc(-c2cc3ccccc3nc2OC)o1] | C | A | B |
| 84 | (S)-N-(1-(5-(2-methoxyquinolin-3-yl)oxazol-2-yl)-7-oxononyl)-1,3-dimethylazetidine-3-carboxamide | 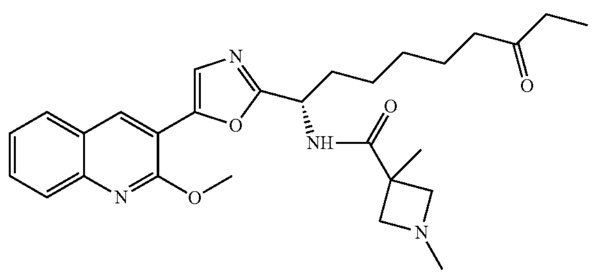 [SMILES: CCC(=O)CCCCC[C@H](NC(=O)C1(C)CN(C)C1)c1ncc(-c2cc3ccccc3nc2OC)o1] | B | A | B |
| 85 | N-((S)-1-(5-(2-methoxyquinolin-3-yl)oxazol-2-yl)-7-oxononyl)-1-methylazetidine-2-carboxamide | 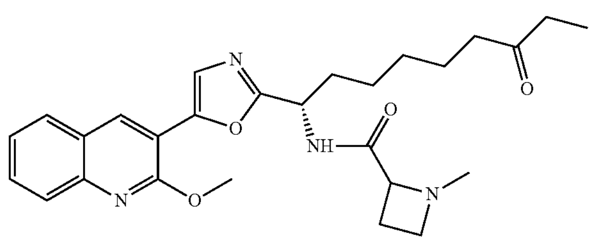 [SMILES: CCC(=O)CCCCC[C@H](NC(=O)C1CCN1C)c1ncc(-c2cc3ccccc3nc2OC)o1] | C | A | B |
| 86 | (S)-N-(1-(5-(2-methoxyquinolin-3-yl)oxazol-2-yl)-7-oxononyl)-2-(1H-1,2,4-triazol-1-yl)acetamide | 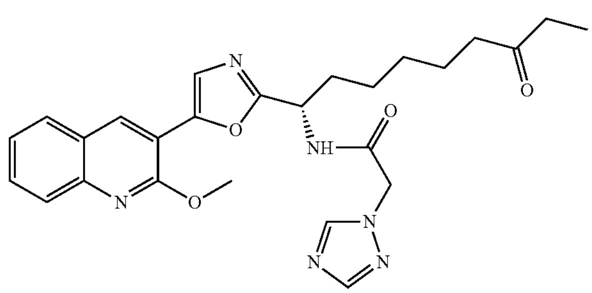 [SMILES: CCC(=O)CCCCC[C@H](NC(=O)Cn1cncn1)c1ncc(-c2cc3ccccc3nc2OC)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 87 | (S)-N-(1-(5-(2-methoxyquinolin-3-yl)oxazol-2-yl)-7-oxononyl)-1-methyl-1H-pyrazole-5-carboxamide | 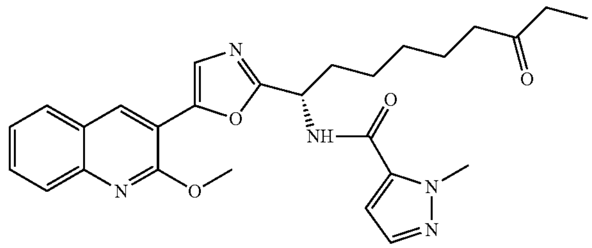 [SMILES: CCC(=O)CCCCC[C@H](NC(=O)c1ccnn1C)c1ncc(-c2cc3ccccc3nc2OC)o1] | B | A | B |
| 88 | (S)-2-(2H-indazol-2-yl)-N-(1-(5-(2-methoxyquinolin-3-yl)oxazol-2-yl)-7-oxononyl)acetamide | 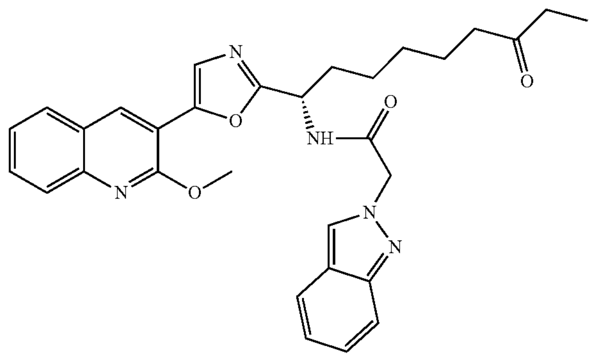 [SMILES: CCC(=O)CCCCC[C@H](NC(=O)Cn1cc2ccccc2n1)c1ncc(-c2cc3ccccc3nc2OC)o1] | C | A | B |
| 89 | (S)-N-(1-(5-(2-methoxyquinolin-3-yl)oxazol-2-yl)-7-oxononyl)-2-(pyrazolo[1,5-a]pyrimidin-2-yl)acetamide | 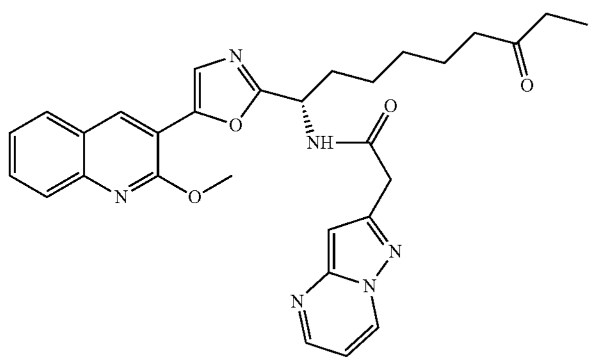 [SMILES: CCC(=O)CCCCC[C@H](NC(=O)Cc1cc2ncccn2n1)c1ncc(-c2cc3ccccc3nc2OC)o1] | C | A | B |
| 90 | (S)-N-(1-(5-(2-methoxyquinolin-3-yl)oxazol-2-yl)-7-oxononyl)-5-methyl-1,3,4-oxadiazole-2-carboxamide | 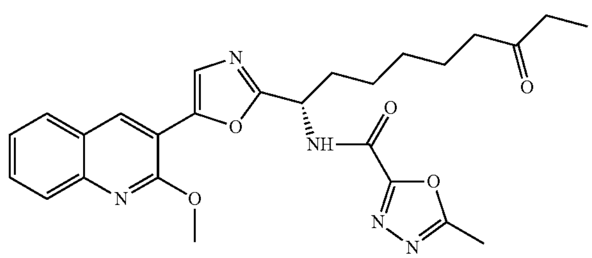 [SMILES: CCC(=O)CCCCC[C@H](NC(=O)c1nnc(C)o1)c1ncc(-c2cc3ccccc3nc2OC)o1] | C | A | B |
| 91 | (S)-N-(1-(5-(2-methoxyquinolin-3-yl)oxazol-2-yl)-7-oxononyl)nicotinamide | 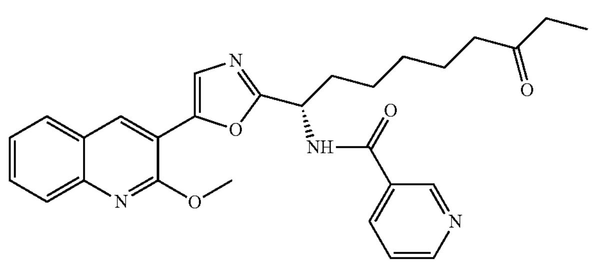 [SMILES: CCC(=O)CCCCC[C@H](NC(=O)c1cccnc1)c1ncc(-c2cc3ccccc3nc2OC)o1] | B | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 92 | (S)-1-methyl-N-(1-(5-(1-methyl-2-oxo-1,2-dihydroquinolin-3-yl)oxazol-2-yl)-7-oxononyl)azetidine-3-carboxamide | 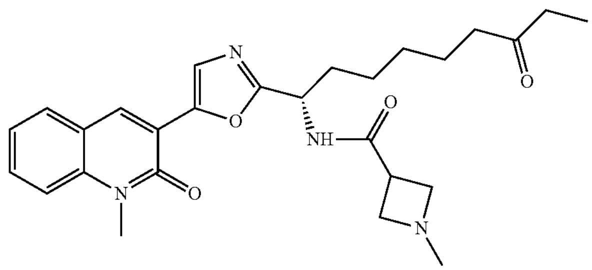 | B | A | A |
| 93 | (S)-N-(1-(5-(2-methoxyquinolin-3-yl)oxazol-2-yl)-7-oxononyl)-3-(1-methyl-1H-pyrazol-4-yl)propanamide | 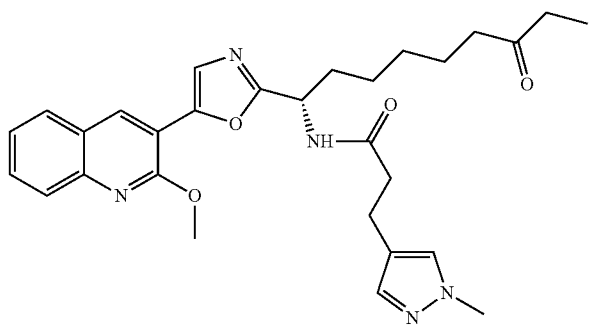 [SMILES: CCC(=O)CCCCC[C@H](NC(=O)CCc1cnn(C)c1)c1ncc(-c2cc3ccccc3nc2OC)o1] | B | A | B |
| 94 | (S)-N-(1-(5-(2-methoxyquinolin-3-yl)oxazol-2-yl)-7-oxononyl)-3-(piperidin-1-ylmethyl)isothiazole-5-carboxamide | 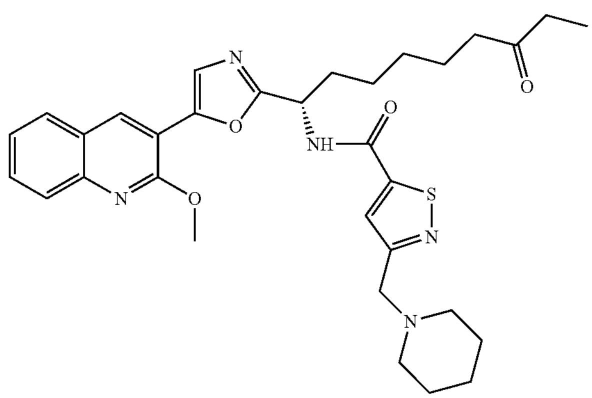 [SMILES: CCC(=O)CCCCC[C@H](NC(=O)c1cc(CN2CCCCC2)ns1)c1ncc(-c2cc3ccccc3nc2OC)o1] | C | A | B |
| 95 | 2-(3,5-dimethyl-1H-pyrazol-1-yl)-N-((S)-1-(5-(2-methoxyquinolin-3-yl)oxazol-2-yl)-7-oxononyl)propanamide | 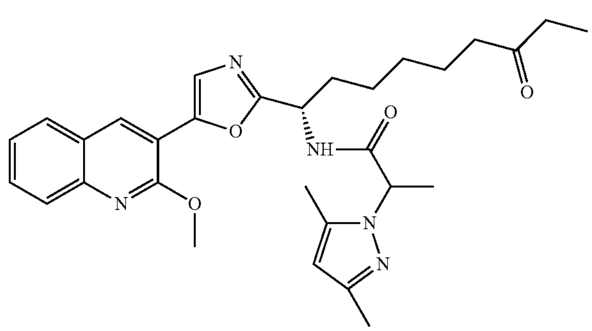 [SMILES: CCC(=O)CCCCC[C@H](NC(=O)C(C)n1nc(C)cc1C)c1ncc(-c2cc3ccccc3nc2OC)o1] | C | A | B |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 96 | (S)-N-(1-(5-(2-methoxyquinolin-3-yl)oxazol-2-yl)-7-oxononyl)-1,3-dimethyl-1H-pyrazole-5-carboxamide | 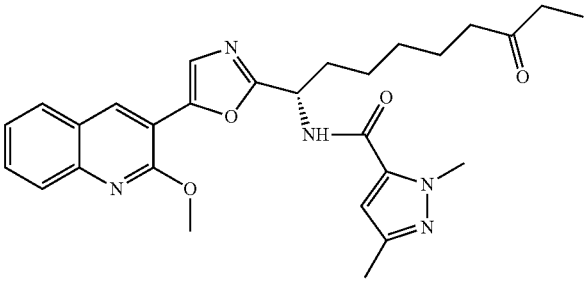 [SMILES: CCC(=O)CCCCC[C@H](NC(=O)c1cc(C)nn1C)c1ncc(-c2cc3ccccc3nc2OC)o1] | C | A | B |
| 97 | (S)-2-(1H-benzo[d]imidazol-1-yl)-N-(1-(5-(2-methoxyquinolin-3-yl)oxazol-2-yl)-7-oxononyl)acetamide | 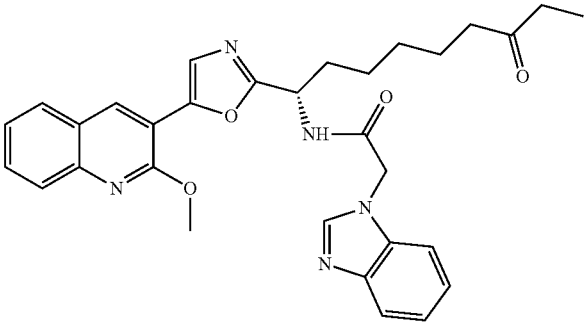 [SMILES: CCC(=O)CCCCC[C@H](NC(=O)Cn1cnc2ccccc21)c1ncc(-c2cc3ccccc3nc2OC)o1] | C | A | B |
| 98 | (S)-N-(1-(5-(2-methoxyquinolin-3-yl)oxazol-2-yl)-7-oxononyl)-1-methyl-1H-pyrazole-3-carboxamide | 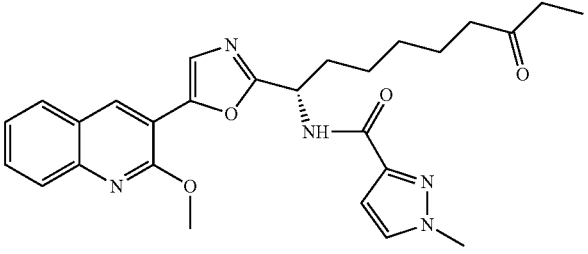 [SMILES: CCC(=O)CCCCC[C@H](NC(=O)c1ccn(C)n1)c1ncc(-c2cc3ccccc3nc2OC)o1] | C | A | B |
| 99 | (S)-N-(1-(5-(2-methoxyquinolin-3-yl)oxazol-2-yl)-7-oxononyl)-1,2,3-thiadiazole-4-carboxamide | 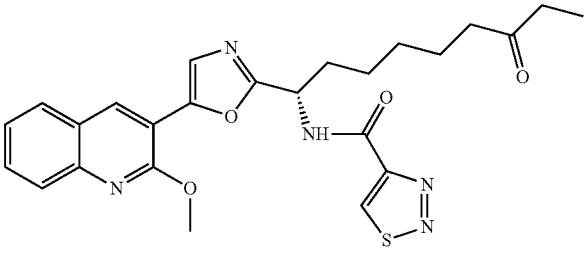 [SMILES: CCC(=O)CCCCC[C@H](NC(=O)c1csnn1)c1ncc(-c2cc3ccccc3nc2OC)o1] | C | A | B |
| 100 | (S)-N-(1-(5-(2-methoxyquinolin-3-yl)oxazol-2-yl)-7-oxononyl)isothiazole-5-carboxamide | 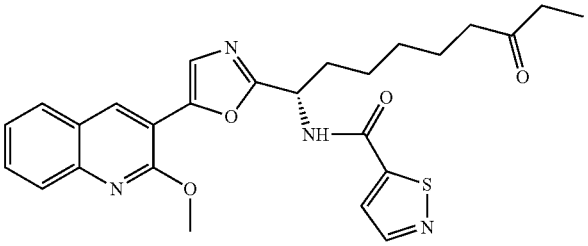 | B | A | B |

TABLE 2-continued

| Cpd | Compound Name | Structure | HbF activation EC$_{50}^{a}$ | hHDAC IC$_{50}^{a}$ | HDAC Hela Cell Based IC$_{50}^{a}$ |
|---|---|---|---|---|---|
| 101 | (S)-N-(1-(5-(2-methoxyquinolin-3-yl)oxazol-2-yl)-7-oxononyl)-4-methyl-1,2,3-thiadiazole-5-carboxamide | 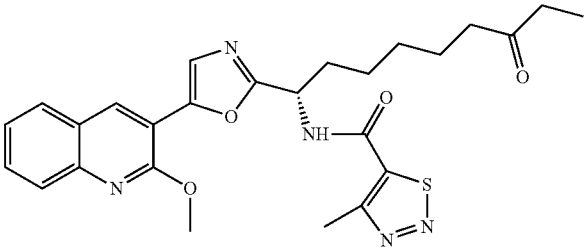 [SMILES: CCC(=O)CCCCC[C@H](NC(=O)c1snnc1C)c1ncc(-c2cc3ccccc3nc2OC)o1] | C | A | B |
| 102 | N-((S)-1-(5-(2-methoxyquinolin-3-yl)oxazol-2-yl)-7-oxononyl)-2-(1H-pyrazol-1-yl)propanamide | 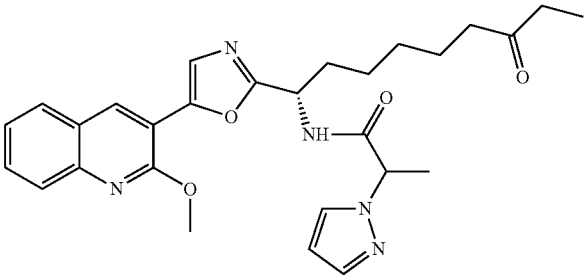 [SMILES: CCC(=O)CCCCC[C@H](NC(=O)C(C)n1cccn1)c1ncc(-c2cc3ccccc3nc2OC)o1] | C | A | B |
| 103 | (S)-2-((dimethylamino)methyl)-N-(1-(5-(2-methoxyquinolin-3-yl)oxazol-2-yl)-7-oxononyl)thiazole-4-carboxamide | 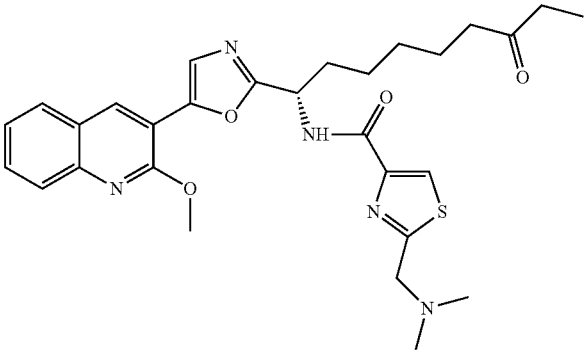 [SMILES: CCC(=O)CCCCC[C@H](NC(=O)c1csc(CN(C)C)n1)c1ncc(-c2cc3ccccc3nc2OC)o1] | C | B | B |
| 104 | N-((S)-1-(5-(2-methoxyquinolin-3-yl)oxazol-2-yl)-7-oxononyl)-1-methylpiperidine-3-carboxamide | 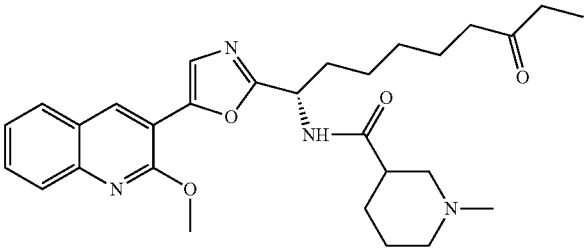 [SMILES: CCC(=O)CCCCC[C@H](NC(=O)C1CCCN(C)C1)c1ncc(-c2cc3ccccc3nc2OC)o1] | B | A | A |
| 105 | (S)-1-(dimethylamino)-N-(1-(5-(2-methoxyquinolin-3-yl)oxazol-2-yl)-7-oxononyl)cyclopentane carboxamide | 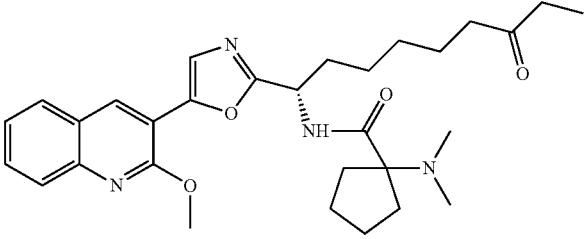 [SMILES: CCC(=O)CCCCC[C@H](NC(=O)C1(N(C)C)CCCC1)c1ncc(-c2cc3ccccc3nc2OC)o1] | B | A | A |

TABLE 2-continued

| Cpd | Compound Name | Structure | HbF activation EC$_{50}$$^a$ | hHDAC IC$_{50}$$^a$ | HDAC Hela Cell Based IC$_{50}$$^a$ |
|---|---|---|---|---|---|
| 106 | (S)-3-(dimethylamino)-N-(1-(5-(1-methyl-2-oxo-1,2-dihydroquinolin-3-yl)oxazol-2-yl)-7-oxononyl)propanamide | 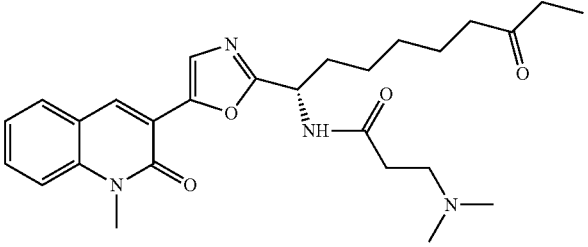 [SMILES: CCC(=O)CCCCC[C@H](NC(=O)CCN(C)C)c1ncc(-c2cc3ccccc3n(C)c2=O)o1] | A | A | A |
| 107 | (S)-2-(dimethylamino)-2-methyl-N-(1-(5-(1-methyl-2-oxo-1,2-dihydroquinolin-3-yl)oxazol-2-yl)-7-oxononyl)propanamide | 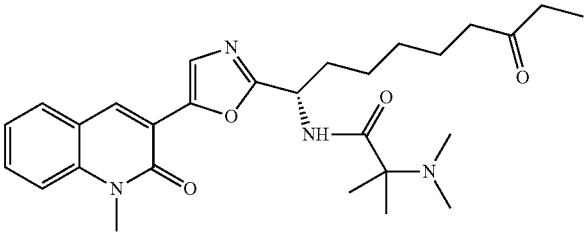 [SMILES: CCC(=O)CCCCC[C@H](NC(=O)C(C)(C)N(C)C)c1ncc(-c2cc3ccccc3n(C)c2=O)o1] | A | A | A |
| 108 | (S)-N-(1-(5-(2-methoxyquinolin-3-yl)oxazol-2-yl)-7-oxononyl)-2-(1-methylazetidin-3-yl)acetamide | 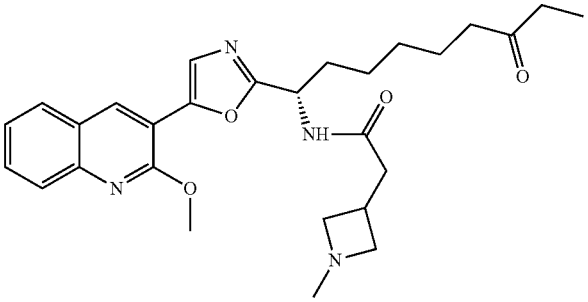 [SMILES: CCC(=O)CCCCC[C@H](NC(=O)CC1CN(C)C1)c1ncc(-c2cc3ccccc3nc2OC)o1] | B | A | A |
| 109 | (S)-1-methyl-N-(1-(5-(1-methyl-2-oxo-1,2-dihydroquinolin-3-yl)oxazol-2-yl)-7-oxononyl)piperidine-4-carboxamide | 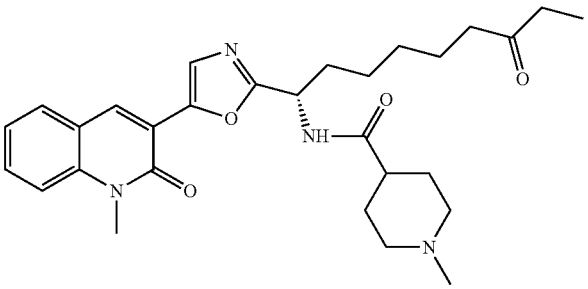 [SMILES: CCC(=O)CCCCC[C@H](NC(=O)C1CCN(C)CC1)c1ncc(-c2cc3ccccc3n(C)c2=O)o1] | B | A | A |
| 110 | (S)-N-(1-(5-(1-methyl-2-oxo-1,2-dihydroquinolin-3-yl)oxazol-2-yl)-7-oxononyl)thiazole-5-carboxamide | 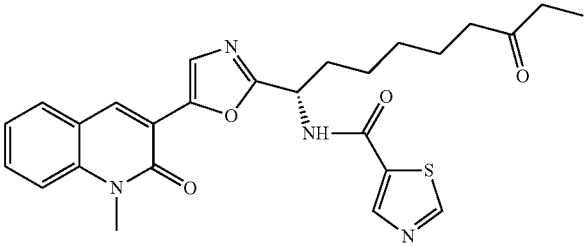 [SMILES: CCC(=O)CCCCC[C@H](NC(=O)c1cncs1)c1ncc(-c2cc3ccccc3n(C)c2=O)o1] | B | A | A |

TABLE 2-continued

| Cpd | Compound Name | Structure | HbF activation $EC_{50}^a$ | hHDAC $IC_{50}^a$ | HDAC Hela Cell Based $IC_{50}^a$ |
|---|---|---|---|---|---|
| 111 | (S)-1-(dimethylamino)-N-(1-(5-(1-methyl-2-oxo-1,2-dihydroquinolin-3-yl)oxazol-2-yl)-7-oxononyl)cyclopentane carboxamide | 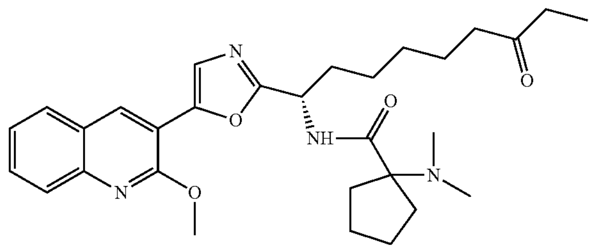 [SMILES: CCC(=O)CCCCC[C@H](NC(=O)C1(N(C)C)CCCC1)c1ncc(-c2cc3ccccc3nc2OC)o1] | A | A | A |

*A: <0.1 μM;
B: 0.1 μM-1.0 μM;
C: >1.0 μM

The erythroid differentiation of K562 cells was investigated following treatment with selected compounds of the invention. The effect on cell proliferation was first determined for all tested molecules by culture of K562 cells in the presence of increasing concentration of the compounds. The cell number per sample was then determined after 3, 4 and 5 days. The $IC_{50}$ values reported in Table 3 for the antiproliferative effect were calculated from the concentration of the compounds necessary to decrease the cell number to 50% of the values obtained in control untreated K562 cell cultures, after a 5 days culture period. Erythroid differentiation was measured by benzidine staining after 5, 6 and 7 days of cell culture and by quantitative reverse transcriptase polymerase-chain reaction (RT-qPCR) to quantify the expression of γ-globin mRNA. Different concentrations of tested compounds were employed because of their differing antiproliferative effects; accordingly, concentrations were chosen to maximize the erythroid induction effect without extensive reduction of cell viability. In Table 3 the % of benzidine positive cells and the increase in γ-globin mRNA assayed by RT-qPCR after 6 days of culture period are reported.

TABLE 3

Screening of antiproliferative and differentiation inducing properties[a]

| Cpd | Antiproliferative effect $IC_{50}$ (nM) | % of benzidine positive cells after 6 days | γ-globin mRNA content (fold induction) | Concentration (nM) |
|---|---|---|---|---|
| 2 | 75 | 10 | 1.75 | 70 |
| 37 | 600 | 16 | 7.84 | 1600 |
| 67 | 950 | 12 | 5.08 | 1800 |
| 80 | 250 | 1 | 1.03 | 200 |
| 82 | >400 | 4.5 | 0.96 | 260 |
| 92 | 50 | 8 | 1.24 | 40 |
| 106 | 41 | 8.5 | 2.01 | 60 |
| 107 | 24 | 2 | 1.87 | 40 |
| 109 | >50 | 1.5 | 1.31 | 60 |
| 110 | 200 | 5 | 1.19 | 300 |
| 111 | 47 | 6 | 2.51 | 60 |

[a]Results are presented as average of three independent experiments performed.

Table 4 reports induction of erythroid differentiation in K562 cells treated with an optimized concentration of the compound 2 in comparison with known inducers. Compound 2 is able to stimulate an increase of the proportion of benzidine-positive (hemoglobin producing) K562 cells. This is associated with an increase of the expression of γ-globin mRNA. It can be noted that in K562 cell system the studied HDAC inhibitors exhibit induction efficiency comparable to that of butyric acid and hydroxyurea, the HbF inducers most used in clinical studies to date.

TABLE 4

Induction of erythroid differentiation in K562 cells treated with Compound 2 in comparison with known inducers.

| Compound | Benzidine positive cells (%)* |
|---|---|
| Resveratrol | 70 ± 8.5 |
| Angelicin | 62 ± 8.5 |
| Cytosin arabinoside | 75 ± 5.4 |
| Mithramycin | 83 ± 5.5 |
| Cisplatin | 63 ± 8.5 |
| Butyric acid | 32 ± 6.4 |
| Hydroxyurea | 30 ± 7.5 |

TABLE 4-continued

Induction of erythroid differentiation in K562 cells treated with Compound 2 in comparison with known inducers.

| Compound | Benzidine positive cells (%)* |
|---|---|
| Compound 2 | 25 ± 3.5 |

*Percentage of K562 cells that react positively to benzidine (mean ± SD of six experiments)

The validation of the potential usefulness of the tested compounds for therapy of beta-thalassemia and sickle-cell diseases has been performed using erythroid precursor cells from beta-thalassemia patients. The culturing method of BFUe (Burst Forming Units) involves isolation of nucleated cells using Ficoll gradient centrifugation of peripheral blood. The nucleated cells are then cultured in an appropriate medium containing cytokines which promote the cell division and maturation of the pluripotent progenitor cells to BFUe and subsequently to CFUe (Colony Forming Units). This is Phase I of the culture during which the cells are committed to differentiate into erythrocytes. After 5-7 days in Phase I culture conditions the cells are transferred in fresh medium which contains erythropoietin and Stem Cell Factor (SCF) so that erythroid maturation can be completed (Phase II of the culture). Erythropoietin causes differentiation of CFUe to proerythroblasts, subsequently to mature erythroblasts and finally to erythrocytes. The test substances are added to the culture on day 5 to 7 of the Phase II. During the time period that the cells are exposed to the test agent, production of haemoglobin begins. HbF production and globin chains are evaluated using HPLC.

Figure 2:
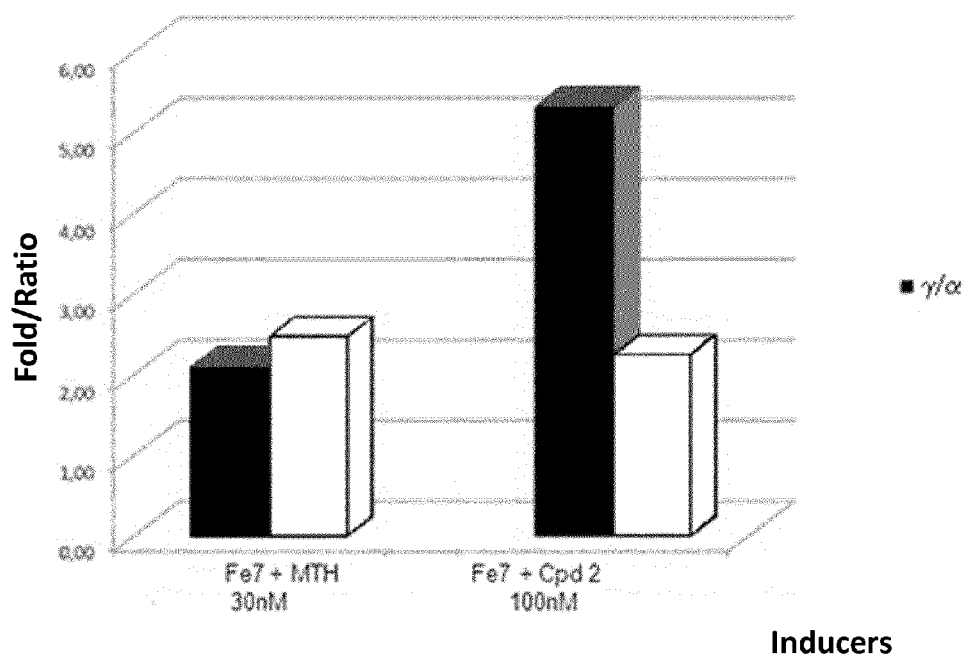
FIG. 2. Induction of globin genes in erythroid precursor cells from one β-thalassemia patient (Fe7). Cells were treated with 30 nM mithramycin (MTH) or 100 nM Compound 2, globin mRNA accumulation was analyzed by real-time quantitative RT-PCR (see materials and methods). The accumulation of mRNA for γ-globin is given as an increase compared with that of untreated control erythroid precursors (white boxes). The ratio γ-globin mRNA/α-globin mRNA was calculated (black boxes).

Further, data depicted in FIGS. 1-2 and Table 5 indicate that Compound 2 is a strong inducer of HbF in erythroid precursor cells (ErPC) from β-thalassemic patients. Interestingly, the activity of the compound is higher than that exhibited by optimal concentration of mithramycin (MTH), one of the most efficient HbF inducers in the ErPC model system (Fibach et al., Blood 2003, 102, 1276-1281). The levels of HbF accumulation achieved under these experimental conditions are clinically relevant since suppress the excess of α-globin chains.

TABLE 5

Fetal hemoglobin production in ErPC from β-thalassemia patients

| Patient n. | Untreated | MTH 30 nM | Compound 2 100 nM |
|---|---|---|---|
| 1 | 53.4 | 59.2 | 78.6 |
| 2 | 32.2 | 60.1 | 85.5 |
| 3 | 44.2 | 62.4 | 81.5 |

Results are presented as % of fetal hemoglobin production;
ND = not done

Compounds of the invention were evaluated in in vitro and in vivo pharmacokinetic studies. Results of intrinsic clearance in microsomes and in vivo dosage for selected compounds of the invention are reported in Table 6.

TABLE 6

| | $Cl_{int}$ (µl/min/mg) | | | | Dose po | AUC | Cmax |
|---|---|---|---|---|---|---|---|
| Cpd | Rat | Human | Mouse | Species | (mg/kg) | (µM * h) | (µM) |
| 2 | 33 | 13 | 27 | Mouse | 20 | 22.4 | 1.87 |
| | | | | Rat | 10 | 40.0 | 2.79 |
| 41 | ND | ND | ND | Rat | 10 | 10.14 | 0.47 |
| 42 | 21 | 3 | 15 | Mouse | 5 | 5.93 | 0.67 |
| 44 | 17 | 11 | 11 | ND | ND | ND | ND |
| 52 | 30 | 60 | 19 | Mouse | 10 | 1.75 | 0.63 |
| | | | | Rat | 10 | 5.91 | 0.58 |
| 92 | 15 | <5 | 13 | Mouse | 10 | 0.32 | 0.10 |

ND = not done

In general, tested compounds showed high to moderate oral exposure when administered to preclinical species. The HDAC inhibitors of the invention can be considered to be a new class of erythroid differentiation inducers. It has been herein demonstrated that compounds of the present invention are able to induce fetal hemoglobin production in erythroid cells isolated from β-thalassemia patients. The present experimental evidences make these compounds extremely interesting when compared to known HDAC inhibitors and compounds currently used in therapy. In this context, considering the good pharmacokinetic properties of the compounds reported herein, they could be usefully employed alone or in combination for the treatment of hemoglobinopathies and, in particular, for the treatment of β-thalassemia and sickle cell anemia.

The invention claimed is:

1. A compound of general formula (I):

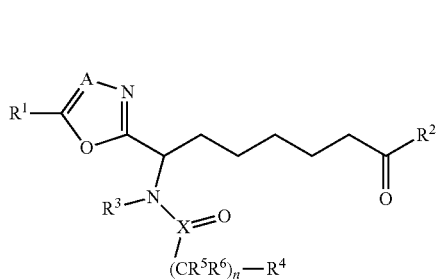 (I)

wherein:

X is C or S=O;

A is CH;

n is 0, 1, 2 or 3;

$R^1$ is phenyl, 5 or 6 membered saturated or unsaturated heterocycle, 8-10 membered unsaturated or partially saturated heterocycle containing heteroatoms independently selected from O, N and S; any of which rings being optionally substituted by one or more groups independently chosen from cyano, halogen, nitro, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$aryl, $C_{6-10}$aryloxy, $C_{6-10}$arylcarbonyl, $N(R^a)_2$, $SO_2N(R^a)_2$, $N(R^a)SO_2R^a$, 5 or 6 membered saturated or unsaturated heterocycle optionally substituted by one or more groups independently chosen from halogen, $C_{1-6}$alkyl, halo$C_{1-6}$alkyl, $C_{1-6}$alkoxy;

$R^2$ represents $C_{1-6}$alkyl or $C_{3-10}$cycloalkyl;

$R^3$ represents hydrogen or $C_{1-6}$alkyl;

$R^4$ is hydrogen, halogen, hydroxy, cyano, sulphonylamino, $C_{1-6}$alkyl, halo$C_{1-6}$alkyl, hydroxy$C_{1-6}$alkyl, $SO_2C_{1-6}$alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, $N(R^a)_2$, $C_{6-10}$aryl, $C_{6-10}$aryl$C_{1-6}$alkyl, $C_{6-10}$aryl$C_{1-6}$alkoxy; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, O or S; any of which rings being optionally substituted by one or more groups independently chosen by one or more groups independently chosen from halogen, hydroxy, amino, $C_{1-6}$alkyl, halo$C_{1-6}$alkyl, $C_{1-6}$alkoxy and halo$C_{1-6}$alkoxy;

$R^5$ and $R^6$ are independently hydrogen, $C_{1-6}$alkyl, or $CR^5R^6$ represents a carbonyl or $CR^5R^6$ represents a cyclopropyl;

each $R^a$ is independently selected from hydrogen, $C_{1-6}$alkyl, $C_{6-10}$aryl, $C_{1-6}$alkylcarbonyl and $C_{6-10}$arylcarbonyl; and pharmaceutically acceptable salts, tautomers, stereoisomers thereof.

2. A compound according to claim 1 having general formula

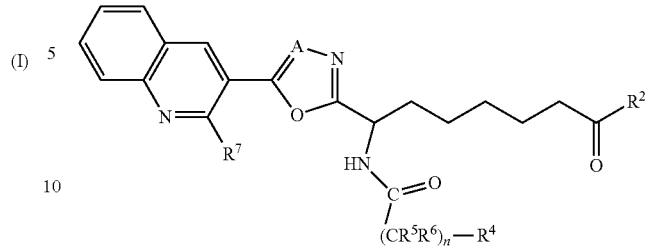

wherein

A, $R^2$ are as defined in claim 1;

n is 0 or 1;

$R^7$ is selected from the group consisting of halogen, $C_{1-6}$alkyl, $C_{1-6}$alkoxy, halo$C_{1-6}$alkyl and halo$C_{1-6}$alkoxy;

$R^5$ and $R^6$ are independently hydrogen, $C_{1-6}$alkyl, $CR^5R^6$ represents a carbonyl or $CR^5R^6$ represents a cyclopropyl;

$R^4$ is $C_{3-10}$cycloalkyl, halo$C_{3-10}$cycloalkyl, $N(R^a)_2$; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 heteroatoms independently selected from N, O and S, but not more than one of which is O or S; 7-13 membered saturated, partially saturated or unsaturated heterocycle containing heteroatoms independently selected from N, O or S; any of which rings being optionally substituted by one or more groups independently chosen from halogen, hydroxy, amino, $C_{1-6}$alkyl, halo$C_{1-6}$alkyl, $C_{1-6}$alkoxy and halo$C_{1-6}$alkoxy;

$R^a$ is $C_{1-6}$alkyl;

and pharmaceutically acceptable salts, tautomers, stereoisomers thereof.

3. A compound according to claim 1 having general formula (III):

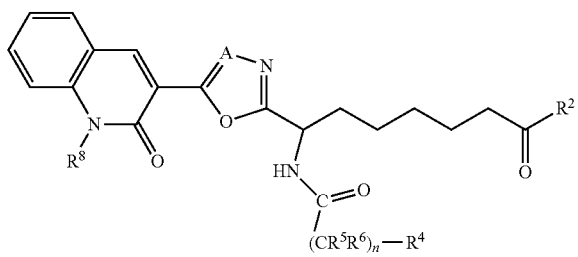

wherein

A, $R^2$ are as defined in claim 1 and n is 0 or 1;

$R^8$ is $C_{1-6}$alkyl;

$R^5$ and $R^6$ are independently hydrogen, $C_{1-6}$alkyl, $CR^5R^6$ represents a carbonyl or $CR^5R^6$ represents a cyclopropyl;

$R^4$ is $C_{3-10}$cycloalkyl, halo$C_{3-10}$cycloalkyl, $N(R^a)_2$; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 heteroatoms independently selected from N, O and S, but not more than one of which is O or S; 7-13 membered saturated, partially saturated or unsaturated heterocycle containing heteroatoms independently selected from N, O or S; any of which rings being optionally substituted by one or more groups independently chosen from halogen, hydroxy, amino, $C_{1-6}$alkyl, halo$C_{1-6}$alkyl, $C_{1-6}$alkoxy and halo$C_{1-6}$alkoxy;

$R^a$ is $C_{1-6}$alkyl;

and pharmaceutically acceptable salts, tautomers, stereoisomers thereof.

4. A compound selected from the group consisting of:
(S)-2-(5-methoxy-2-methyl-1H-indol-3-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-1-methylazetidine-3-carboxamide;
(S)-1-methyl-N-(7-oxo-1-(5-phenyloxazol-2-yl)nonyl)piperidine-4-carboxamide;
(S)-2-(5-methoxy-2-methyl-1H-indol-3-yl)-N-(7-oxo-1-(5-phenyloxazol-2-yl)nonyl)acetamide;
((S)-N-(1-(5-(2,3-dihydrobenzo[b][1,4]dioxin-5-yl)oxazol-2-yl)-7-oxononyl)-1-methylpiperidine-4-carboxamide;
(S)-N-(7-oxo-1-(5-phenyloxazol-2-yl)nonyl)thiazole-5-carboxamide;
(S)-3-(dimethylamino)-N-(7-oxo-1-(5-phenyloxazol-2-yl)nonyl)propanamide;
1-methyl-N-((S)-7-oxo-1-(5-phenyloxazol-2-yl)nonyl)pyrrolidine-3-carboxamide;
(S)-2-(dimethylamino)-2-methyl-N-(7-oxo-1-(5-phenyloxazol-2-yl)nonyl)propanamide;
(S)-N-(7-oxo-1-(5-phenyloxazol-2-yl)nonyl)cyclopropane-1,1-dicarboxamide;
(S)-2-(methylsulfonyl)-N-(7-oxo-1-(5-phenyloxazol-2-yl)nonyl)acetamide;
((S)-2-cyclohexyl-N-(7-oxo-1-(5-phenyloxazol-2-yl)nonyl)acetamide;
(R)-2-oxo-N-((S)-7-oxo-1-(5-phenyloxazol-2-yl)nonyl)thiazolidine-4-carboxamide;
(S)-2-chloro-N-(7-oxo-1-(5-phenyloxazol-2-yl)nonyl)isonicotinamide;
(S)-2-(4-methylpiperazin-1-yl)-N-(7-oxo-1-(5-phenyloxazol-2-yl)nonyl)acetamide;
(S)-N-(7-oxo-1-(5-phenyloxazol-2-yl)nonyl)quinoxaline-6-carboxamide;
1-methyl-N-((S)-7-oxo-1-(5-phenyloxazol-2-yl)nonyl)piperidine-3-carboxamide;
(S)-2-(2-methyl-1H-benzo[d]imidazol-1-yl)-N-(7-oxo-1-(5-phenyloxazol-2-yl)nonyl)acetamide;
(S)-6-chloro-N-(7-oxo-1-(5-phenyloxazol-2-yl)nonyl)imidazo[1,2-b]pyridazine-2-carboxamide;
(S)-N-(7-oxo-1-(5-phenyloxazol-2-yl)nonyl)-1H-indole-6-carboxamide;
1-methyl-N-((S)-7-oxo-1-(5-phenyloxazol-2-yl)nonyl)azepane-2-carboxamide;
(S)-N-(7-oxo-1-(5-phenyloxazol-2-yl)nonyl)-4-sulfamoylbutanamide;
2-methyl-N-((S)-7-oxo-1-(5-phenyloxazol-2-yl)nonyl)tetrahydrofuran-2-carboxamide;
(S)-3,3-difluoro-N-(7-oxo-1-(5-phenyloxazol-2-yl)nonyl)cyclobutanecarboxamide;
3-(1-methylpiperidin-3-yl)-N-((S)-7-oxo-1-(5-phenyloxazol-2-yl)nonyl)propanamide;
(S)-3-(2-ethyl-1H-benzo[d]imidazol-1-yl)-N-(7-oxo-1-(5-phenyloxazol-2-yl)nonyl)propanamide;
(S)-$N^1$,$N^1$-dimethyl-$N^2$-(7-oxo-1-(5-phenyloxazol-2-yl)nonyl)oxalamide;
(S)-2-(4-methylpiperazin-1-yl)-2-oxo-N-(7-oxo-1-(5-phenyloxazol-2-yl)nonyl)acetamide;
(S)-3-(2-ethyl-1H-benzo[d]imidazol-1-yl)-N-(1-(5-(2-methoxyquinolin-3-yl)oxazol-2-yl)-7-oxononyl)propanamide;
(S)-4-methyl-N-(7-oxo-1-(5-phenyloxazol-2-yl)nonyl)-3,4-dihydro-2H-benzo[b][1,4]oxazine-7-carboxamide;
(S)-2-(imidazo[2,1-b]thiazol-3-yl)-N-(7-oxo-1-(5-phenyloxazol-2-yl)nonyl)acetamide;
(S)-1-methyl-N-(7-oxo-1-(5-phenyloxazol-2-yl)nonyl)azetidine-3-carboxamide;
(S)-2-(2-aminothiazol-4-yl)-N-(7-oxo-1-(5-phenyloxazol-2-yl)nonyl)acetamide;
N-((S)-1-(5-(2-methoxyquinolin-3-yl)oxazol-2-yl)-7-oxononyl)-1-methylpyrrolidine-3-carboxamide;
(S)-2-(dimethylamino)-N-(1-(5-(2-methoxyquinolin-3-yl)oxazol-2-yl)-7-oxononyl)-2-methylpropanamide;
(S)-N1-(1-(5-(2-methoxyquinolin-3-yl)oxazol-2-yl)-7-oxononyl)-N2,N2-dimethyloxalamide;
(S)-N-(1-(5-(2-methoxyquinolin-3-yl)oxazol-2-yl)-7-oxononyl)-2-(4-methylpiperazin-1-yl)-2-oxoacetamide;
(S)-3-(dimethylamino)-N-(1-(5-(2-methoxyquinolin-3-yl)oxazol-2-yl)-7-oxononyl)propanamide;
(S)-9-((2-(dimethylamino)ethyl)amino)-9-(5-(2-methoxyquinolin-3-yl)oxazol-2-yl)nonan-3-one;
(S)-N-(1-(5-(2-methoxyquinolin-3-yl)oxazol-2-yl)-7-oxononyl)thiazole-5-carboxamide;
(S)-N-(1-(5-(2-methoxyquinolin-3-yl)oxazol-2-yl)-7-oxononyl)quinuclidine-4-carboxamide;
(R)-N-(1-(5-(2-methoxyquinolin-3-yl)oxazol-2-yl)-7-oxononyl)-1-methylazetidine-3-carboxamide;
(S)-2-(5-methoxy-2-methyl-1H-indol-3-yl)-N-(1-(5-(2-methoxyquinolin-3-yl)oxazol-2-yl)-7-oxononyl)-N-methylacetamide;
(S)-1-methyl-N-(7-oxo-1-(5-(2-oxo-1,2-dihydroquinolin-3-yl)oxazol-2-yl)nonyl)azetidine-3-carboxamide;
(S)-N-(1-(5-(4-(1H-pyrazol-5-yl)phenyl)oxazol-2-yl)-7-oxononyl)-1-methylazetidine-3-carboxamide;
(S)-1-methyl-N-(1-(5-(4-(1-methyl-1H-pyrazol-5-yl)phenyl)oxazol-2-yl)-7-oxononyl)azetidine-3-carboxamide;
(S)-1-acetyl-N-(1-(5-(2-methoxyquinolin-3-yl)oxazol-2-yl)-7-oxononyl)azetidine-3-carboxamide;
(S)-1-benzyl-N-(1-(5-(2-methoxyquinolin-3-yl)oxazol-2-yl)-7-oxononyl)azetidine-3-carboxamide;
(S)-N-(1-(5-(2-methoxyquinolin-3-yl)oxazol-2-yl)-7-oxononyl)azetidine-3-carboxamide;
(S)-4,4-difluoro-N-((S)-1-(5-(2-methoxyquinolin-3-yl)oxazol-2-yl)-7-oxononyl)-1-methylpyrrolidine-2-carboxamide;
(S)-N-(1-(5-(2-methoxyquinolin-3-yl)oxazol-2-yl)-7-oxononyl)-2-(1H-1,2,3-triazol-1-yl)acetamide;
(S)-4,4-difluoro-N-((S)-1-(5-(2-methoxyquinolin-3-yl)oxazol-2-yl)-7-oxononyl)pyrrolidine-2-carboxamide;
(S)-N-(1-(5-(4-(1H-pyrazol-1-yl)phenyl)oxazol-2-yl)-7-oxononyl)-1-methylazetidine-3-carboxamide;
(S)-N-(1-(5-(4-(1H-pyrazol-1-yl)phenyl)oxazol-2-yl)-7-oxononyl)-1-acetylazetidine-3-carboxamide;
(S)-2-(dimethylamino)-4,4,4-trifluoro-N-((S)-1-(5-(2-methoxyquinolin-3-yl)oxazol-2-yl)-7-oxononyl)butanamide;
(R)-2-(dimethylamino)-4,4,4-trifluoro-N-((S)-1-(5-(2-methoxyquinolin-3-yl)oxazol-2-yl)-7-oxononyl)butanamide;
(S)-N-(1-(5-(4-(6-methoxypyridin-3-yl)phenyl)oxazol-2-yl)-7-oxononyl)-1-methylazetidine-3-carboxamide;

(2S,4S)-4-fluoro-N-((S)-1-(5-(2-methoxyquinolin-3-yl)oxazol-2-yl)-7-oxononyl)-1-methylpyrrolidine-2-carboxamide;
(S)-3-fluoro-N-(1-(5-(2-methoxyquinolin-3-yl)oxazol-2-yl)-7-oxononyl)-1-methylazetidine-3-carboxamide;
(S)-4-fluoro-N-(1-(5-(2-methoxyquinolin-3-yl)oxazol-2-yl)-7-oxononyl)-1-methylpiperidine-4-carboxamide;
(S)-N-(1-(5-(2-methoxyquinolin-3-yl)oxazol-2-yl)-7-oxononyl)-2-morpholino-2-oxoacetamide;
(S)-1-methyl-N-(7-oxo-1-(5-(quinolin-8-yl)oxazol-2-yl)nonyl)azetidine-3-carboxamide;
N-((S)-1-(5-(2-methoxyquinolin-3-yl)oxazol-2-yl)-7-oxononyl)-5-oxopyrrolidine-3-carboxamide;
(S)-2-(1H-imidazol-4-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-2-(pyridin-3-yl)acetamide;
(S)-3-(1H-imidazol-1-yl)-N-(1-(5-(2-methoxyquinolin-3-yl)oxazol-2-yl)-7-oxononyl)propanamide;
(S)-N-(1-(5-(2-methoxyquinolin-3-yl)oxazol-2-yl)-7-oxononyl)-2-(thiazol-2-yl)acetamide;
(S)-N-(1-(5-(2-methoxyquinolin-3-yl)oxazol-2-yl)-7-oxononyl)-2-(4-methyl-1,2,5-oxadiazol-3-yl)acetamide;
(S)-N-(1-(5-(2-methoxyquinolin-3-yl)oxazol-2-yl)-7-oxononyl)-2-(3-methyl-1H-pyrazol-1-yl)acetamide;
(S)-N-(1-(5-(2-methoxyquinolin-3-yl)oxazol-2-yl)-7-oxononyl)-2-(pyrimidin-2-yl)acetamide;
(S)-2-(3,5-dimethyl-1H-1,2,4-triazol-1-yl)-N-(1-(5-(2-methoxyquinolin-3-yl)oxazol-2-yl)-7-oxononyl)acetamide;
(S)-2-(3,5-dimethyl-1H-pyrazol-1-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-2-(pyrrolidin-1-ylmethyl)thiazole-5-carboxamide;
(S)-N-(1-(5-(2-methoxyquinolin-3-yl)oxazol-2-yl)-7-oxononyl)-2,4-dimethylthiazole-5-carboxamide;
(S)-N-(1-(5-(2-methoxyquinolin-3-yl)oxazol-2-yl)-7-oxononyl)-1,3-dimethylazetidine-3-carboxamide;
N-((S)-1-(5-(2-methoxyquinolin-3-yl)oxazol-2-yl)-7-oxononyl)-1-methylazetidine-2-carboxamide;
(S)-N-(1-(5-(2-methoxyquinolin-3-yl)oxazol-2-yl)-7-oxononyl)-2-(1H-1,2,4-triazol-1-yl)acetamide;
(S)-N-(1-(5-(2-methoxyquinolin-3-yl)oxazol-2-yl)-7-oxononyl)-1-methyl-1H-pyrazole-5-carboxamide;
(S)-2-(2H-indazol-2-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-2-(pyrazolo[1,5-a]pyrimidin-2-yl)acetamide;
(S)-N-(1-(5-(2-methoxyquinolin-3-yl)oxazol-2-yl)-7-oxononyl)-5-methyl-1,3,4-oxadiazole-2-carboxamide;
(S)-N-(1-(5-(2-methoxyquinolin-3-yl)oxazol-2-yl)-7-oxononyl)nicotinamide;
(S)-1-methyl-N-(1-(5-(1-methyl-2-oxo-1,2-dihydroquinolin-3-yl)oxazol-2-yl)-7-oxononyl)azetidine-3-carboxamide;
(S)-N-(1-(5-(2-methoxyquinolin-3-yl)oxazol-2-yl)-7-oxononyl)-3-(1-methyl-1H-pyrazol-4-yl)propanamide;
(S)-N-(1-(5-(2-methoxyquinolin-3-yl)oxazol-2-yl)-7-oxononyl)-3-(piperidin-1-ylmethyl)isothiazole-5-carboxamide;
2-(3,5-dimethyl-1H-pyrazol-1-yl)-N-((S)-1-(5-(2-methoxyquinolin-3-yl)oxazol-2-yl)-7-oxononyl)propanamide;
(S)-N-(1-(5-(2-methoxyquinolin-3-yl)oxazol-2-yl)-7-oxononyl)-1,3-dimethyl-1H-pyrazole-5-carboxamide;
(S)-2-(1H-benzo[d]imidazol-1-yl)-N-(1-(5-(2-methoxyquinolin-3-yl)oxazol-2-yl)-7-oxononyl)acetamide;
(S)-N-(1-(5-(2-methoxyquinolin-3-yl)oxazol-2-yl)-7-oxononyl)-1-methyl-1H-pyrazole-3-carboxamide;
(S)-N-(1-(5-(2-methoxyquinolin-3-yl)oxazol-2-yl)-7-oxononyl)-1,2,3-thiadiazole-4-carboxamide;
(S)-N-(1-(5-(2-methoxyquinolin-3-yl)oxazol-2-yl)-7-oxononyl)isothiazole-5-carboxamide;
(S)-N-(1-(5-(2-methoxyquinolin-3-yl)oxazol-2-yl)-7-oxononyl)-4-methyl-1,2,3-thiadiazole-5-carboxamide;
N-((S)-1-(5-(2-methoxyquinolin-3-yl)oxazol-2-yl)-7-oxononyl)-2-(1H-pyrazol-1-yl)propanamide;
(S)-2-((dimethylamino)methyl)-N-(1-(5-(2-methoxyquinolin-3-yl)oxazol-2-yl)-7-oxononyl)thiazole-4-carboxamide;
N-((S)-1-(5-(2-methoxyquinolin-3-yl)oxazol-2-yl)-7-oxononyl)-1-methylpiperidine-3-carboxamide;
(S)-1-(dimethylamino)-N-(1-(5-(2-methoxyquinolin-3-yl)oxazol-2-yl)-7-oxononyl)cyclopentanecarboxamide;
(S)-3-(dimethylamino)-N-(1-(5-(1-methyl-2-oxo-1,2-dihydroquinolin-3-yl)oxazol-2-yl)-7-oxononyl)propanamide;
(S)-2-(dimethylamino)-2-methyl-N-(1-(5-(1-methyl-2-oxo-1,2-dihydroquinolin-3-yl)oxazol-2-yl)-7-oxononyl)propanamide;
(S)-N-(1-(5-(2-methoxyquinolin-3-yl)oxazol-2-yl)-7-oxononyl)-2-(1-methylazetidin-3-yl)acetamide;
(S)-1-methyl-N-(1-(5-(1-methyl-2-oxo-1,2-dihydroquinolin-3-yl)oxazol-2-yl)-7-oxononyl)piperidine-4-carboxamide;
(S)-N-(1-(5-(1-methyl-2-oxo-1,2-dihydroquinolin-3-yl)oxazol-2-yl)-7-oxononyl)thiazole-5-carboxamide;
(S)-1-(dimethylamino)-N-(1-(5-(1-methyl-2-oxo-1,2-dihydroquinolin-3-yl)oxazol-2-yl)-7-oxononyl)cyclopentanecarboxamide;
and pharmaceutically acceptable salts, tautomers, stereoisomers thereof.

5. A compound according to claim 4 being (S)-N-(1-(5-(2-methoxyquinolin-3-yl)oxazol-2-yl)-7-oxononyl)-1-methylazetidine-3-carboxamide and pharmaceutically acceptable salts, tautomers, stereoisomers thereof.

6. A method for the treatment of β-thalassemia or sickle cell anemia, comprising administering a compound according to claim 1 to a mammal in need thereof.

7. A method for the treatment of the treatment of β-thalassemia or sickle cell anemia comprising administering a compound of formula (IV)

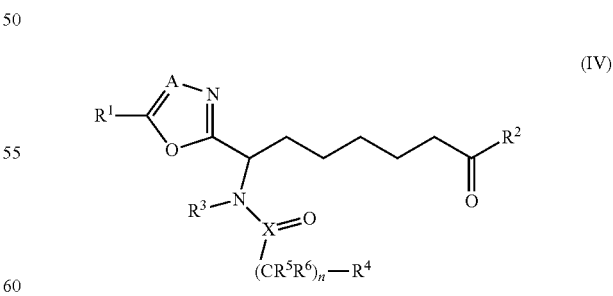

wherein:
X is C or S=O;
A represents is N;
n is 0, 1, 2 or 3;
$R^1$ is phenyl, 5 or 6 membered saturated or unsaturated heterocycle, 8-10 membered unsaturated or partially saturated heterocycle containing heteroatoms independently selected from O, N and S; any of which rings being optionally substituted by one or more groups independently chosen from cyano, halogen, nitro, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$aryl, $C_{6-10}$aryloxy, $C_{6-10}$arylcarbonyl, $N(R^a)_2$, $SO_2N(R^a)_2$, $N(R^a)SO_2R^a$, 5 or 6 membered saturated or unsaturated heterocycle optionally substituted by one or more groups independently chosen from halogen, $C_{1-6}$alkyl, halo$C_{1-6}$alkyl, $C_{1-6}$alkoxy;

$R^2$ represents $C_{1-6}$alkyl or $C_{3-10}$cycloalkyl;

$R^3$ represents hydrogen or $C_{1-6}$alkyl;

$R^4$ is hydrogen, halogen, hydroxy, cyano, sulphonylamino, $C_{1-6}$alkyl, halo$C_{1-6}$alkyl, hydroxy$C_{1-6}$alkyl, $SO_2C_{1-6}$alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, $N(R^a)_2$, $C_{6-10}$aryl, $C_{6-10}$aryl$C_{1-6}$alkyl, $C_{6-10}$aryl$C_{1-6}$alkoxy; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independent selected from N, O or S; any of which rings being optionally substituted by one or more groups independently chosen by one or more groups independently chosen from halogen, hydroxy, amino, $C_{1-6}$alkyl, halo$C_{1-6}$alkyl, $C_{1-6}$alkoxy and halo$C_{1-6}$alkoxy;

$R^5$ and $R^6$ are independently hydrogen, $C_{1-6}$alkyl, or $CR^5R^6$ represents a carbonyl or $CR^5R^6$ represents a cyclopropyl;

each $R^a$ is independently selected from the group consisting of hydrogen, $C_{1-6}$alkyl, $C_{6-10}$aryl, $C_{1-6}$alkylcarbonyl and $C_{6-10}$arylcarbonyl; and pharmaceutically acceptable salts, tautomers, stereoisomers thereof to a mammal in need thereof.

8. The method of claim 7, wherein the compound of general formula (IV) is selected from the group consisting of:
- (S)-N1-(1-(5-(2-methoxyquinolin-3-yl)-1,3,4-oxadiazol-2-yl)-7-oxononyl)-N2,N2-dimethyloxalamide;
- (S)-N-(1-(5-(2-methoxyquinolin-3-yl)-1,3,4-oxadiazol-2-yl)-7-oxononyl)-2-(4-methylpiperazin-1-yl)-2-oxoacetamide;
- (S)-N-(1-(5-(2-methoxyquinolin-3-yl)-1,3,4-oxadiazol-2-yl)-7-oxononyl)-1-methylpiperidine-4-carboxamide;
- (S)-2-(5-methoxy-2-methyl-1H-indol-3-yl)-N-(1-(5-(2-methoxyquinolin-3-yl)-1,3,4-oxadiazol-2-yl)-7-oxononyl)acetamide;
- (S)-N-(1-(5-(2-methoxyquinolin-3-yl)-1,3,4-oxadiazol-2-yl)-7-oxononyl)thiazole-5-carboxamide;
- (S)-3-(2-ethyl-1H-benzo[d]imidazol-1-yl)-N-(1-(5-(2-methoxyquinolin-3-yl)-1,3,4-oxadiazol-2-yl)-7-oxononyl)propanamide;
- (S)-3-(dimethylamino)-N-(1-(5-(2-methoxyquinolin-3-yl)-1,3,4-oxadiazol-2-yl)-7-oxononyl)propanamide;
- (S)-N-(1-(5-(2-methoxyquinolin-3-yl)-1,3,4-oxadiazol-2-yl)-7-oxononyl)-1-methylazetidine-3-carboxamide;
- (S)-1-methyl-N-(1-(5-(1-methyl-2-oxo-1,2-dihydroquinolin-3-yl)-1,3,4-oxadiazol-2-yl)-7-oxononyl)azetidine-3-carboxamide;

and pharmaceutically acceptable salts, tautomers, stereoisomers thereof.

9. A pharmaceutical composition comprising an effective amount of one or more compounds according to claim 1 or a pharmaceutically acceptable prodrug thereof, alone or in combination with other active compounds, and at least one pharmaceutically acceptable excipient.

10. The pharmaceutical composition according to claim 9 wherein the other active compound is 2,2-dimethylbutyrate, hydroxyurea, decitabine, erythropoietin, trichostatin, valproic acid, or a combination thereof.

* * * * *